US008715931B2

(12) United States Patent \
Nakashiro et al.

(10) Patent No.: US 8,715,931 B2 \
(45) Date of Patent: May 6, 2014

(54) METHOD FOR ANALYZING CERVICAL LYMPH NODE METASTASIS, AND TUMOR MARKER FOR HEAD AND NECK CANCER

(75) Inventors: Koichi Nakashiro, Ehime (JP); Hiroyuki Hamakawa, Ehime (JP); Hiroyuki Goda, Ehime (JP)

(73) Assignee: National University Corporation Ehime University, Ehime (JP)

( * ) Notice: Subject to any disclaimer, the term of this patent is extended or adjusted under 35 U.S.C. 154(b) by 0 days.

(21) Appl. No.: 13/518,656

(22) PCT Filed: Dec. 22, 2010

(86) PCT No.: PCT/JP2010/073129 \
§ 371 (c)(1), \
(2), (4) Date: Jun. 22, 2012

(87) PCT Pub. No.: WO2011/078223 \
PCT Pub. Date: Jun. 30, 2011

(65) Prior Publication Data

US 2012/0270218 A1    Oct. 25, 2012

(30) Foreign Application Priority Data

Dec. 24, 2009   (JP) ................. 2009-292611

(51) Int. Cl. \
*C12Q 1/68*    (2006.01)
(52) U.S. Cl. \
USPC ........................................................ 435/6.1
(58) Field of Classification Search \
None \
See application file for complete search history.

(56) References Cited

U.S. PATENT DOCUMENTS

| 8,299,233 | B2 * | 10/2012 | Andre et al. ............... 536/24.31 |
| 2006/0019290 | A1 | 1/2006 | Godfrey et al. |
| 2010/0068709 | A1 | 3/2010 | Nagata et al. |

FOREIGN PATENT DOCUMENTS

| CN | 101298628 A | 11/2008 |
| CN | 101329350 A | 12/2008 |
| EP | 2083087 A1 | 7/2009 |
| JP | 2007-000052 | 1/2007 |
| JP | 2008-505644 | 2/2008 |
| JP | 2009-034071 | 2/2009 |
| WO | 2008/044504 | 4/2008 |
| WO | WO 2008079269 A3 * | 12/2008 |

OTHER PUBLICATIONS

Biewemga et al, Gynecologic Oncology, 2008, vol. 108, pp. 520-526.*
Sato et al., Sentinel lymph node biopsy using technetium-99 m labeled tin colloids in breast cancer, Journal of Clinical and Experimental Medicine, vol. 192, pp. 147-150, 2000.
Matsuzuka et al., A suggested method for lymphatic mapping in squamous cell carcinoma of the head and neck, Head and Neck Cancer, vol. 27, pp. 192-197, 2001.
Kihara et al., Study of sentinel lymph node biopsy in N0 oral cancer, Head and Neck Cancer, vol. 28, pp. 108-113, 2002.
Morton et al., Technical details of intraoperative lymphatic mapping for early stage melanoma, Arch Surg, vol. 127, pp. 392-399, 1992.
Hamakawa et al., Genetic diagnosis of micrometastasis based on SCC antigen mRNA in cervical lymph nodes of head and neck cancer, Clinical & Experimental Metastasis, vol. 17, pp. 593-599, 1999.
Hamakawa et al., Histological study on pN upgrading or oral cancer, Virchows Arch, vol. 437, pp. 116-121, 2000.
Onishi, Genetic diagnosis of micrometastasis in cervical lymph nodes of oral cancer by real-time quantitative PCR, Ehime Medical Journal, vol. 21, pp. 183-191, 2002.
Nakashiro et al., Intraoperative rapid detection of micrometastasis in sentinel lymph nodes of oral malignant tumors, Head and Neck Cancer, vol. 29, pp. 64-69, 2003.
Ferris et al., Molecular staging of cervical lymph nodes in squamous cell carcinoma of the head and neck, Cancer Research, vol. 65, pp. 2147-2156, 2005.
Hamakawa, Oral Cancer—Novel diagnosis and treatment, The Japanese Journal in Clinical and Experimental Medicine, vol. 82, pp. 1201-1205, 2005 (see International Search Report).
Hamakawa, Genetic diagnosis of oral cancer (from diagnosis to therapy), J. Hard Tissue Biology, vol. 14, pp. 163-165, 2005 (see International Search Report).
Hamakawa, Genetic diagnosis for micrometastasis of oral cancer, Journal of Japanese Stomatological Society, vol. 50, pp. 145-154, 2001 (see English Abstract and International Search Report).
Goda et al., Application of OSNA to oral cancer sentinel lymph node biopsy and the problem, Japan Society of Clinical Oncology Sokai Shorokugo, vol. 42, p. 436, OS036-5, 2007 (see International Search Report).
Oka et al., Abstract 720: Identification of novel molecular markers for detecting lymph node metastasis of oral squamous cell carcinoma, Cancer Research, vol. 72, pp. 720 (2012).
European Search Report dated Oct. 25, 2012 for corresponding EP Patent Application No. 10839453.7.
Office Action issued in corresponding Chinese Patent Application No. 201080058541.X dated Jun. 8, 2013.
Tumour Markers and its Advances in Head and Neck Cancer Research, summarized by Guo Xiuchan, Foreign Medical Sciences (Section of Otolaryngology Foreign Medical). (1994).
Diagnosis of laryngocarcinoma before treatment and the effect of image during stages, translated by Luo Jianhua, Foreign Medical Sciences (Section of Otolaryngology Foreign Medical). (2003).

* cited by examiner

*Primary Examiner* — Anne Gussow \
*Assistant Examiner* — Mindy G Brown \
(74) *Attorney, Agent, or Firm* — Morgan, Lewis & Bockius LLP

(57) ABSTRACT

Provided are a method for analyzing metastasis of head and neck cancer to a cervical lymph node, and a tumor marker for head and neck cancer used therein. Specifically, provided is a method for analyzing metastasis of head and neck cancer to a cervical lymph node, involving: measuring an expression level of at least one gene selected from the group consisting of genes represented by SEQ ID NOS: 1 to 36 in the sequence listing in a cervical lymph node sample; and comparing the aforementioned expression level with a reference value. Also provided is a tumor marker for head and neck cancer used in the aforementioned method for analyzing cervical lymph node metastasis, including at least one gene selected from the group consisting of genes represented by SEQ ID NOS: 1 to 36 in the sequence listing, and/or an expression product of the aforementioned gene and/or an expression level thereof.

7 Claims, 5 Drawing Sheets

SEQUENCE LISTING

```
<160> NUMBER OF SEQ ID NOS: 36

<210> SEQ ID NO 1
<211> LENGTH: 2345
<212> TYPE: DNA
<213> ORGANISM: Homo sapiens
<300> PUBLICATION INFORMATION:
<308> DATABASE ACCESSION NUMBER: NM_173086
<309> DATABASE ENTRY DATE: 2009-07-21
```

<313> RELEVANT RESIDUES IN SEQ ID NO: (1)..(2345)

<400> SEQUENCE: 1

| | | | | | |
|---|---|---|---|---|---|
| cgcctccagc | ctccaacgct | cgccacagcc | ctctcatctc | ctggaaccat ggccagcaca | 60 |
| tccaccacca | tcaggagcca | cagcagcagc | cgccggggtt | tcagtgccaa ctcagccagg | 120 |
| ctccctgggg | tcagccgctc | tggcttcagc | agcatctccg | tgtcccgctc caggggcagt | 180 |
| ggtggcctgg | gtggtgcatg | tggaggagct | ggctttggca | gccgcagtct gtatggcctg | 240 |
| ggggctcca | agaggatctc | cattggaggg | ggcagctgtg | ccatcagtgg cggctatggc | 300 |
| agcagagccg | gaggcagcta | tggctttggt | ggcgccggga | gtggatttgg tttcggtggt | 360 |
| ggagccggca | ttggctttgg | tctgggtggt | ggagccggcc | ttgctggtgg cttggggc | 420 |
| cctggcttcc | ctgtgtgccc | ccctggaggc | atccaagagg | tcaccgtcaa ccagagtctc | 480 |
| ctgactcccc | tcaacctgca | aattgacccc | gccatccagc | gggtgcgggc cgaggagcgt | 540 |
| gagcagatca | agaccctcaa | caacaagttt | gcctccttca | tcgacaaggt gcggttccta | 600 |
| gagcagcaga | acaaggttct | ggacaccaag | tggacccctgc | tgcaggagca gggcaccaag | 660 |
| actgtgaggc | agaacctgga | gccgttgttc | gagcagtaca | tcaacaacct caggaggcag | 720 |
| ctggacagca | tcgtcgggga | acggggccgc | ctggactcgg | agctgagaaa catgcaggac | 780 |
| ctggtggagg | acctcaagaa | caaatatgag | gatgaaatca | caagcgcac agcagcagag | 840 |
| aatgaatttg | tgactctgaa | gaaggatgtg | gatgctgcct | acatgaacaa ggttgaactg | 900 |
| caagccaagg | cagacactct | cacagatgag | atcaacttcc | tgagagcctt gtatgatgca | 960 |
| gagctgtccc | agatgcagac | ccacatctca | gacacatccg | tggtgctatc catggacaac | 1020 |
| aaccgcaacc | tggacctgga | cagcatcatc | gctgaggtca | aggcccaata cgaggagatt | 1080 |
| gctcagagga | gccgggctga | ggctgagtcc | tggtaccaga | ccaagtacga ggagctgcag | 1140 |
| gtcacagcag | gcagacatgg | ggacgacctg | cgcaacacca | gcaggagat tgctgagatc | 1200 |
| aaccgcatga | tccagaggct | gagatctgag | atcgaccatg | tcaagaagca gtgtgccagc | 1260 |
| ctgcaggctg | ccattgctga | tgctgagcag | cgtggggaga | tggcactcaa ggatgctaag | 1320 |
| aacaagctgg | aagggctgga | ggatgccctg | cagaaggcca | gcaggacct ggcccggctg | 1380 |
| ctgaaggagt | accaggagct | gatgaatgtc | aagctggccc | tggatgtgga gatcgccacc | 1440 |
| taccgcaagc | tgctggaggg | cgaggagtgc | aggctgaatg | gcgaaggcgt tggacaagtc | 1500 |
| aacgtctctg | tagtacagtc | caccatctcc | agtggctatg | gcggtgccag cggtgtcggc | 1560 |
| agtggcttag | gctgggtgg | aggaagcagc | tactcctatg | gcagtggtct tggcattgga | 1620 |
| ggtggcttca | gttccagcag | tggcagagcc | attgggggtg | gcctcagctc tgttggaggc | 1680 |
| ggcagttcca | ccatcaagta | caccaccacc | tcctcctcca | gcaggaagag ctacaagcac | 1740 |
| taaagtgctg | cctccagctc | tcggtcccac | agtcctcagg | cccttctctg gctgcagagc | 1800 |
| cgtctcctca | ggttgcctat | cctctcctgg | cctctagtct | tccctgctct ccgaggtaga | 1860 |
| gctgggtatg | gatgcttagt | gccctcactt | ctctctgtct | atacctgccc catctgagca | 1920 |
| cccattgctc | accatcagat | caacctttga | ttttacatca | taatgtattc accaatggag | 1980 |
| cttcactttg | ttactaaatt | attaatttct | tgcctccaaa | attgttctct ctgaggctga | 2040 |
| gcattataag | aaaatgatct | ctgttccttt | tcattactga | aaatcgcctg ggcttatt | 2100 |
| cagaacaact | tccacttatt | ttccattggc | ccccaaactc | cctaagttaa agtattgtg | 2160 |
| aaccccgcc | ccgcagtatg | catggaagca | caagtgacta | gtcgtatgat gtacacagtc | 2220 |
| tttctcccctg | tgatgatttc | tctgctcttt | gctctttgta | atttctaaat aaagcaggtt | 2280 |

```
ttagaataaa aaaaaaaaaa aaaaaaaaaa aaaaaaaaaa aaaaaaaaaa aaaaaaaaaa    2340
aaaaa                                                                 2345

<210> SEQ ID NO 2
<211> LENGTH: 2450
<212> TYPE: DNA
<213> ORGANISM: Homo sapiens
<300> PUBLICATION INFORMATION:
<308> DATABASE ACCESSION NUMBER: NM_005554
<309> DATABASE ENTRY DATE: 2009-11-22
<313> RELEVANT RESIDUES IN SEQ ID NO: (1)..(2450)

<400> SEQUENCE: 2
atatttcata cctttctaga aactgggtgt gatctcactg ttggtaaagc ccagcccttc      60
ccaacctgca agctcacctt ccaggactgg gcccagccca tgctctccat atataagctg    120
ctgccccgag cctgattcct agtcctgctt ctcttccctc tcctccag cctctcacac      180 tctcctcagc tctctcatct cctggaacca tggccagcac atccaccacc atcaggagcc    240
acagcagcag ccgccggggt ttcagtgcca actcagccag gctccctggg gtcagccgct    300
ctggcttcag cagcgtctcc gtgtcccgct ccaggggcag tggtggcctg ggtggtgcat    360
gtggaggagc tggctttggc agccgcagtc tgtatggcct gggggctcc aagaggatct     420 ccattggagg gggcagctgt gccatcagtg gcggctatgg cagcagagcc ggaggcagct    480
atggctttgg tggcgccggg agtggatttg gtttcggtgg tggagccggc attggctttg    540
gtctgggtgg tggagccggc cttgctggtg gctttggggg ccctggcttc cctgtgtgcc    600
cccctggagg catccaagag gtcaccgtca accagagtct cctgactccc ctcaacctgc    660
aaatcgatcc caccatccag cgggtgcggg ctgaggagcg tgaacagatc aagaccctca    720
acaacaagtt tgcctccttc atcgacaagg tgcggttcct ggagcagcag aacaaggttc    780
tggaaacaaa gtggaccctg ctgcaggagc agggcaccaa gactgtgagg cagaacctgg    840
agccgttgtt cgagcagtac atcaacaacc tcaggaggca gctggacagc attgtcgggg    900
aacggggccg cctggactca gagctcagag catgcagga cctggtggag gacttcaaga    960
acaaatatga ggatgaaatc aacaagcgca cagcagcaga gaatgaattt gtgactctga   1020
agaaggatgt ggatgctgcc tacatgaaca aggttgaact gcaagccaag gcagacactc   1080
tcacagacga gatcaacttc ctgagagcct tgtatgatgc agagctgtcc cagatgcaga   1140
cccacatctc agacacatct gtggtgctgt ccatggacaa caaccgcaac ctggacctgg   1200
acagcatcat cgctgaggtc aaggcccaat atgaggagat tgctcagaga agccgggctg   1260
aggctgagtc ctggtaccag accaagtacg aggagctgca ggtcacagca ggcagacatg   1320
gggacgacct cgcgcaacacc aagcaggaga ttgctgagat caaccgcatg atccagaggc   1380
tgagatctga gatcgaccac gtcaagaagc agtgcgccaa cctgcaggcc gccattgctg   1440
atgctgagca gcgtggggag atggcccctca aggatgccaa gaacaagctg gaagggctgg   1500
aggatgccct gcagaaggcc aagcaggacc tggcccggct gctgaaggag taccaggagc   1560
tgatgaatgt caagctggcc ctggacgtgg agatcgccac ctaccgcaag ctgctggagg   1620
gtgaggagtg caggctgaat ggcgaaggcg ttggacaagt caacatctct gtggtgcagt   1680
ccaccgtctc cagtggctat ggcggtgcca gtggtgtcgg cagtggctta ggcctgggtg   1740
gaggaagcag ctactcctat ggcagtggtc ttggcgttgg aggtggcttc agttccagca   1800
gtggcagagc cattgggggt ggcctcagct ctgttggagg cggcagttcc accatcaagt   1860
acaccaccac ctcctcctcc agcaggaaga gctataagca ctaaagtgcg tctgctagct   1920
```

```
ctcggtccca cagtcctcag gcccctctct ggctgcagag ccctctcctc aggttgcctt    1980
tcctctcctg gcctccagtc tccctgctgt tcccaggtag agctgggtat ggatgcttag    2040
tgccctcact tcttctctct ctctctatac catctgagca cccattgctc accatcagat    2100
caacctctga ttttacatca tgatgtaatc accactggag cttcactgtt actaaattat    2160
taatttcttg cctccagtgt tctatctctg aggctgagca ttataagaaa atgacctctg    2220
ctccttttca ttgcagaaaa ttgccagggg cttatttcag aacaacttcc acttactttc    2280
cactggctct caaactctct aacttataag tgttgtgaac ccccacccag gcagtatcca    2340
tgaaagcaca agtgactagt cctatgatgt acaaagcctg tatctctgtg atgatttctg    2400
tgctcttcgc tgtttgcaat tgctaaataa agcagattta taatacaata               2450
```

<210> SEQ ID NO 3
<211> LENGTH: 641
<212> TYPE: DNA
<213> ORGANISM: Homo sapiens
<300> PUBLICATION INFORMATION:
<308> DATABASE ACCESSION NUMBER: NM_003125
<309> DATABASE ENTRY DATE: 2009-09-20
<313> RELEVANT RESIDUES IN SEQ ID NO: (1)..(641)

<400> SEQUENCE: 3

```
accagttcta agggaccata cagagtattc ctctcttcac accaggacca gtcactgttg     60
cagcatgagt tcccagcagc agaagcagcc ttgcacccca cccctcagc ttcagcagca     120 gcaggtgaaa cagccttgcc agcctccacc tcaggaacca tgcatcccca aaaccaagga    180
gccctgccac cccaaggtgc ctgagccctg ccaccccaaa gtgcccgagc cctgccagcc    240
caaggttcca gagccatgcc accccaaggt gcctgagccc tgcccttcaa tagtcactcc    300
agcaccagcc cagcagaaga ccaagcagaa gtaatgtggt ccacagccat gcccttgagg    360
agccggccac cagatgctga atcccctatc ccattctgcg tatgagtccc atttgccttg    420
caattagcat tctgtctccc ccaaaaaaga atgtgctatg aagctttctt tcctacacac    480
tctgagtctc tgaatgaagc tgaaggtctt agtaccagag ctagttttca gctgctcaga    540
attcatctga agagagactt aagatgaaag caaatgattc agctccctta tacccccatt    600
aaattcactt tcaattccaa aaaaaaaaaa aaaaaaaaa a                         641
```

<210> SEQ ID NO 4
<211> LENGTH: 2451
<212> TYPE: DNA
<213> ORGANISM: Homo sapiens
<300> PUBLICATION INFORMATION:
<308> DATABASE ACCESSION NUMBER: NM_006121
<309> DATABASE ENTRY DATE: 2009-09-20
<313> RELEVANT RESIDUES IN SEQ ID NO: (1)..(2451)

<400> SEQUENCE: 4

```
agaggagtgt ttagctcctt ccctactct accttgctcc tacttttctc taagtcaaca     60
tgagtcgaca gtttagttcc aggtctgggt accgaagtgg aggggcttc agctctggct     120 ctgctgggat catcaactac cagcgcagga ccaccagcag ctccacacgc cgcagtggag    180
gaggtggtgg gagattttca agctgtggtg gtggtggtgg tagctttggt gctggtggtg    240
gatttggaag tcggagtctt gttaaccttg gtggcagtaa aagcatctcc ataagtgtgg    300
ctagaggagg tggacgtggt agtggctttg gtggtggtta tggtggtggt ggcttttggtg    360 gtggtggctt tggtggtggt ggctttggtg gaggtggcat tggggtggt ggctttggtg    420 gttttggcag tggtggtggt ggttttggtg gaggtggctt tggggggtggt ggatatgggg    480
```

```
gtggttatgg tcctgtctgc cctcctggtg gcatacaaga agtcactatc aaccagagcc    540
ttcttcagcc cctcaatgtg gagattgacc ctgagatcca aaaggtgaag tctcgagaaa    600
gggagcaaat caagtcactc aacaaccaat ttgcctcctt cattgacaag gtgaggttcc    660
tggagcagca gaaccaggta ctgcaaacaa aatgggagct gctgcagcag gtagatacct    720
ccactagaac cctaaattta gagccctact ttgagtcatt catcaacaat ctccgaagga    780
gagtggacca actgaagagt gatcaatctc ggttggattc ggaactgaag aacatgcagg    840
acatggtgga ggattaccgg aacaagtatg aggatgaaat caacaagcgg acaaatgcag    900
agaatgaatt tgtgaccatc aagaaggatg tggatggtgc ttatatgacc aaggtggacc    960
ttcaggccaa acttgacaac ttgcagcagg aaattgattt ccttacagca ctctaccaag   1020
cagagttgtc tcagatgcag actcaaatca gtgaaactaa tgtcatcctc tctatggaca   1080
acaaccgcag tctcgacctg gacagcatca ttgctgaggt caaggcccag tacgaggata   1140
tagcccagaa gagcaaagct gaggccgagt ccttgtacca gagcaagtat gaagagctgc   1200
agatcactgc tggcagacat ggggatagtg tgagaaattc aaagatagaa atttctgagc   1260
tgaatcgtgt gatccagaga cttagatctg aaatcgacaa tgtcaagaag cagatctcca   1320
acttgcagca gtccatcagt gatgcagagc agcgtggcga aatgccctc aaggatgcca   1380 agaacaagct gaatgacctg gaggatgccc tgcagcaggc caaggaagac ctggcccgcc   1440
tgctgcgcga ctaccaggag ctgatgaaca ccaagctggc cctggatctg gagattgcca   1500
cctacaggac cctcctggag ggagaagaaa gcaggatgtc tggagaatgt gccccgaacg   1560
tgagtgtgtc tgtgagcaca agccacacca ccatcagtgg aggtggcagc cgaggaggtg   1620
gcggcggtgg ctacggctct ggaggtagca gctatggctc cggaggtggt agctatggtt   1680
ctggaggtgg cggcggcggc ggccgtggca gctatgctc cggaggtagc agctacggct   1740
ccggaggtgg cagctatggc tctgaggtg gcggcggcgg ccatggcagc tacggctccg   1800
gaagcagcag tgggggctac agaggtgct ctggaggcgg cggcggcggc agctctggcg   1860 gccgggctc tggcggcggg agctctggag gctccatagg aggccgggga tccagctctg   1920
ggggtgtcaa gtcctctggt ggcagttcca gcgtgaagtt tgtttctacc acttattccg   1980
gagtaaccag ataaagagat gccctctgtt tcattagctc tagttctccc ccagcatcac   2040
taacaaatat gcttggcaag accgaggtcg atttgtccca gccttaccgg agaaaagagc   2100
tatggttagt tacactagct catcctattc ccccagctct ttcttttctg ctgtttccca   2160
atgaagtttt cagatcagtg gcaatctcag tccctggct atgaccctgc tttgttcttt   2220
ccctgagaaa cagttcagca gtgaccacca cccacatgac atttcaaagc acctccttaa   2280
gccagccaga gtaggaccag ttagacccag ggtgtggaca gctccttagc atcttatctc   2340
tgtgctgttt tggttttgta cataaggtgt aagcaagttg ttttctttt gtggagaggt   2400 cttaaactcc ccatttcctt gttttgctgc aataaactgc atttgaaatt c           2451
```

<210> SEQ ID NO 5
<211> LENGTH: 762
<212> TYPE: DNA
<213> ORGANISM: Homo sapiens
<300> PUBLICATION INFORMATION:
<308> DATABASE ACCESSION NUMBER: NM_001024209.2
<309> DATABASE ENTRY DATE: 2007-06-26
<313> RELEVANT RESIDUES IN SEQ ID NO: (1)..(762)

<400> SEQUENCE: 5

```
aaactcctgg tacttgagca ctgatctgct ttggagaacc tgattctgag actccagcag     60
```

-continued

| | |
|---|---|
| gatgtcttat caacagcagc agtgcaagca gccctgccag ccacctcctg tgtgccccac | 120 |
| gccaaagtgc ccagagccat gtccaccccc gaagtgccct gagccctgcc caccaccaaa | 180 |
| gtgtccacag ccctgcccac ctcagcagtg ccagcaaaaa tgtcctcctg tgacaccttc | 240 |
| cccaccctgc cagccaaagt gtccacccaa gagcaagtaa cagcttcaga attcatcagg | 300 |
| agcatgaaag gataaggata attggctcac cttgttccac agcttcacct gcatcttctc | 360 |
| atcaaagcct accatggata cacagttagc ttctttcctc ttagccagtg atctgcccat | 420 |
| gatgatccct gatagcaaaa ggtttccttt ctgaggctgc catattgcca ctgtccaggt | 480 |
| ggagactgag aaaggaagtc ctcagcagtg tcagttccca gagctttgga agaaggacca | 540 |
| gcagctctgt ccctgggaac catcaaaaaa tgctgttgat gttttctgtg tctgtctgtc | 600 |
| acctgggcat gggcttctaa cacctgtgca attgtcactt ttctttcact ccctgaataa | 660 |
| aatatctttg catacgtaaa aaaaaaaaaa aaaaaaaaaa aaaaaaaaaa aaaaaaaaaa | 720 |
| aaaaaaaaaa aaaaaaaaaa aaaaaaaaaa aaaaaaaaaa aa | 762 |

<210> SEQ ID NO 6
<211> LENGTH: 2053
<212> TYPE: DNA
<213> ORGANISM: Homo sapiens
<300> PUBLICATION INFORMATION:
<308> DATABASE ACCESSION NUMBER: NM_001630
<309> DATABASE ENTRY DATE: 2008-08-07
<313> RELEVANT RESIDUES IN SEQ ID NO: (1)..(2053)

<400> SEQUENCE: 6

| | |
|---|---|
| aaagccaggc agagcccggg ggcgaggggg cggcaggcag gtgtagcgct gccctgggcg | 60 |
| ggcttgcacc cccacaccca agtgagcggc ctgctcactc ctcagctgca ggagccagac | 120 |
| gtgtggagtc ccagcagagg ccaacctgtg tctcttcatc tccgtgagaa aggtgccccc | 180 |
| gaagtgaaag agatggcctg gtggaaagcc tggattgaac aggagggtgt cacagtgaag | 240 |
| agcagctccc acttcaaccc agaccctgat gcagagaccc tctacaaagc catgaagggg | 300 |
| atcgggacca acgagcaggc tatcatcgat gtgctcacca agagaagcaa cacgcagcgg | 360 |
| cagcagatcg ccaagtcctt caaggctcag ttcggcaagg acctcactga gaccttgaag | 420 |
| tctgagctca gtggcaagtt tgagaggctc attgtggccc ttatgtaccc gccatacaga | 480 |
| tacgaagcca aggagctgca tgacgccatg aagggcttag gaaccaagga gggtgtcatc | 540 |
| attgagatcc tggcctctcg gaccaagaac cagctgcggg agataatgaa ggcgtatgag | 600 |
| gaagactatg gtccagcct ggaggaggac atccaagcag acacaagtgg ctacctggag | 660 |
| aggatcctgg tgtgcctcct gcagggcagc agggatgatg tgagcagctt tgtggacccg | 720 |
| gcactggccc tccaagacgc acaggatctg tatgcggcag cgagaatat tcgtgggact | 780 |
| gatgagatga aattcatcac catcctgtgc acgcgcagtg ccactcacct gctgagagtg | 840 |
| tttgaagagt atgagaaaat tgccaacaag agcattgagg acagcatcaa gagtgagacc | 900 |
| catggctcac tggaggaggc catgctcact gtggtgaaat gcacccaaaa cctccacagc | 960 |
| tactttgcag agagactcta ctatgccatg aagggagcag gacgcgtga tgggaccctg | 1020 |
| ataagaaaca tcgtttcaag gagcgagatt gacttaaatc ttatcaaatg tcacttcaag | 1080 |
| aagatgtacg gcaagaccct cagcagcatg atcatggaag acaccagcgg tgactacaag | 1140 |
| aacgccctgc tgagcctggt gggcagcgac ccctgaggca cagaagaaca agagcaaaga | 1200 |
| ccatgaagcc agagtctcca ggactcctca ctcaacctcg gccatggacg caggttgggt | 1260 |
| gtgagggggg tcccagcctt tcggtcttct atttccctat ttccagtgct ttccagccgg | 1320 |

```
gtttctgacc cagagggtgg aaccggcctg gactcctctt cccaacttcc tccaggtcat    1380
ttcccagtgt gagcacaatg ccaaccttag tgtttctcca gccagacaga tgcctcagca    1440
tgaagggctt ggggacttgt ggatcattcc ttcctccctg caggagcttc ccaagctggt    1500
cacagagtct cctgggcaca ggttatacag accccagccc cattcccatc tactgaaaca    1560
gggtctccac aagaggggcc agggaatatg gttttttaac aagcgtctta caaaacactt    1620
ctctatcatg cagccggaga gctggctggg agccttttg ttttagaaca cacatccttc     1680
agcagctgag aaacgaacac gaatccatcc caaccgagat gccattaaca ttcatctaaa    1740
aatgttaggc tctaaatgga cgaaaaattc tctcgccatc ttaataacaa aataaactac    1800
aaattcctga cccaaggaca ctgtgttata agaggcgtgg gctcccctgg tggctgacca    1860
ggtcagctgc cctggccttg caccnctctg catgcagcac agaagggtgt gaccatgccc    1920
tcagcaccac tcttgtcccc actgaacggc aactgagact gggtacctgg agattctgaa    1980
gtgcctttgc tgtggttttc aaataataa agatttgtat tcaactcaaa aaaaaaaaa     2040 aaaaaaaaaa aaa                                                      2053

<210> SEQ ID NO 7
<211> LENGTH: 515
<212> TYPE: DNA
<213> ORGANISM: Homo sapiens
<300> PUBLICATION INFORMATION:
<308> DATABASE ACCESSION NUMBER: NM_002307
<309> DATABASE ENTRY DATE: 2009-09-13
<313> RELEVANT RESIDUES IN SEQ ID NO: (1)..(515)

<400> SEQUENCE: 7
acggctgccc aacccggtcc cagccatgtc caacgtcccc cacaagtcct cactgcccga    60
gggcatccgc cctggcacgg tgctgagaat tcgcggcttg gttcctccca atgccagcag    120
gttccatgta aacctgctgt gcggggagga gcagggctcc gatgccgcgc tgcatttcaa    180 ccccccggctg gacacgtcgg aggtggtctt caacagcaag gagcaaggct cctggggccg    240
cgaggagcgc gggccggggcg ttcctttcca gcgcgggcag cccttcgagg tgctcatcat    300
cgcgtcagac gacggcttca aggccgtggt tggggacgcc cagtaccacc acttccgcca    360
ccgcctgccg ctggcgcgcg tgcgcctggt ggaggtgggc ggggacgtgc agctggactc    420
cgtgaggatc ttctgagcag aagcccaggc ggggcccgggg ccttggctgg caaataaagc    480
gttagcccgc agcgaaaaaa aaaaaaaaaa aaaaa                              515

<210> SEQ ID NO 8
<211> LENGTH: 410
<212> TYPE: DNA
<213> ORGANISM: Homo sapiens

<400> SEQUENCE: 8
gtccagcatc ctttgaagca tgagttccca caagcagaag cagcccttta cctcaccccc    60
tcagcttcaa cagcagcagg tgaaacagca cagccagcct ctcccttagg aaccatttgt    120
tcccataacc aaggagccat gctacccaaa acttggaacc tggaacctgg aaacaccaag    180
attccagagt taggctgcac caagatccct gagccaggct gcaccaaggt ccttgagtca    240
atctccacca aggtaccaga gccacatcct tcaacagtca cttccggccc agctcagcag    300
aagtccaagt agaagtaatg tggtgcacag acaagcccttt gagaagctga ccaccagatg    360
ctggacacac tcttcctatc tgcttctgta tcttaattgt ctgtagacct                410

<210> SEQ ID NO 9
```

<211> LENGTH: 5561
<212> TYPE: DNA
<213> ORGANISM: Homo sapiens
<300> PUBLICATION INFORMATION:
<308> DATABASE ACCESSION NUMBER: NM_001944
<309> DATABASE ENTRY DATE: 2009-07-26
<313> RELEVANT RESIDUES IN SEQ ID NO: (1)..(5561)

<400> SEQUENCE: 9

| | | | | | |
|---|---|---|---|---|---|
| aaagcagcag | agacgctgca | gagggctttt | cttagacatc | aactgcagac | ggctggcagg | 60 |
| atagaagcag | cggctcactt | ggactttttc | accagggaaa | tcagagacaa | tgatggggct | 120 |
| cttcccaga | actacagggg | ctctggccat | cttcgtggtg | gtcatattgg | ttcatggaga | 180 |
| attgcgaata | gagactaaag | gtcaatatga | tgaagaagag | atgactatgc | aacaagctaa | 240 |
| aagaaggcaa | aaacgtgaat | gggtgaaatt | tgccaaaccc | tgcagagaag | gagaagataa | 300 |
| ctcaaaaaga | aacccaattg | ccaagattac | ttcagattac | caagcaaccc | agaaaatcac | 360 |
| ctaccgaatc | tctggagtgg | gaatcgatca | gccgcctttt | ggaatctttg | ttgttgacaa | 420 |
| aaacactgga | gatattaaca | taacagctat | agtcgaccgg | gaggaaactc | caagcttcct | 480 |
| gatcacatgt | cgggctctaa | atgcccaagg | actagatgta | gagaaaccac | ttatactaac | 540 |
| ggttaaaatt | ttggatatta | atgataatcc | tccagtattt | tcacaacaaa | ttttcatggg | 600 |
| tgaaattgaa | gaaatagtg | cctcaaactc | actggtgatg | atactaaatg | ccacagatgc | 660 |
| agatgaacca | aaccacttga | attctaaaat | tgccttcaaa | attgtctctc | aggaaccagc | 720 |
| aggcacaccc | atgttcctcc | taagcagaaa | cactggggaa | gtccgtactt | tgaccaattc | 780 |
| tcttgaccga | gagcaagcta | gcagctatcg | tctggttgtg | agtggtgcag | acaaagatgg | 840 |
| agaaggacta | tcaactcaat | gtgaatgtaa | tattaaagtg | aaagatgtca | cgataacttt | 900 |
| cccaatgttt | agagactctc | agtattcagc | acgtattgaa | gaaaatattt | taagttctga | 960 |
| attacttcga | tttcaagtaa | cagatttgga | tgaagagtac | acagataatt | ggcttgcagt | 1020 |
| atatttcttt | acctctggga | atgaaggaaa | ttggttgaa | atacaaactg | atcctagaac | 1080 |
| taatgaaggc | atcctgaaag | tggtgaaggc | tctagattat | gaacaactac | aaagcgtgaa | 1140 |
| acttagtatt | gctgtcaaaa | acaaagctga | atttcaccaa | tcagttatct | ctcgataccg | 1200 |
| agttcagtca | accccagtca | caattcaggt | aataaatgta | agagaaggaa | ttgcattccg | 1260 |
| tcctgcttcc | aagacattta | ctgtgcaaaa | aggcataagt | agcaaaaaat | tggtggatta | 1320 |
| tatcctggga | acatatcaag | ccatcgatga | ggacactaac | aaagctgcct | caaatgtcaa | 1380 |
| atatgtcatg | ggacgtaacg | atggtggata | cctaatgatt | gattcaaaaa | ctgctgaaat | 1440 |
| caaatttgtc | aaaaatatga | accgagattc | tactttcata | gttaacaaaa | caatcacagc | 1500 |
| tgaggttctg | gccatagatg | aatacacggg | taaaacttct | acaggcacgg | tatatgttag | 1560 |
| agtacccgat | ttcaatgaca | attgtccaac | agctgtcctc | gaaaaagatg | cagtttgcag | 1620 |
| ttcttcacct | tccgtggttg | tctccgctag | aacactgaat | aatagataca | ctggcccta | 1680 |
| tacatttgca | ctggaagatc | aacctgtaaa | gttgcctgcc | gtatggagta | tcacaaccct | 1740 |
| caatgctacc | tcggccctcc | tcagagccca | ggaacagata | cctcctggag | tataccacat | 1800 |
| ctccctggta | cttacagaca | gtcagaacaa | tcggtgtgag | atgccacgca | gcttgacact | 1860 |
| ggaagtctgt | cagtgtgaca | acaggggcat | ctgtggaact | tcttacccaa | ccacaagccc | 1920 |
| tgggaccagg | tatggcaggc | cgcactcagg | gaggctgggg | cctgccgcca | tcggcctgct | 1980 |
| gctccttggt | ctcctgctgc | tgctgttggc | ccccctctg | ctgttgacct | gtgactgtgg | 2040 |
| ggcaggttct | actggggag | tgacaggtgg | ttttatccca | gttcctgatg | gctcagaagg | 2100 |

```
aacaattcat cagtggggaa ttgaaggagc ccatcctgaa gacaaggaaa tcacaaatat    2160
ttgtgtgcct cctgtaacag ccaatggagc cgatttcatg gaaagttctg aagtttgtac    2220
aaatacgtat gccagaggca cagcggtgga aggcacttca ggaatggaaa tgaccactaa    2280
gcttggagca gccactgaat ctggaggtgc tgcaggcttt gcaacaggga cagtgtcagg    2340
agctgcttca ggattcggag cagccactgg agttggcatc tgttcctcag gcagtctgg     2400
aaccatgaga acaaggcatt ccactggagg aaccaataag gactacgctg atggggcgat    2460
aagcatgaat tttctggact cctactttc tcagaaagca tttgcctgtg cggaggaaga     2520
cgatggccag gaagcaaatg actgcttgtt gatctatgat aatgaaggcg cagatgccac    2580
tggttctcct gtgggctccg tgggttgttg cagttttatt gctgatgacc tggatgacag    2640
cttcttggac tcacttggac ccaaatttaa aaaacttgca gagataagcc ttggtgttga    2700
tggtgaaggc aaagaagttc agccaccctc taaagacagc ggttatggga ttgaatcctg    2760
tggccatccc atagaagtcc agcagacagg atttgttaag tgccagactt tgtcaggaag    2820
tcaaggagct tctgctttgt ccacctctgg gtctgtccag ccagctgttt ccatccctga    2880
ccctctgcag catggtaact atttagtaac ggagacttac tcggcttctg gttccctcgt    2940
gcaaccttcc actgcaggct ttgatccact tctcacacaa aatgtgatag tgacagaaag    3000
ggtgatctgt cccatttcca gtgttcctgg caacctagct ggcccaacgc agctacgagg    3060
gtcacatact atgctctgta cagaggatcc ttgctcccgt ctaatatgac cagaatgagc    3120
tggaatacca cactgaccaa atctggatct ttggactaaa gtattcaaaa tagcatagca    3180
aagctcactg tattgggcta ataatttggc acttattagc ttctctcata aactgatcac    3240
gattataaat taaatgtttg ggttcatacc ccaaaagcaa tatgttgtca ctcctaattc    3300
tcaagtacta ttcaaattgt agtaaatctt aaagttttc aaaaccctaa aatcatattc     3360
gccaggaaat tttcctaaac attcttaagc ttctatttt ccctgccaa aggaaggtgt      3420
ttatcatttt aaaatgcaat gtgatttagt ggattaagca ggagcgctgg ttcttgtctc    3480
cattgccttt tcttatatca ttgataatga tgtaagaatc acaaggggcc gggcgcggtg    3540
gctcacgcct gtaatcccag cactttggga ggccgaggca ggtggatcat gaggtcagga    3600
gatcgagacc atcctggcta caaggtgaa accccgtctc tactaaaaat acaaaaaatt      3660
agccgggcgc agtggcgggc gcctgtagtc ccagctactc gggaggctga ggcaggagaa    3720
tggcatgaac ccgggaagcg gagcttgcag tgagccgaga ttgcgccact gcagtccgca    3780
gtccggcctg ggcgacagag cgagactccg tctcaaaaaa aaaaaaaaa aagaatcac       3840
aaggtatttg ctaaagcatt tgagctgct tggaaaaagg gaagtagttg cagtagagtt      3900
tcttccatct tcttggtgct gggaagccat atatgtgtct tttactcaag ctaagggta     3960
taagcttatg tgttgaattt gctacatcta tatttcacat attctcacaa taagagaatt    4020
ttgaaataga aatatcatag aacatttaag aaagtttagt ataaataata ttttgtgtgt    4080
tttaatccct ttgaagggat ctatccaaag aaaatatttt acactgagct ccttcctaca    4140
cgtctcagta acagatcctg tgttagtctt tgaaaatagc tcatttttta aatgtcagtg    4200
agtagatgta gcatacatat gatgtataat gacgtgtatt atgttaacaa tgtctgcaga    4260
ttttgtagga atacaaaaca tggccttttt tataagcaaa acgggccaat gactagaata    4320
acacataggg caatctgtga atatgtatta taagcagcat tccagaaaag tagttggtga    4380
aataattttc aagtcaaaaa gggatatgga aagggaatta tgagtaacct ctatttttta    4440
agccttgctt ttaaattaaa cagctacagc catttaagcc ttgaggataa taaagcttga    4500
```

-continued

```
gagtaataat gttaggttag caaaggttta gatgtatcac ttcatgcatg ctaccatgat      4560
agtaatgcag ctcttcgagt catttctggt cattcaagat attcacccct ttgcccatag      4620
aaagcaccct acctcacctg cttactgaca ttgtcttagc tgatcacaag atcattatca      4680
gcctccatta ttccttactg tatataaaat acagagtttt atattttcct ttcttcgttt      4740
ttcaccatat tcaaaaccta aatttgtttt tgcagatgga atgcaaagta atcaagtgtt      4800
tgtgctttca cctagaaggg tgtggtcctg aaggaaagag gtcccctaaa tatcccccac      4860
cctggtgctc ctccctctcc ctggtaccct gactaccagg aagtcaggtg ctagagcagc      4920
tggagaagtg caggcagcct gtgcttccac agatgggggt gctgctgcaa caaggctttc      4980
aatgtgccca tcttaggtgg gagaagctag atcctgtgca gcagcctggt aagtcctgag      5040
gaggttccat tgctcttcct gctgctgtcc tttgcttctc aacggtggct cgctctacag      5100
tctagagcac atgcagctaa cttgtgcctc tgcttatgca tgagggttaa attaacaacc      5160
ataaccttca tttgaagttc aaaggtgtat tcaggatcct caaagcattt taaccttgcc      5220
gcttaaaacc caatttaccg tgaaatggga attttgctgc attgttaaac tgtagtggaa      5280
accatgctat agtaataaag gttatataag agagaaattg aaattaaatg tgttttttaaa     5340 tttcaaaaaa aaatcaatct ttaggatgac ttaaaaattg atttgccatg taaaatgtat      5400 ctgcatttt tacacaaaac ttgttttaag cataaaattt taaaactgta ctacttgatg        5460
tattatacat tttgaaccat atgtattaaa ccataaacag tataatgttg ttataataaa     5520
acaggcaata aatttataaa taaaagctga aaaaaaaaa a                           5561
```

<210> SEQ ID NO 10
<211> LENGTH: 657
<212> TYPE: DNA
<213> ORGANISM: Homo sapiens
<300> PUBLICATION INFORMATION:
<308> DATABASE ACCESSION NUMBER: NM_001014450.1
<309> DATABASE ENTRY DATE: 2009-05-17
<313> RELEVANT RESIDUES IN SEQ ID NO: (1)..(657)

<400> SEQUENCE: 10

```
actcctggta cctaagcacc gatctgcctt ggagaacctg attctgagac tccagcagga       60
tgtcttatca acagcagcag tgcaagcagc cctgccagcc acctcctgtg tgccccgcgc      120
caaagtgccc agagccatgt ccacccccga agtgccctga gccctgccca ccatcaaagt      180
gtccacagtc ctgcccacct cagcagtgcc agcagaaatg tcctcctgtg cacccttccc      240 cacccctgcca gccaaagtgt ccacccaaga gcaagtaaca gcttcaggat tcatcaggag      300
catgaaagga taaggataat tggctcacct cgttccacag ctccacctgc atcttctcat      360
caaagccatc cagggataca cagggagctt ctttcctctt agcctgtgat cggcctgtga      420
tgatctctga tagcaaaagg ttttctttt gaggctgcca tactgccact gtcgaggtgg       480
agactgagca aaggaagtcc tgggctgtgc cagctcccag agcttcagaa gaaagagcag      540
ctctctccct gggaaccatt agagaattct gttgatgttt tctgtgtctg tctgtcccct      600
gggcatgagc ttccaccacc tgtgcagttg tcactttcct ttcactccct gaataaa        657
```

<210> SEQ ID NO 11
<211> LENGTH: 1219
<212> TYPE: DNA
<213> ORGANISM: Homo sapiens
<300> PUBLICATION INFORMATION:
<308> DATABASE ACCESSION NUMBER: NM_005130
<309> DATABASE ENTRY DATE: 2009-11-01
<313> RELEVANT RESIDUES IN SEQ ID NO: (1)..(1219)

```
<400> SEQUENCE: 11
gaatagtcta ccccccttgc actctacctg acacagctgc agcctgcaat tcactcgcac      60
tgcctgggat tgcactggat ccgtgtgctc agaacaaggt gaacgcccag ctgcagccat     120
gaagatctgt agcctcaccc tgctctcctt cctcctactg gctgctcagg tgctcctggt     180
ggagggaaaa aaaaaagtga agaatggact tcacagcaaa gtggtctcag aacaaaagga     240
cactctgggc aacacccaga ttaagcagaa aagcaggccc gggaacaaag caagtttgt      300 caccaaagac caagccaact gcagatgggc tgctactgag caggaggagg gcatctctct     360
caaggttgag tgcactcaat tggaccatga attttcctgt gtctttgctg caatccaac      420 ctcatgccta aagctcaagg atgagagagt ctattggaaa caagttgccc ggaatctgcg     480
ctcacagaaa gacatctgta gatattccaa gacagctgtg aaaccagag tgtgcagaaa      540 ggattttcca gaatccagtc ttaagctagt cagctccact ctatttggga acacaaagcc     600
caggaaggag aaaacagaga tgtccccag ggagcacatc aaaggcaaag agaccacccc      660
ctctagccta gcagtgaccc agaccatggc caccaaagct cccgagtgtg tggaggaccc     720
agatatggca aaccagagga agactgcccct ggagttctgt ggagagactt ggagctctct    780
ctgcacattc ttcctcagca tagtgcagga cacgtcatgc taatgaggtc aaaagagaac     840 gggttcccctt aagagatgtc atgtcgtaag tccctctgta tactttaaag ctctctacag     900
tccccccaaa atatgaactt tgtgcttag tgagtgcaac gaaatattta acaagtttt      960 gtatttttg cttttgtgtt ttggaatttg ccttattttt cttggatgcg atgttcagag    1020
gctgtttcct gcagcatgta tttccatggc ccacacagct atgtgtttga gcagcgaaga    1080
gtctttgagc tgaatgagcc agagtgataa tttcagtgca acgaactttc tgctgaatta    1140
atggtaataa aactctgggt gtttttcaga aatacattca aaaaaaaaa aaaaaaaaa      1200 aaaaaaaaaa aaaaaaaaa                                               1219

<210> SEQ ID NO 12
<211> LENGTH: 312
<212> TYPE: DNA
<213> ORGANISM: Homo sapiens

<400> SEQUENCE: 12
atgccctgtt cttctgcact tccctggctt cctgtgttgg ttctgctggt gtcacctgct      60
tttgggttta cgtggcttcc cagcttccta atttctctga agttgagttt gatgtttcat     120
gccatggagg aagtggtgaa ggaggtggtg ggacatgcca aggagactgg agagaaagcc     180
attgccgaag ccataaagaa agcccaagag tcagggggaca aaaagatgaa ggaagtcact     240
gagacagtga ccaacacagt cacaaatgcc atcacccatg cagcagagag tctgggcaaa     300
cttggacagt ga                                                        312

<210> SEQ ID NO 13
<211> LENGTH: 510
<212> TYPE: DNA
<213> ORGANISM: Homo sapiens
<300> PUBLICATION INFORMATION:
<308> DATABASE ACCESSION NUMBER: NM_005980
<309> DATABASE ENTRY DATE: 2009-09-20
<313> RELEVANT RESIDUES IN SEQ ID NO: (1)..(510)

<400> SEQUENCE: 13
tgaggctgcc ttataaagca ccaagaggct gccagtggga catttttctcg gccctgccag      60 cccccaggag gaaggtgggt ctgaatctag caccatgacg gaactagaga cagccatggg    120
```

-continued

| | |
|---|---|
| catgatcata gacgtctttt cccgatattc gggcagcgag ggcagcacgc agaccctgac | 180 |
| caaggggag ctcaaggtgc tgatggagaa ggagctacca ggcttcctgc agagtggaaa | 240 |
| agacaaggat gccgtggata aattgctcaa ggacctggac gccaatggag atgcccaggt | 300 |
| ggacttcagt gagttcatcg tgttcgtggc tgcaatcacg tctgcctgtc acaagtactt | 360 |
| tgagaaggca ggactcaaat gatgccctgg agatgtcaca gattcctggc agagccatgg | 420 |
| tcccaggctt cccaaaagtg tttgttggca attattcccc taggctgagc ctgctcatgt | 480 |
| acctctgatt aataaatgct tatgaaatga | 510 |

<210> SEQ ID NO 14
<211> LENGTH: 5190
<212> TYPE: DNA
<213> ORGANISM: Homo sapiens
<300> PUBLICATION INFORMATION:
<308> DATABASE ACCESSION NUMBER: NM_144670
<309> DATABASE ENTRY DATE: 2009-09-03
<313> RELEVANT RESIDUES IN SEQ ID NO: (1)..(5190)

<400> SEQUENCE: 14

| | |
|---|---|
| atcagtcatc actgcacacc ctacctggaa ttagtatata aagctacgcg gagcgatctc | 60 |
| tgcccctgac cctggaaaaa tctgtctcac ccacaaagat gtgggctcag ctccttctag | 120 |
| gaatgttggc cctatcacca gccattgcag aagaacttcc aaactacctg gtgacattac | 180 |
| cagcccggct aaatttcccc tccgttcaga aggtttgttt ggacctgagc cctgggtaca | 240 |
| gtgatgttaa attcacggtt actctggaga ccaaggacaa gacccagaag ttgctagaat | 300 |
| actctggact gaagaagagg cacttacatt gtatctcctt tcttgtacca cctcctgctg | 360 |
| gtggcacaga agaagtggcc acaatccggg tgtcgggagt tggaaataac atcagctttg | 420 |
| aggagaagaa aaaggttcta attcagaggc aggggaacgg cacctttgta cagactgaca | 480 |
| aacctctcta caccccaggg cagcaagtgt atttccgcat tgtcaccatg gatagcaact | 540 |
| tcgttccagt gaatgacaag tactccatgg tggaactaca ggatccaaat agcaacagga | 600 |
| ttgcacagtg gctggaagtg gtacctgagc aaggcattgt agaccctgtc cttccaactgg | 660 |
| caccagaggc aatgctgggc acctacactg tggcagtggc tgagggcaag accttttggta | 720 |
| ctttcagtgt ggaggaatat gtgctgccga gtttaaggt ggaagtggtg aacccaaggg | 780 |
| agttatcaac ggtgcaggaa tctttcttag taaaaatttg ttgtaggtac acctatggaa | 840 |
| agcccatgct aggggcagtg caggtatctg tgtgtcagaa ggcaaatact tactggtatc | 900 |
| gagaggtgga acgggaacag cttcctgaca atgcaggaa cctctctgga cagactgaca | 960 |
| aaacaggatg tttctcagca cctgtggaca tggccacctt tgacctcatt ggatatgcgt | 1020 |
| acagccatca aatcaatatt gtggctactg ttgtggagga agggacaggt gtggaggcca | 1080 |
| atgccactca gaatatctac atttctccac aaatgggatc aatgaccttt gaagacacca | 1140 |
| gcaattttta ccatccaaat ttccccttca gtggaagat aagagttagg ggccatgatg | 1200 |
| actccttcct caagaaccat ctagtgtttc tggtgattta tggcacaaat ggaaccttca | 1260 |
| accagaccct ggttactgat aacaatggcc tagctccctt taccttggag acatccggtt | 1320 |
| ggaatgggac agacgtttct ctggagggaa agtttcaaat ggaagactta gtatataatc | 1380 |
| cggaacaagt gccacgttac taccaaaatg cctacctgca cctgcgaccc ttctacagca | 1440 |
| caacccgcag cttccttggc atccaccggc taaacggccc cttgaaatgt ggccagcccc | 1500 |
| aggaagtgct ggtggattat tacatcgacc cggccgatgc aagccctgac caagagatca | 1560 |
| gcttctccta ctatttaata gggaaaggaa gtttggtgat gagggggcag aaacacctga | 1620 |

```
actctaagaa gaaaggactg aaagcctcct tctctctctc actgaccttc acttcgagac    1680
tggcccctga tccttccctg gtgatctatg ccattttcc cagtggaggt gttgtagctg     1740
acaaaattca gttctcagtc gagatgtgct tgacaatca ggtttccctt ggcttctccc    1800
cctcccagca gcttccagga gcagaagtgg agctgcagct gcaggcagct cccggatccc    1860
tgtgtgcgct ccgggcggtg gatgagagtg tcttactgct taggccagac agagagctga    1920
gcaaccgctc tgtctatggg atgtttccat tctggtatgg tcactacccc tatcaagtgg    1980
ctgagtatga tcagtgtcca gtgtctggcc catgggactt tcctcagccc ctcattgacc    2040
caatgcccca agggcattcg agccagcgtt ccattatctg gaggccctcg ttctctgaag    2100
gcacggacct tttcagcttt ttccgggacg tgggcctgaa atactgtcc aatgccaaaa     2160 tcaagaagcc agtagattgc agtcacagat ctcagaata cagcactgct atgggtgcag     2220
gcggtggtca tccagaggct tttgagtcat caactccttt acatcaagca gaggattctc    2280
aggtccgcca gtactcccca gagacctggc tctgggatct gtttcctatt ggtaactcgg    2340
ggaaggaggc ggtccacgtc acagttcctg acgccatcac cgagtggaag gcgatgagtt    2400
tctgcacttc ccagtcaaga ggcttcgggc tttcacccac tgttggacta actgctttca    2460
agccgttctt tgttgacctg actctccctt actcagtagt ccgtggggaa tcctttcgtc    2520
ttactgccac catcttcaat tacctaaagg attgcatcag ggttcagact gacctggcta    2580
aatcgcatga gtaccagcta gaatcatggg cagattctca gacctccagt tgtctctgtg    2640
ctgatgaagc aaaacccac cactggaaca tcacagctgt caaattgggt cacattaact      2700
ttactattag tacaaagatt ctggacagca atgaaccatg tgggggccag aagggtttg     2760 ttccccaaaa gggccgaagt gacacgctca tcaagccagt tctcgtcaaa cctgagggag    2820
tcctggtgga aagacacac agctcattgc tgtgcccaaa aggaaaggtg gcatctgaat    2880
ctgtctccct ggagctccca gtggacattg ttcctgactc gaccaaggct tatgttacgg    2940
ttctgggaga cattatgggc acagccctgc agaacctgga tggtctggtg cagatgccca    3000
gtggctgtgg cgagcagaac atggtcttgt ttgctcccat catctatgtc ttgcagtacc    3060
tggagaaggc agggctgctg acggaggaga tcaggtctcg ggcagtgggt ttcctggaaa    3120
tagggtacca gaaggagctg atgtacaaac acagcaatgg ctcatacagt gcctttgggg    3180
agcgagatgg aaatgaaac acatggctga cagcgtttgt cacaaaatgc tttggccaag    3240
ctcagaaatt catcttcatt gatcccaaga acatccagga tgctctcaag tggatggcag    3300
gaaaccagct cccccagtggc tgctatgcca acgtgggaaa tctccttcac acagctatga    3360
agggtggtgt tgatgatgag gtctccttga ctgcgtatgt cacagctgca ttgctggaga    3420
tgggaaagga tgtagatgac ccaatggtga gtcagggtct acggtgtctc aagaattcgg    3480
ccacctccac gaccaaccta tacacacagg ccctgttggc ttacattttc tccctggctg    3540
gggaaatgga catcagaaac attctcctta acagttagaa tcaacaggct atcatctcag    3600
gagaatccat ttactggagc cagaaaccta ctccatcatc gaacgccagc ccttggtctg    3660
agcctgcggc tgtagatgtg gaactcacag catatgcatt gttggcccag cttaccaagc    3720
ccagcctgac tcaaaaggag atagcgaagg ccactagcat agtggcttgg ttggccaagc    3780
aacgcaatgc atatgggggc ttctcttcta ctcaggatac tgtagttgct ctccaagctc    3840
ttgccaaata tgccactacc gcctacatgc catctgagga gatcaacctg gttgtaaaat    3900
ccactgagaa tttccagcgc acattcaaca tacagtcagt taacagattg gtatttcagc    3960 aggatacct gcccaatgtc cctggaatgt acacgttgga ggcctcaggc cagggctgtg    4020
```

| tctatgtgca gacggtgttg agatacaata ttctccctcc cacaaatatg aagaccttta | 4080 |
| gtcttagtgt ggaaatagga aaagctagat gtgagcaacc gacttcacct cgatccttga | 4140 |
| ctctcactat tcacaccagt tatgtgggga gccgtagctc ttccaatatg gctattgtgg | 4200 |
| aagtgaagat gctatctggg ttcagtccca tggaggcac caatcagtta cttctccagc | 4260 |
| aaccctggt gaagaaggtt gaatttggaa ctgacacact taacatttac ttggatgagc | 4320 |
| tcattaagaa cactcagact tacaccttca ccatcagcca agtgtgctg gtcaccaact | 4380 |
| tgaaaccagc aaccatcaag gtctatgact actacctacc agatgaacag gcaacaattc | 4440 |
| agtattctga tccctgtgaa tgaggatagg agctggaaac tcaattagtc ctctgtgaca | 4500 |
| tttactggag ggtggaacat tcttctgtcg cttgaagcag aactcattca atcaaataat | 4560 |
| ttaatttctc tgactagtat atgggtaaca atgaatatg tctgaacctc agctataata | 4620 |
| ctttctacta cctttgcaag gagatgggat aggaacaatc actcagagga ggcgttgcat | 4680 |
| gggcagggtc ataggggaa gaaggtggt ttagctgttt tatttagcca ttcaggggc | 4740 |
| tctccagaga ggagacggtg gtagagggtg aactagagaa gataagaatg tcttcctagg | 4800 |
| ccggatgcgg tggctcacgc ctgtaatccc agcactttgg gattgcgagg tgggcggatc | 4860 |
| acttgaggtc aggagttcaa gaccagcctg gccaacatgg taaaacccgt ctctactaac | 4920 |
| aatacaaaga ttagcctggt gtggtggcac gggcctgtaa tcgcagcccc ttggaaggcc | 4980 |
| aaggcaggag aatcgcctca acactggagg tggaggttgc agtgagctga gattgtgcca | 5040 |
| ctgcactcca gcctgggcaa tgaggcaaga ccctgtctca aaaataata aataataata | 5100 |
| ataataatgt ttttctagag tttcagtcta agggaaaatg tgatttaggg ctttggaaat | 5160 |
| tggctaaaaa aataaaaatg gaaagaaaa | 5190 |

<210> SEQ ID NO 15
<211> LENGTH: 4627
<212> TYPE: DNA
<213> ORGANISM: Homo sapiens
<300> PUBLICATION INFORMATION:
<308> DATABASE ACCESSION NUMBER: NM_001717
<309> DATABASE ENTRY DATE: 2008-02-11
<313> RELEVANT RESIDUES IN SEQ ID NO: (1)..(4627)

<400> SEQUENCE: 15

| gcggcggggg cggccatcgt gctgcgcagc ctgggcgctt ggggagccgc ccacttcgcc | 60 |
| gggtcgcgcc ccgacggccg gagcgtggat gcggcggcgc ccgccgagcc ggggcggacg | 120 |
| cggggcggcc cgggcccggg agacgcgccg gcagccccgg caccgcagcg gtcgcaggat | 180 |
| ggccgaggct atcagctgta ctctgaactg tagttgccaa gtttcaaac ccgggaaaat | 240 |
| aaaccaccgt cagtgtgacc aatgcaagca tggatgggtg gccacgctc taagtaagct | 300 |
| aaggatcccc cccatgtatc caacaagcca ggtggagatt gtccagtcca atgtagtgtt | 360 |
| tgatattagc agcctcatgc tctatgggac ccaggccatc cccgttcgcc taaaaatcct | 420 |
| actggaccgg ctcttcagtg tgttgaagca agatgaggtt ctccagatcc tccatgcctt | 480 |
| ggactggaca cttcaggatt atatccgtgg atacgtactg caggatgcat caggaaaggt | 540 |
| gttggatcac tggagcatca tgaccagtga ggaagaagtg gccaccttgc agcagttcct | 600 |
| tcgtttggga gagaccaaat ctatagttga actcatggca attcaagaga agaagagca | 660 |
| atccatcatc ataccacctt ccacagcaaa tgtagatatc agggctttca tcgagagctg | 720 |
| cagtcacagg agttctagcc tccccactcc tgtggacaaa ggaaacccca gcagtataca | 780 |
| cccctttgag aacctcataa gcaacatgac tttcatgctg cctttccagt tcttcaaccc | 840 |

-continued

```
tctgcctcct gcactgatag ggtcattgcc cgaacaatat atgttggagc agggtcatga        900
ccaaagtcag gaccccaaac aggaagtcca tgggcccttc cctgacagca gcttcttaac        960
ttccagttcc acaccatttc aggttgaaaa agatcagtgt ttaaactgtc cggatgctat       1020
tactaaaaaa gaagacagca cccatttaag tgactccagc tcatacaaca ttgtcactaa       1080
gtttgaaagg acacagttat cccctgaggc caaagtgaag cctgagagga atagccttgg       1140
tacaaagaag ggccgggtgt tctgcactgc atgtgagaag accttctatg acaaaggcac       1200
cctcaaaatc cactacaatg ccgtccactt gaagatcaag cataagtgca ccatcgaagg       1260
gtgtaacatg tgttcagct ccctaaggag ccggaatcgc catagcgcca accccaaccc        1320
tcggctgcac atgccaatga acagaaataa ccgggacaaa gacctcagga acagcctgaa       1380
cctggccagc tctgagaact acaagtgccc aggtttcaca gtgacgtccc cagactgtag       1440
gcctcctccc agctaccctg gttcaggaga ggattccaaa ggccaaccag ccttcccaaa       1500
cattgggcaa aatggtgtgc ttttcccaa cctaaagaca gtccagccag tccttccttt        1560
ctaccgcagt ccagccacgc ctgccgaggt agcaaacacg cctgggatac tcccttccct       1620
cccgctgttg tcctcttcaa tcccagaaca gctcatttca aacgaaatgc catttgatgc       1680
ccttcccaag aagaaatcca ggaagtccag tatgcctatc aaaatagaga aagaagctgt       1740
ggaaatagct aatgagaaaa gacacaacct cagctcagat gaagacatgc ccctacaggt       1800
ggtcagtgaa gatgagcagg aggcctgcag tcctcagtca cacagagtat ctgaggagca       1860
gcatgtacag tcaggaggct tagggaagcc tttccctgaa ggggagaggc cctgccatcg       1920
tgaatcagta attgagtcca gtggagccat cagccaaacc cctgagcagg ccacacacaa       1980
ttcagagagg gagactgagc agacaccagc attgatcatg gtgccaaggg aggtcgagga       2040
tggtggccat gaacactact tcacacctgg gatggaaccc caagttcctt tttctgacta       2100
catggaactg cagcagcgcc tgctggctgg gggactcttc agtgctttgt ccaacagggg       2160
aatggctttt ccttgtcttg aagattctaa agaactggag cacgtgggtc agcatgcatt       2220
agcaaggcag atagaagaaa atcgcttcca gtgtgacatc tgcaagaaga cctttaaaaa       2280
tgcttgtagt gtgaaaattc atcacaagaa tatgcatgtc aaagaaatgc acacatgcac       2340
agtggagggc tgtaatgcta cctttcccctc ccgcaggagc agagacagac acagctcaaa       2400
cctaaacctc caccaaaaag cattgagcca ggaagcattg gagagtagtg aagatcattt       2460
ccgtgcagct taccttctga agatgtggc taaggaagcc tatcaggatg tggcttttac        2520
acagcaagcc tccagacat ctgtcatctt caaaggaaca agtcgaatgg gcagtctggt        2580
ttacccaata cgcaagtcc acagtgccag cctggagagc tacaactctg gcccccttgag       2640 cgagggcacc atcctggatt tgagcactac ctcgagcatg aagtcagaga gtagcagcca       2700
ttcttcctgg gactctgacg gggtgagtga ggaaggcact gtgcttatgg aggacagtga       2760
tgggaactgt gaagggtcga gccttgtccc tgggaagat gagtacccca tctgtgtcct        2820
gatggagaag gctgaccaga gccttgctag cctgccttct gggttgccca taacctgtca       2880
tctctgccaa aagacataca gtaacaaagg gacctttagg gcccactaca aaactgtgca       2940
cctccggcag ctccacaaat gcaaagtacc aggctgcaac accatgtttt cgtctgttcg       3000
cagtcgaaac agacacagcc agaatcccaa cctgcacaaa agcctggcct catctccaag       3060
tcacctccag taacaagatg gcaaaccaag tatgctcaga taagcttttt tcataattca       3120
ggaataaagt agtccataga aatgtttctg tttcatatca tttggggcga gtcaggcaaa       3180
agtatttgat ttgactttat agttttccac agcacaatga gcaaaagaca aacctcgtgg       3240
```

```
gaagatgaca ctggggcagc ccttcctatt attttctta gcccaagagg tctttcactg    3300
atacaaggaa aacttgcaga aatgtgattt ttcccagatt tgtttacatg ttccctggga    3360
cagatccagg tctgcagatc gacaccagtg ggcccaggac ctgggggtgg ctttaaatga    3420
ggcttgcagt gttaaaggtc ttggataaga agggtcctgg ggaagaagac tctgtggaca    3480
agataccagt ccccaaaaca gcattttcag ttccttcttc aattagtttg aaatccagac    3540
ctgagtttgg aagactgatt ttttgagacc atccctgtgt ttggagtgga taattgtccc    3600
tcccctcagc cctgcaccag aggtctcata tgttacccca gggagttctc agaggattgg    3660
gttggcctct aacatgttcc ttgttaattc ttgttctgta acatgcattc aagaagctag    3720
gggaaaaata tctcatgcac ttaaataatg gtcttcaatt taatttaaaa atattttgac    3780
aatatttaat ttgtgcttat gtggtgtttg gtgtgagtgc agatattgca ctgtgtcacc    3840
tctggatctc tgctcagaag cagaacaagt gatgacctaa atgtcaaaat cactgctcgt    3900
tttcatttgg tgaacttcaa actctgttct ttttggtcac ctgtgaatg aatgcaagca    3960 tgattttggc aggaacattt gtacatattc tgccgtagat aatgtggttc tgatggttgt    4020
tgtgtatttt cagtatcact ggatccctca gtcttcaccg ttttataaac gtataagatt    4080
aggatgaact tttgaattta cttggtagga aaaaagtag gacattattg ccatattgta    4140
tgtcttaata tttaacttat tcggaaatat attccacact gttacataca ttttccatgg    4200
tagaaaggaa gttcagtcag tcctgtggaa tgaaaccatc tcctaaaatt cagcatttgc    4260
agcattctaa aagcctgtgt aggtacaagg acattgattt tgtattcaga attcaagtta    4320
actatctttt aaattcgtgg ttgatgtaag taataaaaaa cattcttaaa gttgagggtt    4380
ataagagaga ttatttctgt ggtctaaagg ttaaaaagcc aacaacctgt taccaattat    4440
ttcagctttt tttgttttaa taagtgtgac aacttaaaac ttgtttctat ttaaagtgaa    4500
atgtatcttt caactgttta gttacccagc tgtttaatat tccagtcttc ccaaagtgaa    4560
aagatttgta tacaaatgtt ttctatgatt taataaaaat atatggcaca ccaaaaaaaa    4620
aaaaaaa                                                              4627
```

<210> SEQ ID NO 16
<211> LENGTH: 2053
<212> TYPE: DNA
<213> ORGANISM: Homo sapiens
<300> PUBLICATION INFORMATION:
<308> DATABASE ACCESSION NUMBER: NM_001630
<309> DATABASE ENTRY DATE: 2008-08-07
<313> RELEVANT RESIDUES IN SEQ ID NO: (1)..(2053)

<400> SEQUENCE: 16

```
aaagccaggc agagcccggg ggcgaggggg cggcaggcag gtgtagcgct gccctgggcg     60
ggcttgcacc cccacaccca agtgagcggc ctgctcactc ctcagctgca ggagccagac    120
gtgtggagtc ccagcagagg ccaacctgtg tctcttcatc tccgtgagaa aggtgccccc    180
gaagtgaaag agatggcctg gtggaaagcc tggattgaac aggagggtgt cacagtgaag    240
agcagctccc acttcaaccc agaccctgat gcagagaccc tctacaaagc catgaagggg    300
atcgggacca acgagcaggc tatcatcgat gtgctcacca gagaagcaa cacgcagcgg    360 cagcagatcg ccaagtcctt caaggctcag ttcggcaagg acctcactga gaccttgaag    420
tctgagctca gtggcaagtt tgagaggctc attgtggccc ttatgtaccc gccatacaga    480
tacgaagcca aggagctgca tgacgccatg aaggggcttag gaaccaagga gggtgtcatc    540
attgagatcc tggcctctcg gaccaagaac cagctgcggg agataatgaa ggcgtatgag    600
```

-continued

| | |
|---|---|
| gaagactatg ggtccagcct ggaggaggac atccaagcag acacaagtgg ctacctggag | 660 |
| aggatcctgg tgtgcctcct gcagggcagc agggatgatg tgagcagctt tgtggacccg | 720 |
| gcactggccc tccaagacgc acaggatctg tatgcggcag gcgagaatat tcgtgggact | 780 |
| gatgagatga aattcatcac catcctgtgc acgcgcagtg ccactcacct gctgagagtg | 840 |
| tttgaagagt atgagaaaat tgccaacaag agcattgagg acagcatcaa gagtgagacc | 900 |
| catggctcac tggaggaggc catgctcact gtggtgaaat gcacccaaaa cctccacagc | 960 |
| tactttgcag agagactcta ctatgccatg aagggagcag ggacgcgtga tgggaccctg | 1020 |
| ataagaaaca tcgtttcaag gagcgagatt gacttaaatc ttatcaaatg tcacttcaag | 1080 |
| aagatgtacg gcaagaccct cagcagcatg atcatggaag acaccagcgg tgactacaag | 1140 |
| aacgccctgc tgagcctggt gggcagcgac ccctgaggca cagaagaaca agagcaaaga | 1200 |
| ccatgaagcc agagtctcca ggactcctca ctcaacctcg gccatggacg caggttgggt | 1260 |
| gtgaggggg tccagccttt tcggtcttct atttccctat ttccagtgct ttccagccgg | 1320 |
| gtttctgacc cagagggtgg aaccggcctg gactcctctt cccaacttcc tccaggtcat | 1380 |
| ttcccagtgt gagcacaatg ccaaccttag tgtttctcca gccagacaga tgcctcagca | 1440 |
| tgaagggctt ggggacttgt ggatcattcc ttcctccctg caggagcttc ccaagctggt | 1500 |
| cacagagtct cctgggcaca ggttatacag accccagccc cattcccatc tactgaaaca | 1560 |
| gggtctccac aagagggggcc agggaatatg gttttttaac aagcgtctta caaaacactt | 1620 |
| ctctatcatg cagccggaga gctggctggg agccctttg ttttagaaca cacatccttc | 1680 |
| agcagctgag aaacgaacac gaatccatcc caaccgagat gccattaaca ttcatctaaa | 1740 |
| aatgttaggc tctaaatgga cgaaaaattc tctcgccatc ttaataacaa ataaaactac | 1800 |
| aaattcctga cccaaggaca ctgtgttata agaggcgtgg gctcccctgg tggctgacca | 1860 |
| ggtcagctgc cctggccttg cacccctctg catgcagcac agaagggtgt gaccatgccc | 1920 |
| tcagcaccac tcttgtcccc actgaacggc aactgagact gggtacctgg agattctgaa | 1980 |
| gtgcctttgc tgtggttttc aaaataataa agatttgtat tcaactcaaa aaaaaaaaa | 2040 |
| aaaaaaaaaa aaa | 2053 |

<210> SEQ ID NO 17
<211> LENGTH: 1013
<212> TYPE: DNA
<213> ORGANISM: Homo sapiens
<300> PUBLICATION INFORMATION:
<308> DATABASE ACCESSION NUMBER: NM_007196
<309> DATABASE ENTRY DATE: 2009-10-18
<313> RELEVANT RESIDUES IN SEQ ID NO: (1)..(1013)

<400> SEQUENCE: 17

| | |
|---|---|
| gttcccagaa gctccccagg ctctagtgca ggaggagaag gaggaggagc aggaggtgga | 60 |
| gattcccagt taaaaggctc cagaatcgtg taccaggcag agaactgaag tactggggcc | 120 |
| tcctccactg ggtccgaatc agtaggtgac cccgcccctg gattctggaa gacctcacca | 180 |
| tgggacgccc ccgacctcgt gcggccaaga cgtggatgtt cctgctcttg ctgggggag | 240 |
| cctgggcagg acactccagg gcacaggagg acaaggtgct gggggtcat gagtgccaac | 300 |
| cccattcgca gccttggcag gcggccttgt tccaggggca gcaactactc tgtggcggtg | 360 |
| tccttgtagg tggcaactgg gtccttacag ctgcccactg taaaaaaccg aaatacacag | 420 |
| tacgcctggg agaccacagc ctacagaata aagatggccc agagcaagaa atacctgtgg | 480 |
| ttcagtccat cccacacccc tgctacaaca gcagcgatgt ggaggaccac aaccatgatc | 540 |

| | |
|---|---|
| tgatgcttct tcaactgcgt gaccaggcat ccctggggtc caaagtgaag cccatcagcc | 600 |
| tggcagatca ttgcacccag cctggccaga agtgcaccgt ctcaggctgg ggcactgtca | 660 |
| ccagtccccg agagaatttt cctgacactc tcaactgtgc agaagtaaaa atctttcccc | 720 |
| agaagaagtg tgaggatgct tacccggggc agatcacaga tggcatggtc tgtgcaggca | 780 |
| gcagcaaagg ggctgacacg tgccagggcg attctggagg cccctggtg tgtgatggtg | 840 |
| cactccaggg catcacatcc tggggctcag acccctgtgg gaggtccgac aaacctggcg | 900 |
| tctataccaa catctgccgc tacctggact ggatcaagaa gatcataggc agcaagggct | 960 |
| gattctagga taagcactag atctccctta ataaactcac aactctctgg ttc | 1013 |

<210> SEQ ID NO 18
<211> LENGTH: 3240
<212> TYPE: DNA
<213> ORGANISM: Homo sapiens
<300> PUBLICATION INFORMATION:
<308> DATABASE ACCESSION NUMBER: NM_144777
<309> DATABASE ENTRY DATE: 2009-07-18
<313> RELEVANT RESIDUES IN SEQ ID NO: (1)..(3240)

<400> SEQUENCE: 18

| | |
|---|---|
| aagaaacctc tgaactgttc actaatacag tcaggtagag gttgagactc cactgaataa | 60 |
| actctaggtt cccatttctt tcagccagat cctcccaggg aatcactaca ggctggttag | 120 |
| ccaaaaagtc ctgattttct gctcaataga ggtccttact ggaaggcagc atgtccaatg | 180 |
| ttaccttgag aaaaatgtct cccacaggaa atgagatgaa gagcaccact cagggaacca | 240 |
| cacggaagca gcaggatttt cacgaggtga acaaaagaag aactttctta caggataaca | 300 |
| gttggataaa gaaacgccct gaagaagaaa aagatgaaaa ttacggtagg gtggtgctca | 360 |
| accgacataa ttcccatgat gcattggaca ggaaagtaaa tgagagagat gtgccaaaag | 420 |
| ctacaattag tcggtacagt tctgatgaca ctttggacag gatctcagac agaaatgatg | 480 |
| ctgctaaaac atataaggcc aatacctttgg ataaccaact aaccaatagg agcatgtcca | 540 |
| tgtttagatc actggaagta acaaagttgc aacctggcgg ttcattgaat gccaacacct | 600 |
| ccaacaccat agcatccact tctgctacta ctcctgtaaa gaagaagagg cagtcctggt | 660 |
| ttccaccgcc ccctccaggt tacaatgcct cctcgagcac aggaaccagg agacgggaac | 720 |
| caggtgttca ccctccaata cctccaaagc ccagttctcc tgtttcttct cctaaccagc | 780 |
| tgagacagga taataggcag atacatccac ctaaaccagg tgtatataca gaaaccaaca | 840 |
| gatctgctga agaaatata aggagtcagg atcttgataa catcgtcaaa gtggccactt | 900 |
| cacttcagag aagtgacaaa ggtgaagaat tggataatct catcaaaatg aacaaaagct | 960 |
| tgaataggaa tcaaggtctt gatagtctct tcagagcaaa tccaaaggta gaagaaagag | 1020 |
| agaaaagagc caaaagcctt gaaagtctca tctatatgag tacccggaca gataaagatg | 1080 |
| gcaaaggaat ccaaagcctt ggaagtccga ttaaagttaa tcaaaggact gacaaaaatg | 1140 |
| agaaggaag acaaaatctc gaatctgttg ctaaagtgaa tgccaggatg aataaaacga | 1200 |
| gcagaagaag tgaagacctt gataatgcta ctgaagtaaa tcccaaagga catgaaaata | 1260 |
| ccactggaaa aaaagacctt gatgggctta ttaaagtgga tcctgaaaca aataaaaata | 1320 |
| ttacgagggg ccagagcctt gataatctca tcaaagtgac ccctgaagta aagagaagta | 1380 |
| accaaggttc caaagacctt aataacttca tcaaagtgta tccaggaaca gaaaaaagta | 1440 |
| ctgaaggggg ccaaagtctc gacagcctca ttaaagtgac tcctgaaaga aacagaacta | 1500 |
| accaagggaa ccaagacttg gaaaatctta tcaaagtgat cccttcagca aacaaaagca | 1560 |

-continued

| | |
|---|---|
| gtgaacaagg tcttgatgaa catattaatg tcagccccaa agctgtcaaa acactgatg | 1620 |
| gaaaacaaga tcttgataaa ctcatcaagg tgaatcctga aattttcaca acaaccaaa | 1680 |
| gaaaccaaga tcttgctaac ctcatcaaag taaatcctgc agtaatcaga acaatcaga | 1740 |
| gccaagactt ggacaatctt attaaagtga aaccttcagc tcttagaaac actaatcgag | 1800 |
| accagaacct ggaaaattta attgaagtaa attctcatgt gtctgaaaac aagaatggaa | 1860 |
| gctctaacac tggagccaag caggcaggac cacaggatac tgttgtgtac acaaggacat | 1920 |
| atgtggagaa tagtaaatca cccaaggatg gatatcagga gaatatctct ggaaaataca | 1980 |
| tacaaactgt ttattcaact tctgataggc tgtcattga aagagatatg tgcacttact | 2040 |
| gccgaaaacc cttgggtgta gaaactaaaa tgattttaga tgaattacaa atttgctgcc | 2100 |
| attctacttg ctttaagtgt gaaatatgca agcagccttt ggaaaatcta caagcgggtg | 2160 |
| atagtatttg gatttataga cagacaatac actgtgaacc ttgctactct aaaattatgg | 2220 |
| caaagtggat tccataactc tggcacaagg aaatcaagat gaaaagcact cattaaggaa | 2280 |
| ttaaagttac aagttttatc ttaataatat gtaatctaga aaagctttca cattgaagat | 2340 |
| caactcttgt acaaaattaa caattctgtt attgcataag taatctaatt gtcttcaata | 2400 |
| aggtcacaca cataaaaaga gccatctggt ctctggctag agttagcaat aaaaagttca | 2460 |
| aatggttcca gattccagtg tcaaaggagt gatgcattac actccagcca ggtccatccc | 2520 |
| tgctccgtat gttggctgtg agtggtggtt tccatttaaa ccaagtttct catttcttca | 2580 |
| ccttttttc tctaagaatt tggattcgta gacattgaca tcccgaagaa ctgtcaagga | 2640 |
| agcaagatat gctttcttca tctgcaaaag aaatactaac aacaattttc ttatacagtt | 2700 |
| tggcagaaag atgttaacat aaaaagttta tacctcaa aaatcactaa actttccaga | 2760 |
| tctctgtcct attatttgta acacaagggg cattggataa aatgatttct agggttcctt | 2820 |
| ttgcttccca aattctctga ttctaaagca gttttagaa tcattagctc tttggaaaca | 2880 |
| tatatgcata catgtttgtt aagcctattg aactaggtag gacatataaa caatttaatt | 2940 |
| ttagtgtcat tgtttaatca cagacttagt gtttgaaaac tgtgttttaa aaacagaaac | 3000 |
| agattgatgg gtaacaggta aaatatgaca tgtatagctt acatgttatt atttgttaaa | 3060 |
| ttttctttgt atacatttca aaatctgggt atacttataa tccattagaa gtaatggtta | 3120 |
| tggactaaaa agatatgttc tttagtatgt tatatatact catattacat agcagtatgt | 3180 |
| ttacaaaagg cttataaaaa taaaatgaac tatcagttac atagaaaaaa aaaaaaaaaa | 3240 |

<210> SEQ ID NO 19
<211> LENGTH: 1938
<212> TYPE: DNA
<213> ORGANISM: Homo sapiens
<300> PUBLICATION INFORMATION:
<308> DATABASE ACCESSION NUMBER: NM_006153
<309> DATABASE ENTRY DATE: 2009-08-16
<313> RELEVANT RESIDUES IN SEQ ID NO: (1)..(1938)

<400> SEQUENCE: 19

| | |
|---|---|
| ccaagagcta cgcggcggcg gcggagcgca ggcctcgtgc cgttacggcc atcacggcgg | 60 |
| ccgcagtggc gtcctggagc cctcctcagt gctgaagctg ctgaaagatg gcagaagaag | 120 |
| tggtggtagt agccaaattt gattatgtgg cccaacaaga acaagagttg acatcaaga | 180 |
| agaatgagag attatggctt ctggatgatt ctaagtcctg gtggcgagtt cgaaattcca | 240 |
| tgaataaaac aggttttgtg ccttctaact atgtggaaag gaaaacagt gctcggaaag | 300 |
| catctattgt gaaaaaccta aaggatacct taggcattgg aaaagtgaaa agaaaaccta | 360 |

-continued

```
gtgtgccaga ttctgcatct cctgctgatg atagttttgt tgacccaggg gaacgtctct      420
atgacctcaa catgcccgct tatgtgaaat ttaactacat ggctgagaga gaggatgaat      480
tatcattgat aaaggggaca aaggtgatcg tcatggagaa atgcagtgat gggtggtggc      540
gtggtagcta caatgacaa gttggatggt tcccttcaaa ctatgtaact gaagaaggtg      600
acagtccttt gggtgaccat gtgggttctc tgtcagagaa attagcagca gtcgtcaata      660
acctaaatac tgggcaagtg ttgcatgtgg tacaggctct ttacccattc agctcatcta      720
atgatgaaga acttaatttc gagaaggag atgtaatgga tgttattgaa aaacctgaaa      780
atgacccaga gtggtggaaa tgcaggaaga tcaatggtat ggttggtcta gtaccaaaaa      840
actatgttac cgttatgcag aataatccat taacttcagg tttggaacca tcacctccac      900
agtgtgatta cattaggcct tcactcactg gaaagtttgc tggcaatcct tggtattatg      960
gcaaagtcac caggcatcaa gcagaaatgg cattaaatga aagaggacat gaaggggatt     1020
tcctcattcg tgatagtgaa tcttcgccaa atgatttctc agtatcacta aaagcacaag     1080
ggaaaaacaa gcattttaaa gtccaactaa aagagactgt ctactgcatt gggcagcgta     1140
aattcagcac catggaagaa cttgtagaac attacaaaaa ggcaccaatt tttacaagtg     1200
aacaaggaga aaaattatat cttgtcaagc atttatcatg atactgctga ccagaagtga     1260
ctgctgtgta gctgtaattt gtcatgtaat tgaagactga gaaatgttg ggtccagtcg     1320 tgcttgattg gaaattgttg tttctaaatc tatatgagaa ttgacaataa gtattttat     1380 tataactcag cccatacata tatactatgt atgcagtgca tctgcataga acagttcctt     1440
atccttggcc ttctgtttta ttgtttttt ctttgctgtt ttcctttgc ttctaatatt     1500 acagttttgt attttgtaaa caaaaatcaa ataatgcata tcagaatctt tatatgaag     1560 aaatcctta ttgcctttcc tttgtttcct tgtaaaggca ccctgttctg ttatggtttt     1620
tcattatata aaattattat atctatatat gacatatgct aaaatttctt ggagagtgtt     1680
aatcttttct gtgactaaat agcaataata agtggaaaat tagaaattat ttccaggtat     1740
tatatttgtc acaggccatt gtaaatacca agtatattgt gtctgccata attttaaaa     1800 atacattcat tgtcttcagt catacagcaa gacacatgag acatagatta gaaaacatgt     1860
tgtacaattt taatttacaa ctgttggaaa taaaaatcac ttaattttt tccaaaaaaa     1920 aaaaaaaaaa aaaaaaa                                                    1938
```

<210> SEQ ID NO 20
<211> LENGTH: 2056
<212> TYPE: DNA
<213> ORGANISM: Homo sapiens
<300> PUBLICATION INFORMATION:
<308> DATABASE ACCESSION NUMBER: NM_144717
<309> DATABASE ENTRY DATE: 2009-07-19
<313> RELEVANT RESIDUES IN SEQ ID NO: (1)..(2056)

<400> SEQUENCE: 20

```
aaagttacat tttctctgga actctcctag gccactccct gctgatgcaa catctgggtt       60
tgggcagaaa ggagggtgct tcggagcccg ccctttctga gcttcctggg ccggctctag      120
aacaattcag gcttcgctgc gactcagacc tcagctccaa catatgcatt ctgaagaaag      180
atggctgaga tggacagaat gctttatttt ggaaagaaac aatgttctag gtcaaactga      240
gtctaccaaa tgcagacttt cacaatggtt ctagaagaaa tctggacaag tcttttcatg      300 tggttttct acgcattgat tccatgtttg ctcacagatg aagtggccat tctgcctgcc      360
cctcagaacc tctctgtact ctcaaccaac atgaagcatc tcttgatgtg gagcccagtg      420
```

| | |
|---|---:|
| atcgcgcctg gagaaacagt gtactattct gtcgaatacc aggggagta cgagagcctg | 480 |
| tacacgagcc acatctggat ccccagcagc tggtgctcac tcactgaagg tcctgagtgt | 540 |
| gatgtcactg atgacatcac ggccactgtg ccatacaacc ttcgtgtcag ggccacattg | 600 |
| ggctcacaga cctcagcctg gagcatcctg aagcatccct taatagaaa ctcaaccatc | 660 |
| cttacccgac ctgggatgga gatcaccaaa gatggcttcc acctggttat tgagctggag | 720 |
| gacctggggc cccagtttga gttccttgtg gcctactgga ggaggagcc tggtgccgag | 780 |
| gaacatgtca aaatggtgag gagtgggggt attccagtgc acctagaaac catggagcca | 840 |
| ggggctgcat actgtgtgaa ggcccagaca ttcgtgaagg ccattgggag gtacagcgcc | 900 |
| ttcagccaga cagaatgtgt ggaggtgcaa ggagaggcca ttccctggt actggccctg | 960 |
| tttgcctttg ttggcttcat gctgatcctt gtggtcgtgc cactgttcgt ctggaaaatg | 1020 |
| ggccggctgc tccagtactc ctgttgcccc gtggtggtcc tcccagacac cttgaaaata | 1080 |
| accaattcac cccagaagtt aatcagctgc agaaggagg aggtggatgc ctgtgccacg | 1140 |
| gctgtgatgt ctcctgagga actcctcagg gcctggatct cataggtttg cggaagggcc | 1200 |
| caggtgaagc cgagaacctg gtctgcatga catggaaacc atgaggggac aagttgtgtt | 1260 |
| tctgttttcc gccacggaca agggatgaga gaagtaggaa gagcctgttg tctacaagtc | 1320 |
| tagaagcaac catcagaggc agggtggttt gtctaacaga acactgactg aggcttaggg | 1380 |
| gatgtgacct ctagactggg ggctgccact tgctggctga gcaaccctgg gaaaagtgac | 1440 |
| ttcatccctt cggtcctaag tttttctcatc tgtaatgggg gaattaccta cacacctgct | 1500 |
| aaacacacac acacagagtc tctctctata tatacacacg tacacataaa tacacccagc | 1560 |
| acttgcaagg ctagagggaa actggtgaca ctctacagtc tgactgattc agtgtttctg | 1620 |
| gagagcagga cataaatgta tgatgagaat gatcaaggac tctacacact gggtggcttg | 1680 |
| gagagcccac tttcccagaa taatccttga gagaaaagga atcatgggag caatggtgtt | 1740 |
| gagttcactt caagcccaat gccggtgcag aggggaatgg cttagcgagc tctacagtag | 1800 |
| gtgacctgga ggaaggtcac agccacactg aaaatgggat gtgcatgaac acggaggatc | 1860 |
| catgaactac tgtaaagtgt tgacagtgtg tgcacactgc agacagcagg tgaaatgtat | 1920 |
| gtgtgcaatg cgacgagaat gcagaagtca gtaacatgtg catgtttgtt gtgctccttt | 1980 |
| tttctgttgg taaagtacag aattcagcaa ataaaagggg ccaccctggc caaaagcggt | 2040 |
| aaaaaaaaaa aaaaaa | 2056 |

<210> SEQ ID NO 21
<211> LENGTH: 1786
<212> TYPE: DNA
<213> ORGANISM: Homo sapiens
<300> PUBLICATION INFORMATION:
<308> DATABASE ACCESSION NUMBER: NM_022664
<309> DATABASE ENTRY DATE: 2009-10-11
<313> RELEVANT RESIDUES IN SEQ ID NO: (1)..(1786)

<400> SEQUENCE: 21

| | |
|---|---:|
| agaggaggag cagctgggac tgagtcatgg caggaagctg aggagggcgg gagatcacac | 60 |
| cagacaatta taaagaaga gctggtcctg aagctcacaa ccgtaacagc caccagacaa | 120 |
| gcttcagtgg ccggcccttc acatccagac ttgcctgaga ggaccacct ctgagtgtcc | 180 |
| agtggtcagt tgcccagga tggggaccac agccagagca gccttggtct tgacctattt | 240 |
| ggctgttgct tctgctgcct ctgagggagg cttcacggct acaggacaga ggcagctgag | 300 |
| gccagagcac tttcaagaag ttggctacgc agctcccccc tccccaccccc tatcccgaag | 360 |

```
cctcccatg  gatcaccctg  actcctctca  gcatggccct  cccctttgagg  gacagagtca     420
agtgcagccc  cctccctctc  aggaggccac  ccctctccaa  caggaaaagc  tgctacctgc     480
ccaactccct  gctgaaaagg  aagtgggtcc  ccctctccct  caggaagctg  tccccctcca     540
aaaagagctg  ccctctctcc  agcaccccaa  tgaacagaag  gaaggaacgc  cagctccatt     600
tggggaccag  agccatccag  aacctgagtc  ctggaatgca  gcccagcact  gccaacagga     660
ccggtcccaa  gggggctggg  gccaccggct  ggatggcttc  cccctgggc   ggccttctcc     720
agacaatctg  aaccaaatct  gccttcctaa  ccgtcagcat  gtggtatatg  gtccctggaa     780
cctaccacag  tccagctact  cccacctcac  tcgccagggt  gagaccctca  atttcctgga     840
gattggatat  tcccgctgct  gccactgccg  cagccacaca  aaccgcctag  agtgtgccaa     900
acttgtgtgg  gaggatacc   ttgacaaata  ctgtgaccgg  gagtatgctg  tgaagaccca     960
ccaccacttg  tgttgccgcc  accctcccag  ccctactcgg  gatgagtgct  tgcccgtcg     1020
ggctccttac  cccaactatg  accgggacat  cttgaccatt  gacatcggtc  gagtcacccc    1080
caacctcatg  ggccacctct  gtggaaacca  aagagttctc  accaagcata  acatattcc    1140
tgggctgatc  cacaacatga  ctgcccgctg  ctgtgacctg  ccatttccag  aacaggcctg    1200
ctgtgcagag  gaggagaaat  taaccttcat  caatgatctg  tgtggtcccc  gacgtaacat    1260
ctggcgagac  cctgccctct  gctgttacct  gagtcctggg  gatgaacagg  tcaactgctt    1320
caacatcaat  tatctgagga  acgtggctct  agtgtctgga  gacactgaga  acgccaaggg    1380
ccaggggag   cagggctcaa  ctggaggaac  aaatatcagc  tccacctctg  agcccaagga    1440
agaatgagtc  accccagagc  cctagagggt  cagatggggg  gaaccccacc  ctgccccacc    1500
catctgaaca  ctcattacac  taaacacctc  ttggatttgg  tgtcctcatt  gtctatctaa    1560
tgtctcaccc  gcagtgtttt  aagtggatct  tggtgccctg  gccaggagg   gcactggcgt    1620
tttcagacac  accacagaca  aacacaccct  cctaagcctg  cttgtatttc  cttcagtgcc    1680
tggcccctga  ggcccacggc  cctgccccct  tcactgagca  gatgttcaca  ggctgtggga    1740
tgcgaccata  actaaacagc  ttgacgtcaa  aaaaaaaaaa  aaaaaa                    1786
```

```
<210> SEQ ID NO 22
<211> LENGTH: 1040
<212> TYPE: DNA
<213> ORGANISM: Homo sapiens
<300> PUBLICATION INFORMATION:
<308> DATABASE ACCESSION NUMBER: NM_032330
<309> DATABASE ENTRY DATE: 2008-02-11
<313> RELEVANT RESIDUES IN SEQ ID NO: (1)..(1040)

<400> SEQUENCE: 22
cacatgtaaa  ctacttgaac  tccatttcat  cttttttcat  accatctcta  agattgctgc      60
cgcatttgct  tgttaaactg  aaagcatgtt  tcttgcaaag  gctctattgg  aaggagcaga     120
tcgaggtctt  ggagaagctc  ttggaggcct  ctttggagga  ggtggtcaga  gaagagaagg     180
aggaggaaga  aatattggag  ggatagttgg  aggaattgtg  aattttatca  gtgaggctgc     240
agcagctcag  tatactccag  aaccgcctcc  cactcagcag  catttcacca  gtgtggaggc     300
ctcagaaagt  gaggaagtta  ggcgatttcg  gcaacaattt  acacagctgg  ctggaccaga     360
catggaggtg  ggtgccactg  atctgatgaa  tattctcaac  aaagtccttt  ctaagcacaa     420
agatcttaag  actgacggtt  ttagtcttga  cacctgccgg  agcattgtgt  ctgtcatgga     480
cagtgacacg  actggtaagc  tgggctttga  agaatttaag  tatctgtgga  acaacatcaa     540
gaaatggcag  tgtgtttata  agcagtatga  cagggaccat  tctgggtctc  tgggaagttc     600
```

| | |
|---|---|
| tcagctgcgg ggagctctgc aggccgcagg cttccagcta aatgaacaac tttaccaaat | 660 |
| gattgtccgc cggtatgcta atgaagatgg agatatggat tttaacaatt tcatcagctg | 720 |
| cttggtccgc ctggatgcca tgtttcgtgc cttcaagtct ctggatagag atagagatgg | 780 |
| cctgattcaa gtgtctatca aagaatggct gcagttgacc atgtattcct gaagtgggaa | 840 |
| ctgagaagtc aagatcctcc ctggaggaca ggactgaaaa ccttgccaag ctgtacacag | 900 |
| ttgctgatac cctgtgcaac agctctcatt tcctggcaag ctcttcaca acctacata | 960 |
| tttctgatca tgtgctgcct tttactgctg aattaaaaca gatatttcat aaaaaaaaaa | 1020 |
| aaaaaaaaaa aaaaaaaaaa | 1040 |

<210> SEQ ID NO 23
<211> LENGTH: 2081
<212> TYPE: DNA
<213> ORGANISM: Homo sapiens
<300> PUBLICATION INFORMATION:
<308> DATABASE ACCESSION NUMBER: NM_002421
<309> DATABASE ENTRY DATE: 2009-11-22
<313> RELEVANT RESIDUES IN SEQ ID NO: (1)..(2081)

<400> SEQUENCE: 23

| | |
|---|---|
| agcatgagtc agacagcctc tggctttctg aagggcaag gactctatat atacagaggg | 60 |
| agcttcctag ctgggatatt ggagcagcaa gaggctggga agccatcact taccttgcac | 120 |
| tgagaaagaa gacaaaggcc agtatgcaca gctttcctcc actgctgctg ctgctgttct | 180 |
| ggggtgtggt gtctcacagc ttcccagcga ctctagaaac acaagagcaa gatgtggact | 240 |
| tagtccagaa atacctggaa aaatactaca acctgaagaa tgatgggagg caagttgaaa | 300 |
| agcggagaaa tagtggccca gtggttgaaa aattgaagca aatgcaggaa ttctttgggc | 360 |
| tgaaagtgac tgggaaacca gatgctgaaa ccctgaaggt gatgaagcag cccagatgtg | 420 |
| gagtgcctga tgtggctcag tttgtcctca ctgaggggaa ccctcgctgg gagcaaacac | 480 |
| atctgaccta caggattgaa aattacacgc cagatttgcc aagagcagat gtggaccatg | 540 |
| ccattgagaa agccttccaa ctctggagta atgtcacacc tctgacattc accaaggtct | 600 |
| ctgagggtca agcagacatc atgatatctt ttgtcagggg agatcatcgg acaactctc | 660 |
| cttttgatgg acctggagga aatcttgctc atgcttttca accaggccca ggtattggag | 720 |
| gggatgctca ttttgatgaa gatgaaaggt ggaccaacaa tttcagagag tacaacttac | 780 |
| atcgtgttgc agctcatgaa ctcggccatt ctcttggact ctcccattct actgatatcg | 840 |
| gggctttgat gtaccctagc tacaccttca gtggtgatgt tcagctagct caggatgaca | 900 |
| ttgatggcat ccaagccata tatggacgtt cccaaaatcc tgtccagccc atcggcccac | 960 |
| aaaccccaaa agcgtgtgac agtaagctaa cctttgatgc tataactacg attcggggag | 1020 |
| aagtgatgtt cttaaagac agattctaca tgcgcacaaa tccttctac ccggaagttg | 1080 |
| agctcaattt catttctgtt ttctggccac aactgccaaa tgggcttgaa gctgcttacg | 1140 |
| aatttgccga cagagatgaa gtccggtttt tcaaagggaa taagtactgg gctgttcagg | 1200 |
| gacagaatgt gctacacgga taccccaagg acatctacag ctccttttgc ttccctagaa | 1260 |
| ctgtgaagca tatcgatgct gctctttctg aggaaaacac tggaaaaacc tacttctttg | 1320 |
| ttgctaacaa atactggagg tatgatgaat ataaacgatc tatggatcca ggttatccca | 1380 |
| aaatgatagc acatgacttt cctggaattg ccacaaagt tgatgcagtt ttcatgaaag | 1440 |
| atggattttt ctatttcttt catgaacaa gacaatacaa atttgatcct aaaacgaaga | 1500 |
| gaattttgac tctccagaaa gctaatagct ggttcaactg caggaaaaat tgaacattac | 1560 |

```
taatttgaat ggaaaacaca tggtgtgagt ccaaagaagg tgttttcctg aagaactgtc    1620 tatttttctca gtcattttta acctctagag tcactgatac acagaatata atcttattta   1680
tacctcagtt tgcatatttt tttactattt agaatgtagc ccttttttgta ctgatataat   1740 ttagttccac aaatggtggg tacaaaaagt caagtttgtg gcttatggat tcatataggc   1800
cagagttgca aagatctttt ccagagtatg caactctgac gttgatccca gagagcagct   1860
tcagtgacaa acatatcctt tcaagacaga aagagacagg agacatgagt ctttgccgga   1920
ggaaaagcag ctcaagaaca catgtgcagt cactggtgtc accctggata ggcaagggat   1980
aactcttcta acacaaaata agtgttttat gtttggaata aagtcaacct tgtttctact   2040
gttttataca ctttcaaaaa aaaaaaaaaa aaaaaaaaa a                         2081
```

<210> SEQ ID NO 24
<211> LENGTH: 2899
<212> TYPE: DNA
<213> ORGANISM: Homo sapiens
<300> PUBLICATION INFORMATION:
<308> DATABASE ACCESSION NUMBER: NM_175569
<309> DATABASE ENTRY DATE: 2009-01-04
<313> RELEVANT RESIDUES IN SEQ ID NO: (1)..(2899)

<400> SEQUENCE: 24

```
gtgcctacac tggtcccaca ggttttcagc tgtggagttt gggatctgag cttggagccc     60
atttgtttct ggcagttccg ctcatatttt ccacttgaag acatcgcctc ccttccttcc    120
aagctgggag accagaagtc aacaacagga gggtggagag gccgggtctc acaatccgct    180
tggctgggga gtccactgag gttcttgcat cctgaagcaa accatggaga gctggtgggg    240
acttccctgt cttgcgttcc tgtgttttct aatgcacgcc cgaggtcaaa gagactttga    300
tttggcagat gcccttgatg accctgaacc caccaagaag ccaaactcag atatctaccc    360
aaagccaaaa ccaccttact acccacagcc cgagaatccc gacagcggtg aaatatctaa    420
cccaaggcca aagccacgcc ctcaaccccca gcctggcaat tccggcaaca gtggaggtta    480
cttcaatgat gtggaccgtg atgacggacg ctacccgccc aggcccaggc cacggccgcc    540
tgcaggaggt ggcggcggtg gctactccag ttatggcaac tccgacaaca cgcacggtgg    600
agatcaccat tcaacgtatg gcaatccaga aggcaatatg gtagcaaaaa tcgtgtctcc    660
catcgtatcc gtggtggtgg tgacactgct gggagcagca gccagttatt tcaaaactaaa   720 caataggaga aattgtttca ggacccatga accagaaaat gtctgaagat gttaagatcc    780
cctgattact ttgagaaaaa caactaaaac aagaaccgtg tttatcactg ttgtggagat    840
ttccttttat tcttgacaca atttgatgac ctaaagtgtg ttttcttctg tgtaaagtac    900
atgagctgcc tcactaagca ttcccaactc attgaatgtg atgtggttat aaagataagt    960
taggcagcta gaccctgcgt tctaaaaaag gattgcttgc aatgttggtt tggctattca   1020
tttgcacaaa gagactgtgg ctctctgttg tgagatcttc agctacctca tggtgcaata   1080
acacacacac gcttaaccat gttgatggca caaagcggtg agcagtaggg aggtagaata   1140
tcttggtggg gagggatgt tatcagcttc tgggagatga agaatattgt tgaggttcca    1200
aagatgctgg acctgtgcta aattcttcag tgatatgaaa aaatcattga gcattcatta   1260
ttgcgaatga agtggggatg cattatttct gacacccaca agcagggttt gatcatcctt   1320
tcagctttga gatatctgca cataaaatta ttattacctg aagaaaataa ggctgcattt   1380
tgaaatgtta agtgcaaaat gactgatgtt aaaaccatct gggggaaatc ttgggatgct   1440
ttttcctagg aaatcatatg gttgtgatat gttttggcgc ataggagaca gaaatagtga   1500
```

```
ttatcaggcg ttgagccttt ttgtagtatt tttagtcttt gatactctgt aagtgctagt    1560
tcctaaggca ccaacattgc attccttggt ttatactttt tctattcatc agggtaggaa    1620
gtcttaaatc cttaggcatc caagaagtat actagctttt tgcttctctt ttagaaatac    1680
ttgtggggag agaaaaaagg atggtttggg catattggta tagtttgagt aaactaaggt    1740
taatgttcat ataacattta gactttgcca taaatatcag aaccaaagat caagacattc    1800
atgtacagtc tggaatgtat atatgggggcc cataaaaatt cccagtatgc atgttttatg    1860
ctcaccatta tgaattgggg tcttcaaaga gagaaggttg aaagtggaaa gcacttgaaa    1920
gggctccccg gtttgtaaaa tatctttaat cattcacatt aggtacctcg gagttgcggg    1980
tctcaaatgt ggattcatgc atcatttgtg cagtttgaag atagtccata tttcctattt    2040
cagtattagg tcctgcaaca cttttcaatt cttgtagaag gttttttttca ggagtggtga    2100 tgtctgatgc tcaattacta ttttccctat aagagtttca gcatgagctt aattaaattc    2160
ttgtgaaaaa acctgtgttt ttagttacac acacacacac acacacacct acttaaatgg    2220
aatctaaaca ttttttagcct ttaatccatt ccattttcta aaactgtcat aaactatttt    2280
taatcatttt aaataaatgt aaaagaaaaa taactggatt tgattattga atagtttttt    2340
tctatatttc acaaataaat tgtatgaaat gactgtagaa gtggcccccaa aattatgaac    2400 cttcgtagct gtgaatatga tgccataaat ctcttttaaa gctcaagata gactatgaac    2460
atatgaaata catagttacc taatcatgag actaaattca cctgggtgac aaggctaacg    2520
ttcaagctac ttaagatgaa aatatttgaa tcatgattgc ttgggggaac ctctctttga    2580
ggggtcatga ggaccacctg ctgggcattc tgttttcatg ctgagaaggt gagaattgaa    2640
cagatgagaa aagccttgat aaaacgtcat ctccatgtaa tttagagaag gataaccttg    2700
actgtacagc tgacccttga acaacacagg gctgaactgc acatgtccac ctgtatgtga    2760
gtttgcttct ggctctgcca ttactgagac agcaggacca accctccatc tactcaatgg    2820
gaagatgata aggatgaaga cctttatggt gatccgcttc cacttaataa atagtaaatt    2880
cattaaaaaa aaaaaaaaa                                                 2899
```

<210> SEQ ID NO 25
<211> LENGTH: 2014
<212> TYPE: DNA
<213> ORGANISM: Homo sapiens
<300> PUBLICATION INFORMATION:
<308> DATABASE ACCESSION NUMBER: NM_003385
<309> DATABASE ENTRY DATE: 2009-11-01
<313> RELEVANT RESIDUES IN SEQ ID NO: (1)..(2014)

<400> SEQUENCE: 25

```
aggcggcttt tggtcacagg ctcccgagtt ctcctagctg gggctgcgga gctgggggga     60
gggaagagag gaaaggggag ggggtgcctg gagaggcgga ggctcgcgcg cctgcgcatc    120
cagctccagg gacctaggt tttctatggg attcccaatc tgcagcagag atttacccga    180
gcgtgttgcg gcagcggctg ggcttgcaag gcgcgatcca agaggggattt aagcagccca    240 gagctccaga gaaaaagaga gcgagagaga accacacaca gagacggctt aagcgtttac    300
ccgaattaaa tatatatttt taaaaagaac tgttgagttt tatcattttc gttaagtgac    360
cgtgcgcagc gctgtaactg caggatgggg aagcagaata gcaaactggc ccctgaagtg    420
atggaggacc tggtgaagag cacagagttt aatgagcatg aactcaagca gtggtacaaa    480
ggatttctca aggactgtcc aagtgggagg ctaaatctcg aggaatttca gcagctctat    540
gtgaagttct ttccttatgg agacgcctcc aagtttgccc agcatgcctt ccgaaccttc    600
```

```
gacaagaatg gggacggcac cattgacttc cgagagttca tctgcgctct gtccatcacc    660 tccagggggca gctttgagca aagctgaac tgggccttca atatgtatga cctggatggt    720
gatggcaaga tcacccgagt ggagatgctg gagatcatcg aggctatcta caaaatggta    780
ggcactgtga tcatgatgaa atgaatgag gatggcctga cgcctgagca gcgagtagac    840
aagattttca gcaagatgga taagaacaaa gatgaccaga ttacactgga tgaattcaaa    900
gaagctgcaa agagcgaccc ttccattgta ttacttctgc agtgcgacat ccagaaatga    960
gctgatgtca atgctatgga ctgcacaaaa gtctcaatgt tccattcagt ctgcagctat    1020
tcacacacac acacacacac acacacacac acacacaaat attgcttgga             1080
ctacctataa atggacttgc ttcttgtgtt tgaaacactc gtgtgcatga aatgtcatt     1140 tgctaatgaa ttttaaaagc atatataaaa caaaacaaac aacctgccac aatgtgatat    1200
gtgtaatatc atttcataaa aatccctctt cctccaaagc ctgggcagaa atgtgctgca    1260
aagagttata tgacttcttg ttcatgtttt gctaatgctc gtatctcctt gattacataa    1320
tgttagtagc actgagaccc ccatggtaat gtaacttaat tataagctat gtcactaccc    1380
tcctgtaaaa tactattgga cagacacaga gggacccttg gctcctgtgt ctggtccaca    1440
caccacagaa gcttgtatta tcagtgaata taaatgtact acatttgcat gccttttggg    1500
tttgccttaa ttcttacctc atttgcatcc tatcgatctg gaaagagctg ttttggatga    1560
atgcagtata aaatgtaaaa accctgctaa atgacttatt gattaagtat atctatctat    1620
atatacatat acacaaagat attatttatc gaaagtaaaa aagatggaag tgtattggtt    1680
tctgtttgaa ttttcaaagg cttccaatgt ggtggcaata aatgtcccaa ataaatttat    1740
aacaattgat tttcccccta attcttattt tataattttta aaattgcagc agttgctagc    1800
aacaacttac taaatctact cttaaatata caactttgga atttgaagaa ttaatgacaa    1860
caaaagggaa aaaagcaact ttccaacttt tcatccaggc tcccaaaaga gggacaacga    1920
acatggcatg tgaaaagtaa aacagatttg ttcattccga aaaaaaaatg ttcattctat    1980
gacaataaat tttatctcag tgtgaaaaaa aaaa                                2014
```

<210> SEQ ID NO 26
<211> LENGTH: 5898
<212> TYPE: DNA
<213> ORGANISM: Homo sapiens
<300> PUBLICATION INFORMATION:
<308> DATABASE ACCESSION NUMBER: NM_130830
<309> DATABASE ENTRY DATE: 2008-09-19
<313> RELEVANT RESIDUES IN SEQ ID NO: (1)..(5898)

<400> SEQUENCE: 26

```
acactcatgc tgcagccttg agccgtccct cgtcctcctc tcaggctccc tcttgtccac    60
ggcgggcggg cgccgagctg ctggctatgc cactgaagca ttatctcctt ttgctggtgg    120
gctgccaagc ctggggtgca gggttggcct accatggctg ccctagcgag tgtacctgct    180
ccagggcctc ccaggtggag tgcaccgggg cacgcattgt ggcggtgccc accctctgc    240 cctggaacgc catgagcctg cagatcctca acacgcacat cactgaactc aatgagtccc    300
cgttcctcaa tatctcagcc ctcatcgccc tgaggattga aagaatgag ctgtcgcgca    360 tcacgcctgg ggccttccga aacctgggct cgctgcgcta tctcagcctc gccaacaaca    420
agctgcaggt tctgcccatc ggcctcttcc agggcctgga cagccttgag tctctccttc    480
tgtccagtaa ccagctgttg cagatccagc cggcccactt ctcccagtgc agcaacctca    540
aggagctgca gttgcacggc aaccacctgg aatacatccc tgacgagcc ttcgaccacc    600
```

```
tggtaggact cacgaagctc aatctgggca agaatagcct cacccacatc tcacccaggg    660
tcttccagca cctgggcaat ctccaggtcc tccggctgta tgagaacagg ctcacggata    720
tccccatggg cacttttgat gggcttgtta acctgcagga actggctcta cagcagaacc    780
agattggact gctctcccct ggtctcttcc acaacaacca caacctccag agactctacc    840
tgtccaacaa ccacatctcc cagctgccac ccagcatctt catgcagctg ccccagctca    900
accgtcttac tctcttgggg aattccctga aggagctctc tctggggatc ttcgggccca    960
tgcccaacct gcgggagctt tggctctatg acaaccacat ctcttctcta cccgacaatg   1020
tcttcagcaa cctccgccag ttgcaggtcc tgattcttag ccgcaatcag atcagcttca   1080
tctccccggg tgccttcaac gggctaacgg agcttcggga gctgtccctc cacaccaacg   1140
cactgcagga cctggacggg aatgtcttcc gcatgttggc caacctgcag aacatctccc   1200
tgcagaacaa tcgcctcaga cagctcccag ggaatatctt cgccaacgtc aatggcctca   1260
tggccatcca gctgcagaac aaccagctgg agaacttgcc cctcggcatc ttcgatcacc   1320
tggggaaact gtgtgagctg cggctgtatg acaatccctg gaggtgtgac tcagacatcc   1380
ttccgctccg caactggctc ctgctcaacc agcctaggtt agggacggac actgtacctg   1440
tgtgtttcag cccagccaat gtccgaggcc agtccctcat tatcatcaat gtcaacgttg   1500
ctgttccaag cgtccatgtc cctgaggtgc ctagttaccc agaaacacca tggtacccag   1560
acacacccag ttaccctgac accacatccg tctcttctac cactgagcta accagccctg   1620
tggaagacta cactgatctg actaccattc aggtcactga tgaccgcagc gtttggggca   1680
tgacccaggc ccagagcggg ctggccattg ccgccattgt aattggcatt gtcgccctgg   1740
cctgctccct ggctgcctgc gtcggctgtt gctgctgcaa gaagaggagc caagctgtcc   1800
tgatgcagat gaaggcaccc aatgagtgtt aaagaggcag gctggagcag ggctggggaa   1860
tgatgggact ggaggacctg ggaatttcat ctttctgcct ccaccctggg tccatggag    1920 cttttcccgtg attgctcttt ctggccctag ataaaggtgt gcctacctct tcctgacttg   1980
cctgattctc ccgtagagaa gcaggtcgtg ccggaccttc ctacaatcag gaagatagat   2040
ccaactggcc atggcaaaag ccctggggat ttccgattca taccctggg cttccttcga    2100 gagggctctt cctccaaatc ctccccacct gtcctccaag aacagccttc cctgcgccca   2160
ggccccctcc gggcctctgt agactcagtt agtccacagc ctgctcactt cgtgggaata   2220
gttctccgct gagatagccc ctctcgccta agtattatgt aagttgattt cccttctttt   2280
gtttctcttg tttgtgctat ggcttgaccc agcatgtccc ctcaaatgaa agttctcccc   2340
ttgattttct gctcctgaag gcagggtgag ttctctcctc aaagaagact caaaccatt    2400 taactggttt cttaagagcc gtcaatcagc ctggttttgg ggatgctatg aaagagagaa   2460
ggaaaatcat gccgctcagt tcctggagac agaagagccg tcatcagtgt ctcacttgtg   2520
atttttatct ggaaaaggaa gaaacaccccc agcacagcaa gctcagcctt ttagagaagg   2580
atatttccaa actgcaaact ttgctttgaa aagtttagcc cttaaggaa tgaaatcatg    2640 tagaattttg gacttctaaa aacattaaaa tcagcttatt aatacgggat agagaaagaa   2700
atctggtgcc tgggggtccc tgtgttcacc cctagagttt gttttaaaat tttaattga    2760 agcatgtgaa gtgtacctgc agaaaagtgg gaacatgata gtgtatggct tggtggattt   2820
tcacaaactg aacatacctg tgtaatcagc atctagaccc agacccagag cgtcacaaat   2880
atcccccatc ctgggctttt cccagaggag atggggggct ctgaagatgg acttacctgg   2940
gacctgcccc ccatgagcca ggacggtccc cccacagtca gcctgtgcaa aggccccgtg   3000
```

```
gccaggggtg gaggagaata tgtgggtgtg gacaggatgg gagactgtgg cctgaacagg    3060
agattttatt atatctggag accctgagag accctgagac ctggggcacc ctggctggcc    3120
aggtcagaag catcctgact gcagaggtcc gtgcagccac accctcttcc ctgccagcaa    3180
gctgtctgcg gctcatcgga ggcccctccg cctggagcct tctatggacg tgatatgcct    3240
gtatctgttt ttaattttca ttcttcactt aggggaagtg aaatcgctca gagatgagat    3300
cctttaattg aaaacgaagt gtaacggaat ctagtgtctt tctaatgtgg taaaattctc    3360
catcaacatc acagtcagct ggcagctgaa cttcagaatc tcacttacag caggcgacac    3420
gggggtacac cgatgggtca cactgggtct ggggctccc tggagctcct cctgcgtgtg    3480
gtctggttag gagttgagtt gtttgctcca gggttattct cctcctcgag tcacagtcac    3540
acgaatacct gccttctctg gctttcctgc tatacacata ttcacatggc gctcaagaag    3600
ttaggctcat ggcaacgtgt gtctttctct ggacaactgg cccagtttac agtgaaatgg    3660
agaatttcag gtctccacgt ctgcccagga aagaacttca gctgactcca cggggatctg    3720
gaaatccacg accaatcccg atcggctctt attagctccc cgctccacaa gacacctgtg    3780
ctttggaaat ccaccaccaa tcccgatcgg ctcttattag ctccccgctc acaagacac    3840 ctgtgatctg gaaatctacc accaatcccg atcggctctt attagctccc cgctccacaa    3900
gacacctgtg acatcctcca gggccacagg agcacgtgct gaccagtttt cccttccagt    3960
tcctgcacaa aaagtgtcca gagggctgtt tgcaaacact agtgcacttt gtagcttttc    4020
accctctgtc ccagggaatc taggagagat gaggcccgtc agagtcaaga gatgtcatcc    4080
ccccagggtc tccaaggcat tccacacta ttggtggcac ctggaggaca tgcaccaagg    4140
cttgccagag ccaacaggaa gtgagcccag agcatggcac atgagcatca cccgctgatg    4200
gtggcctgct gtgcctggtg ccaacagggg catcccggcc catacccctc cagacaggaa    4260
gcatgggttt gcccacagac ctgtcgggtg ctcctgtgag tggcctccag atgtctttgt    4320
gcataggcac aagtgggcca gggctggagg gaggtggaa acctcatcat ccggtgggcc    4380
ctgccaatct aacccagaa ccctaggta ttcctggcag tagccatgac attggagcac    4440
cttcctctcc agccagaggc tgacctgagg gccactgtcc tcagatgaca ccacccagga    4500 gcacctagg tgaggggtga ggcccccctt atgtgaacct cttgcctctt cctttctccc    4560
atcagagtgg ttggatggag ccattggcct ccttttcttc agcgggccct tcaacctctc    4620
tgcaccatgt tgtctggctg aggagctact agaaaagctg agtggagtct cctttccaac    4680
aggatgatgc atttgctcaa ttctcagggc tggaatgagc cggctggtcc cccagaaagc    4740
tggagtgggg tacagagttc agttttcctc tctgtttaca gctccttgac agtcccacgc    4800
ccatctggag tgggagctgg gagtcagtgt tggagaagaa acaacaaaag ccaattagaa    4860
ccactatttt taaaagtgc ttactgtgca cagatactct tcaagcactg gacgtggatt    4920
ctctctctag ccctcagcac ccctgcggta ggagtgccgc ctctacccac ttgtgatggg    4980
gtacagaggc acttgctctt ctgcatggtg ttcaataggc tgggagtttt atttatctct    5040
tcaaactttg tacaagagct catggcttgt cttgggcttt cgtcattaaa ccaaaggaaa    5100
tggaagccat tcccctgttg ctctccttag tcttggtcat cagaacctca cttggtacca    5160
tatagatcaa aagctttgta accacaggaa aaaataaact cttccatccc ttaaagaata    5220
gaatagtttg tccctctcat gggaattggg ctgtatgtat attgttcttc ctccttagaa    5280
tttagagata caagagttct acttagaact tttcatggac acaatttcca caacctttca    5340
gatgctgatg tagagctatt gggaaagaac ttccaaactc aggaagtttg cagagagcag    5400
```

| | | | | |
|---|---|---|---|---|
| acagctagag | ataactcggg | acccagagtt | ggtcgacaga | tgttagatgt | atcctagctt | 5460 |
| ttagctataa | accactcaaa | gattcagccc | ccagatccca | cagtcagaac | tgaatctgcg | 5520 |
| ttgttgggaa | gccagcagtg | gccttgggaa | ggaagccatg | gctgtggttc | agagagggtg | 5580 |
| ggctggcaag | ccacttccgg | ggaaaactcc | ttccgcccca | ggtttcttct | tctcttaagg | 5640 |
| agagattatt | ctcaccaacc | cgctgccttc | atgctgcctt | caaagctaga | tcatgtttgc | 5700 |
| cttgcttaga | gaattactgc | aaatcagccc | cagtgcttgg | cgatgcattt | acagatttct | 5760 |
| aggccctcag | ggttttgtag | agtgtgagcc | ctggtgggca | gggttggggg | gtctgtcttc | 5820 |
| tgctggatgc | tgcttgtaat | ccatttggtg | tacagaatca | acaataaata | atatacatgt | 5880 |
| ataaaaaaaa | aaaaaaaa | | | | | 5898 |

<210> SEQ ID NO 27
<211> LENGTH: 3768
<212> TYPE: DNA
<213> ORGANISM: Homo sapiens
<300> PUBLICATION INFORMATION:
<308> DATABASE ACCESSION NUMBER: NM_144668
<309> DATABASE ENTRY DATE: 2009-01-25
<313> RELEVANT RESIDUES IN SEQ ID NO: (1)..(3768)

<400> SEQUENCE: 27

| | | | | | | |
|---|---|---|---|---|---|---|
| ggagcttggg | tggcaaccag | aactagggag | ctggtggaga | aggtggcggc | cgctggaagg | 60 |
| aggcccggga | ggtggctgag | gggtccaggc | ggcgggacga | ctctggcctt | ttgaagaccg | 120 |
| ggaggaaact | ctacagagaa | gaatgtcaga | tgcagcagaa | gctccccgag | aagcaacagg | 180 |
| agaaaatgga | gaaacagaaa | tgaaagaaga | ggaggaacct | aatccaaatt | ataagaagt | 240 |
| agaagatcca | caacaggaat | caaaagatga | cacaatagca | tggagagagt | ctcaggagga | 300 |
| ggagaggaaa | acgggcgagg | aggaagggga | ggaggagggg | aaggaggaca | aaaagattgt | 360 |
| catgaagaa | actgaggaaa | aggctggaga | agtccaagag | aaggaggctt | caggaataca | 420 |
| ggaagaaacc | acagtagagc | cccaagaagt | cacagcgtcc | atgatccgtt | tggagacaca | 480 |
| gattactgat | tcccagtcaa | tcacatcagg | aatttttccca | aaaacccaaa | gaggtagcaa | 540 |
| gtcaaagctt | tccttacaat | tggaggatgc | agaaacagat | gagcttttaa | gagacctgag | 600 |
| cacacaaatt | gaatttcttg | atttggatca | aatcagtcct | gaggaacaac | agattagttc | 660 |
| ccctgaaagg | cagccctcag | gagagcttga | ggagaaaacc | gaccggatgc | cccaagatga | 720 |
| actgggacaa | gaaagaaggg | acttggagcc | agaaaacaga | gaggagggac | aagaaaggag | 780 |
| agtatccgac | atccagtcca | aagcagggat | ctcccgggag | tcactggtgt | ccagcaccac | 840 |
| agaggacatt | ctgttttcaaa | aggataaaag | cacccccggtg | tatcccttga | ccatgacctg | 900 |
| gtcgtttgga | tggaacagtt | ctcttcctgt | ttactatatt | cgagaggaaa | ggcagagagt | 960 |
| tcttctgtat | gtttgtgctc | acactgcgat | catctacaac | gtgttcagga | acaatcaata | 1020 |
| ccaccttcag | ggccacgcca | atattatctc | ctgcctctgc | gtcagtgaag | acaggcggtg | 1080 |
| gatcgccaca | gcagacaaag | ggccagactg | cctggtgatt | atatgggact | ccttcacagg | 1140 |
| tattcctgtg | cacacaatat | ttgacagctg | ccctgaaggg | aatggcatca | tggccatggc | 1200 |
| catgacccac | gacgccaagt | atctggcaac | catctcagat | gctgaagtcc | agaaggtatg | 1260 |
| catctggaag | tggactttgg | cagtggaaac | gccagcatgc | actctcgaac | tccccacaga | 1320 |
| gtacggtgtt | cagaactacg | ttacttttaa | cccaacaaat | aataaagaat | tggtgagcaa | 1380 |
| tagtaaaaca | cgggcaatat | attatgcatg | gtatgaagag | agggtatacac | tggctcacag | 1440 |
| tgccccactt | ttaactgaaa | aaaccttcaa | caagcttgtg | ggaaagttta | gccagtccat | 1500 |

```
ctttcacttg aatttaacac aaatactctc agccacaatg aagggaagc tggttgtctg    1560 ggacatacac cgcccaccct catctgcctc caccttttg ggctttccct atatcaagcc     1620
ttgtaaattg gttcatttgc agaaagaggg tatcacggta cttaccacaa ttgatagcta   1680
cattgtcaca ggtgacatta aggggaacat aagttctat gatcacaccc tgtctattgt    1740
taactggtac agtcacttga aactgggcgc cataagaact ctgtcctttt caaagacccc   1800
agcaactcct cctactgaaa aatcaaacta tcctcctgac tgcactttaa aaggtgacct   1860
ttttgtctta aggaattta tcattggaac atctgatgcc gcggtgtacc acttaacaac    1920
agatgggacc aaacttgaga agttatttgt agagcccaag gatgccattt gtgccatctc   1980
ctgccaccca tatcaacccc tcattgccat cgggagcatc tgtgggatga tcaaagtgtg   2040
gaattatgaa acaaacaat atcttttcag cagggttttt gagaaggggc ttggagtcca    2100
gagtctgacc tacaaccccg aaggagccct tcttggagct ggctttacag aggggacagt   2160
ttacattctt gatgcaatgt ctttagaaaa tgaaagccca gagcctttca aatattccag   2220
aaccagtgtg actcatataa gcttttccca tgactcccag tatatggcaa ctgctgatag   2280
aagttttact gtggctgttt acatgctggt ggtcagaaat ggacagaggg tctgggagta   2340
cttagcaaga cttcgctctc atcgcaaaag cattcgaagt ctcctgtttg gggtttacct   2400
ggacagcaat gagcctagac tgctgagcct tgggacagac aggctcttga tagagtatga   2460
tcttctcagg agctacaaag accacctgga agtcctggac attcaccaca ccgaccaggg   2520
ctgctatccc acctgcatgg tctggtaccc accactcacc agggaactct tcctgcttat   2580
ttgcaacagt ggctacaaag tgaagctttt taatgctact accaaaatgt gcagaaagac   2640
gcttctgggg ccagcttatg gttccccatat tgagcagaca caagtcctcc cagtgagaag   2700
catggcggag ctacagaaac gctacttggt gtttattaac agagacaagg tgggacttca   2760
gatcttacca gttgacggca atccacataa gacatctgct attgtttgcc acccgaacgg   2820
ggtggccggc atggccgttt cctatgatgg ctgctacgcc ttcactgcgg gagggcacga   2880
tcgctcggtg gtgcagtgga aaatcacctt aagtgtcctg gaggcagcgg tttctcttgg   2940
gggtgaagac ttgaccccat tctatggtct gctgtctggt ggccgggaag gaaaattcta   3000
cagggagcta aagactact tctactattc tcagctccgc agtcaaggca tcgacacaat    3060
ggagaccaga aaggtgtcag aacacatttg cctgtcagag cttccttttg tcatgagagc   3120
aattggcttt tacccatctg aagagaagat tgatgatata tttaacgaaa tcaaatttgg   3180
tgaatatgtg gacactggaa agctaatcga caagatcaac ttaccagatt tcctaaaagt   3240
gtaccttaac cacaagccac cttttggtaa caccatgagt ggcatccaca gagctttga    3300 ggtgctcggt tataccaact ccaaaggaa aaaggccatt cgaagagagg acttcctgag   3360
actgctcgtt actaaaggtg agcatatgac ggaggaggag atgttggatt gctttgcttc   3420
actgtttggc ctgaatcccg agggatggaa atccgagcct gcaacctgct ccgtcaaagg   3480
ttcagaaatt tgccttgaag aagaacttcc agacgaaatc actgcagaaa tattcgcgac   3540
tgaaattctt ggcttaacca tttcagaaga ttccggccag gatggtcagt gaagttacca   3600
ggaatgttta agcacaaag gactttgggt gtgtgtgcat gcacatgtgt gtgttttcca    3660
tgaggcactg cttttatgc atttccctcc cccctctcat ctttagaaca tttagacatt    3720
aaagcaagtt tctggtgagc aatggaattc acaaaaaaaa aaaaaaaa                 3768
```

<210> SEQ ID NO 28
<211> LENGTH: 2777
<212> TYPE: DNA

<213> ORGANISM: Homo sapiens
<300> PUBLICATION INFORMATION:
<308> DATABASE ACCESSION NUMBER: NM_000359
<309> DATABASE ENTRY DATE: 2009-11-22
<313> RELEVANT RESIDUES IN SEQ ID NO: (1)..(2777)

<400> SEQUENCE: 28

```
acataagtca cttaccaggt ctgtccctgc ggcatccagt ctgtgggtcc tgtcccatcc     60
atcctgacct gttccatctc agccccagga ctcagtactg cggttgccaa cactgctgcc    120
aggcatgatg gatgggccac gttccgatgt gggccgttgg ggtggcaacc ccttgcagcc    180
ccctaccacg ccatctccag agccagagcc agagccagac ggacgctctc gcagaggagg    240
aggccgttcc ttctgggctc gctgctgtgg ctgctgttca tgccgaaatg cggcagatga    300
cgactgggga cctgaaccct ctgactccag gggtcgaggg tccagctctg cactcgaag    360
acctggctcc cggggctcag actcccgccg gcctgtatcc cggggcagcg gtgtcaatgc    420
agctggagat ggcaccatcc gagagggcat gctagtagtg aacggtgtgg acttgctgag    480
ctcgcgctcg gaccagaacc gccgagagca ccacacagac gagtatgagt acgacgagct    540
gatagtgcgc cgcgggcagc cttttccatat gctcctcctc ctgtcccgga cctatgaatc    600
ctctgatcgc atcacccttg agttactcat cggaaacaac cccgaggtgg gcaagggcac    660
gcacgtgatc atcccagtgg gcaaggggg cagtggaggc tggaaagccc aggtggtcaa    720
ggccagtggg cagaatctga acctgcgggt ccacacttcc cccaacgcca tcatcggcaa    780
gtttcagttc acagtccgca cacaatcaga cgctggggag ttccagttgc cctttgaccc    840
ccgcaatgag atctacatcc tcttcaaccc ctggtgccca gaggacattg tgtacgtgga    900
ccatgaggat tggcggcagg agtatgttct taatgagtct gggagaattt actacgggac    960
cgaagcacag attggtgagc ggacctggaa ctacggccag tttgaccacg gggtgctgga   1020
tgcctgctta tacatcctgg accggcgggg gatgccatat ggaggccgtg gagacccagt   1080
caatgtctcc cgggtcatct ctgccatggt gaactccctg gatgacaatg gagtcctgat   1140
tgggaactgg tctggtgatt actcccgagg caccaaccca tcagcgtggg tgggcagcgt   1200
ggagatcctg cttagctacc tacgcacggg atattccgtc ccctatggcc agtgctgggt   1260
cttttgctgg cgtgaccacca cagtgctgcg ctgcctgggt ctggccaccc gtactgtcac   1320
caacttcaac tccgcccacg acacagacac atcccttacc atggacatct acttcgacga   1380
gaacatgaag ccctggagc acctgaacca tgattctgtc tggaacttcc atgtgtggaa   1440
cgactgctgg atgaagaggc cggatctgcc ctcgggcttt gatgggtggc aggtggtgga   1500
tgccacaccc caagagacta gcagtggcat cttctgctgc ggccctgct ctgtggagtc   1560
catcaagaat ggcctggtct acatgaagta cgacacgcct ttcattttg ctgaggtgaa   1620
tagtgacaag gtgtactggc agcggcagga tgatggcagc ttcaagattg tttatgtgga   1680
ggagaaggcc atcggcacac tcattgtcac aaaggccatc agctccaaca tgcgggagga   1740
catcacctac ctctataagc acccagaagg ctcagacgca gagcggaagg cagtagagac   1800
agcagcagcc cacggcagca aacccaatgt gtatgccaac cggggctcag cggaggatgt   1860
ggccatgcag gtggaggcac aggacgcggt gatggggcag gatctgatgg tctctgtgat   1920
gctgatcaat cacagcagca gccgccgcac agtgaaactg cacctctacc tctcagtcac   1980
tttctatact ggtgtcagtg gtaccatctt caaggagacc aagaaggaag tggagctggc   2040
accaggggcc tcggaccgtg tgaccatgcc agtggcctac aaggaatacc ggccccatct   2100
tgtggaccag ggggccatgc tgctcaatgt ctcaggccac gtcaaggaga gcgggcaggt   2160
```

| gctggccaag cagcacacct tccgtctgcg cacccagac ctctccctca cgttactggg | 2220 |
| agcagcagtg gttggccagg agtgtgaagt acagattgtc ttcaagaacc cccttcccgt | 2280 |
| caccctcacc aatgtcgtct tccggctcga aggctctggg ttacagaggc ccaagatcct | 2340 |
| caacgttggg gacattggag gcaatgaaac agtgacactg cgccagtcgt ttgtgcctgt | 2400 |
| gcgaccaggc ccccgccagc tcattgccag cttggacagc ccacagctct cccaggtgca | 2460 |
| cggtgtcatc caggtggatg tggccccagc ccctggggat gggggcttct tctcagacgc | 2520 |
| tggaggtgac agtcacttag gagagaccat ccctatggca tctcgaggtg gagcttagcc | 2580 |
| ctgtgccagg agcaatggga ctggagtcag atgagcaagg acattgcccc aagatagggg | 2640 |
| cacactacag agcagctccc caggagctca ggtggggagt ccagggctcc cggaggggga | 2700 |
| gtccagggct cccggagagg gagtcagtct tcacttgcac tgggggaaca gatgctaata | 2760 |
| aactgttttt taatgaa | 2777 |

```
<210> SEQ ID NO 29
<211> LENGTH: 1747
<212> TYPE: DNA
<213> ORGANISM: Homo sapiens
<300> PUBLICATION INFORMATION:
<308> DATABASE ACCESSION NUMBER: NM_017527
<309> DATABASE ENTRY DATE: 2009-08-10
<313> RELEVANT RESIDUES IN SEQ ID NO: (1)..(1747)

<400> SEQUENCE: 29
```

| gagttatcag aggtgagccc gtgctcttca gcggagaaga tcccctacct ggccgccggc | 60 |
| cactttctgt gggccgtggg gtcctcaagg agacggccct tgggctcagg ggctgcgttt | 120 |
| ccacacgcgc ctttcccagg gctcccgcgc ccgttcctgc ctggccgccg gccgctccaa | 180 |
| cagcagcaca aggcgggact cagaaccggc gttcagggcc gccagcggcc gcgaggccct | 240 |
| gagatgaggc tccaaagacc ccgacaggcc ccggcgggtg ggaggcgcgc gccccggggc | 300 |
| gggcggggct ccccctaccg gccagacccg gggagaggcg cgcggaggct gcgaaggttc | 360 |
| cagaagggcg gggaggggggc gccgcgcgct gaccctccct gggcaccgct ggggacgatg | 420 |
| gcgctgctcg ccttgctgct ggtcgtggcc ctaccgcggg tgtggacaga cgccaacctg | 480 |
| actgcgagac aacgagatcc agaggactcc cagcgaacgg acgagggtga caatagagtg | 540 |
| tggtgtcatg tttgtgagag agaaaacact ttcgagtgcc agaacccaag gaggtgcaaa | 600 |
| tggacagagc catactgcgt tatagcggcc gtgaaaatat ttccacgttt tttcatggtt | 660 |
| gcgaagcagt gctccgctgg ttgtgcagcg atggagagac ccaagccaga ggagaagcgg | 720 |
| tttctcctgg aagagcccat gcccttcttt tacctcaagt gttgtaaaat tcgctactgc | 780 |
| aatttagagg ggccacctat caactcatca gtgttcaaag aatatgctgg gagcatgggt | 840 |
| gagagctgtg gtgggctgtg gctggccatc ctcctgctgc tggcctccat tgcagccggc | 900 |
| ctcagcctgt cttgagccac gggactgcca cagactgagc cttccggagc atggactcgc | 960 |
| tccagaccgt tgtcacctgt tgcattaaac ttgttttctg ttgattacct cttggtttga | 1020 |
| cttcccaggg tcttgggatg ggagagtggg gatcaggtgc agttggctct taaccctcaa | 1080 |
| gggttcttta actcacattc agaggaagtc cagatctcct gagtagtgat tttggtgaca | 1140 |
| agttttctc tttgaaatca aaccttgtaa ctcatttatt gctgatggcc actcttttcc | 1200 |
| ttgactcccc tctgcctctg agggcttcag tattgatggg gagggaggcc taagtaccac | 1260 |
| tcatggagag tatgtgctga gatgcttccg acctttcagg tgacgcagga acactggggg | 1320 |
| agtctgaatg attggggtga agacatccct ggagtgaagg actcctcagc atggggggca | 1380 |

```
gtggggcaca cgttagggct gccccattc cagtggtgga ggcgctgtgg atggctgctt      1440
ttcctcaacc tttcctacca gattccagga ggcagaagat aactaattgt gttgaagaaa      1500
cttagacttc acccaccagc tggcacaggt gcacagattc ataaattccc acacgtgtgt      1560
gttcaacatc tgaaacttag gccaagtaga gagcatcagg gtaaatggcg ttcatttctc      1620
tgttaagatg cagccatcca tggggagctg agaaatcaga ctcaaagttc caccaaaaac      1680
aaatacaagg ggacttcaaa agttcacgaa aaaaaaaaa aaaaaaaaa aaaaaaaaa         1740 aaaaaaa                                                                1747

<210> SEQ ID NO 30
<211> LENGTH: 3925
<212> TYPE: DNA
<213> ORGANISM: Homo sapiens
<300> PUBLICATION INFORMATION:
<308> DATABASE ACCESSION NUMBER: NM_002317
<309> DATABASE ENTRY DATE: 2009-11-22
<313> RELEVANT RESIDUES IN SEQ ID NO: (1)..(3925)

<400> SEQUENCE: 30
attacgtgaa caaatagctg aggggcggcc gggccagaac ggcttgtgta actttgcaaa        60
cgtgccagaa agtttaaaat ctctcctcct tccttcactc cagacactgc ccgctctccg       120
ggactgccgc gccgctcccc gttgccttcc aggactgaga aaggggaaag ggaagggtgc       180
cacgtccgag cagccgcctt gactggggaa gggtctgaat cccacccttg gcattgcttg       240
gtggagactg agatacccgt gctccgctcg cctccttggt tgaagatttc tccttccctc       300
acgtgatttg agccccgttt ttattttctg tgagccacgt cctcctcgag cggggtcaat       360
ctggcaaaag gagtgatgcg cttcgcctgg accgtgctcc tgctcgggcc tttgcagctc       420
tgcgcgctag tgcactgcgc ccctcccgcc gccggccaac agcagccccc gcgcgagccg       480
ccggcggctc cgggcgcctg cgccagcag atccaatggg agaacaacgg gcaggtgttc       540
agcttgctga gcctgggctc acagtaccag cctcagcgcc gccgggaccc gggcgccgcc       600
gtccctggtg cagccaacgc ctccgcccag cagccccgca ctccgatcct gctgatccgc       660
gacaaccgca ccgccgcggc gcgaacgcgg acggccggct catctggagt caccgctggc       720
cgccccaggc ccaccgcccg tcactggttc aagctggct actcgacatc tagagcccgc       780
gaagctggcg cctcgcgcgc ggagaaccag acagcgccgg gagaagttcc tgcgctcagt       840
aacctgcggc cgcccagccg cgtggacggc atggtgggcg acgaccctta caacccctac       900
aagtactctg acgacaaccc ttattacaac tactacgata cttatgaaag gcccagacct       960
gggggcaggt accggcccgg atacggcact ggctacttcc agtacggtct cccagacctg      1020
gtggccgacc cctactacat ccaggcgtcc acgtacgtgc agaagatgtc catgtacaac      1080
ctgagatgcg cggcggagga aaactgtctg gccagtacag catacagggc agatgtcaga      1140
gattatgatc acagggtgct gctcagattt ccccaaagag tgaaaaacca agggacatca      1200
gatttcttac ccagccgacc aagatattcc tgggaatggc acagttgtca tcaacattac      1260
cacagtatgg atgagttag ccactatgac ctgcttgatg ccaacaccca gaggagagtg      1320
gctgaaggcc acaaagcaag tttctgtctt gaagacacat cctgtgacta tggctaccac      1380
aggcgatttg catgtactgc acacacacag ggattgagtc ctggctgtta tgatacctat      1440
ggtgcagaca tagactgcca gtggattgat attacagatg taaaacctgg aaactatatc      1500
ctaaaggtca gtgtaaaccc cagctacctg gttcctgaat ctgactatac caacaatgtt      1560
gtgcgctgtg acattcgcta cacaggacat catgcgtatg cctcaggctg cacaatttca      1620
```

| | |
|---|---|
| ccgtattaga aggcaaagca aaactcccaa tggataaatc agtgcctggt gttctgaagt | 1680 |
| gggaaaaaat agactaactt cagtaggatt tatgtatttt gaaaagaga acagaaaaca | 1740 |
| acaaaagaat ttttgtttgg actgttttca ataacaaagc acataactgg attttgaacg | 1800 |
| cttaagtcat cattacttgg gaattttta atgtttatta tttacatcac tttgtgaatt | 1860 |
| aacacagtgt ttcaattctg taattacata tttgactctt tcaaagaaat ccaaatttct | 1920 |
| catgttcctt ttgaaattgt agtgcaaaat ggtcagtatt atctaaatga atgagccaaa | 1980 |
| atgactttga actgaaactt ttctaaagtg ctggaacttt agtgaaacat aataataatg | 2040 |
| ggtttatata tgtcatagca tagatgaatt tagaaacaat gctcctactg tttaaataca | 2100 |
| tatggacaca tctggtgctg agaaagaaac aaacacatta ccattggtgt caagaaatat | 2160 |
| tactatatag cagagaaatg gcaatacatg tactcagata gttacatccc tatataaaaa | 2220 |
| gtatgtttac atttaaaaaa ttagtagata acttcctttc tttcaagtgc acaatttcat | 2280 |
| tttgacttga gtcaactttt gttttggaac aaattaagta agggagctgc ccaatcctgt | 2340 |
| ctgatatttc ttgaggctgc cctctatcat tttatctttc ccatgggcag agatgttgta | 2400 |
| agtgggattc ttaatatcac cattcttggg actggtatac ataaggcagc cgtgaaactg | 2460 |
| gaaagtcatt ttgatgactg atgtgataca tccagaggta aaatgcattt aaacatatta | 2520 |
| aagtatttgc caaagataca attttcttgc tgacataaaa atcacacaaa caagtccccc | 2580 |
| ccaaaccaca actgtctctc aaatagctta aaaaaattga aaaacatttt aggatttttc | 2640 |
| aagttttcta gattttaaaa agatgttcag ctattagagg aatgttaaaa atttatatt | 2700 |
| atctagaaca caggaacatc atcctgggtt attcaggaat cagtcacaca tgtgtgtgtg | 2760 |
| tctgagatat agtctaaatt agcaaagcac atagtattac atacttgagg ggttggtgaa | 2820 |
| caaaggaaaa atatactttc tgcaaaacca aggactgtgc tgcgtaatga gacagctgtg | 2880 |
| atttcatttg aaactgtgaa accatgtgcc ataatagaat tttgagaatt ttgcttttac | 2940 |
| ctaaattcaa gaaaatgaaa ttacactttt aagttagtgg tgcttaagca taattttcc | 3000 |
| tatattaacc agtattaaaa tctcaagtaa gattttccag tgccagaaca tgttaggtgg | 3060 |
| aattttaaaa gtgcctcggc atcctgtatt acatgtcata gaattgtaaa gtcaacatca | 3120 |
| attactagta atcattctgc actcactggg tgcatagcat ggttagaggg gctagagatg | 3180 |
| gacagtcatc aactggcgga tatagcggta catatgatcc ttagccacca gggcacaagc | 3240 |
| ttaccagtag acaatacaga cagagctttt gttgagctgt aactgagcta tggaatagct | 3300 |
| tctttgatgt acctctttgc cttaaattgc ttttttagttc taagattgta gaatgatcct | 3360 |
| ttcaaattgt aatctttct aacagagata ttttaatata cttgctttct taaaaaacaa | 3420 |
| aaaaactact gtcagtatta atactgagcc agactggcat ctacagattt cagatctatc | 3480 |
| attttattga ttcttaagct tgtattaaaa actaggcaat atcatcatgg atacatagga | 3540 |
| gaagacacat ttacaatcat tcattgggcc ttttatctgt ctatccatcc atcatcattt | 3600 |
| gaaggcctaa tatatgccaa gtactcacat ggtatgcatt gagacataaa aaagactgtc | 3660 |
| tataacctca ataagtatta aaaatcccat tattacccat aaggttcatc ttatttcatt | 3720 |
| tttagggaat aaaattacat gtctatgaaa tttcaatttt aagcactatt gttttttcatg | 3780 |
| accataattt attttttaaaa ataaattaaa ggttaattat atgcatgtat gtatttctaa | 3840 |
| taattaaaaa tgtgttcaat ccctgaaatg tctgcctttt aaatataaca cctactattt | 3900 |
| ggttaaaaaa aaaaaaaaaa aaaaa | 3925 |

<210> SEQ ID NO 31

<211> LENGTH: 985
<212> TYPE: DNA
<213> ORGANISM: Homo sapiens
<300> PUBLICATION INFORMATION:
<308> DATABASE ACCESSION NUMBER: NM_001785
<309> DATABASE ENTRY DATE: 2009-08-16
<313> RELEVANT RESIDUES IN SEQ ID NO: (1)..(985)

<400> SEQUENCE: 31

| | | | | | |
|---|---|---|---|---|---|
| caaaccatgg | gaggctcctc | tcctagaccc | tgcatcctga | aagctgcgta | cctgagagcc | 60 |
| tgcggtctgg | ctgcagggac | acacccaagg | ggaggagctg | caatcgtgtc | tggggcccca | 120 |
| gcccaggctg | gccggagctc | ctgtttcccg | ctgctctgct | gcctgcccgg | ggtaccaaca | 180 |
| tggcccagaa | gcgtcctgcc | tgcaccctga | agcctgagtg | tgtccagcag | ctgctggttt | 240 |
| gctcccagga | ggccaagaag | tcagcctact | gccccctacag | tcactttcct | gtgggggctg | 300 |
| ccctgctcac | ccaggagggg | agaatcttca | aagggtgcaa | catagaaaat | gcctgctacc | 360 |
| cgctgggcat | ctgtgctgaa | cggaccgcta | tccagaaggc | cgtctcagaa | gggtacaagg | 420 |
| atttcagggc | aattgctatc | gccagtgaca | tgcaagatga | ttttatctct | ccatgtgggg | 480 |
| cctgcaggca | agtcatgaga | gagtttggca | ccaactggcc | cgtgtacatg | accaagccgg | 540 |
| atggtacgta | tattgtcatg | acggtccagg | agctgctgcc | ctcctccttt | gggcctgagg | 600 |
| acctgcagaa | gacccagtga | cagccagaga | atgcccactg | cctgtaacag | ccacctggag | 660 |
| aacttcataa | agatgtctca | cagccctggg | gacacctgcc | cagtgggccc | cagccctaca | 720 |
| gggactgggc | aaagatgatg | tttccagatt | acactccagc | ctgagtcagc | acccctccta | 780 |
| gcaacctgcc | ttgggactta | gaacaccgcc | gccccctgcc | ccacctttcc | tttccttcct | 840 |
| gtgggccctc | tttcaaagtc | cagcctagtc | tggactgctt | ccccatcagc | cttcccaagg | 900 |
| ttctatcctg | ttccgagcaa | cttttctaat | tataaacatc | acagaacatc | ctggatcaaa | 960 |
| aaaaaaaaaa | aaaaaaaaaa | aaaaa | | | | 985 |

<210> SEQ ID NO 32
<211> LENGTH: 3225
<212> TYPE: DNA
<213> ORGANISM: Homo sapiens
<300> PUBLICATION INFORMATION:
<308> DATABASE ACCESSION NUMBER: NM_001012301.2
<309> DATABASE ENTRY DATE: 2009-09-03
<313> RELEVANT RESIDUES IN SEQ ID NO: (1)..(3225)

<400> SEQUENCE: 32

| | | | | | |
|---|---|---|---|---|---|
| gcgtcccgcc | cctccacctg | gggctcggcc | cggcccggca | gatgttacaa | cttttttcgaa | 60 |
| ttctctcccg | ccgtgtcccc | tcgacccgcc | caacttgtgc | ctccctcccc | ttcccctctg | 120 |
| gggtcctgcc | cacctccctg | cagggagctg | ggctgttta | aggactccgg | gtggggcgag | 180 |
| aggccgggaa | agcagaggag | agagaaatta | ggaggcggga | gaaatccagg | gcaagaagga | 240 |
| agaggggagt | cagaggatgg | tagagagcac | ttttttggaag | ctgccacgcc | gcgtctcagg | 300 |
| ctggccgggc | tgagctgggg | aagagggagc | aaaggcggcg | cagggcctgc | gcttaggcag | 360 |
| cgggaggcag | ctcggcgcgg | gcctgacctc | cccagcgcgc | cccgctgcgg | ccgagcagat | 420 |
| ccggcccagc | cgtccggcag | ccagtccggg | accagacact | ggaccgtccc | cgggggggcgc | 480 |
| tgaactccct | cgcagcatcc | gagcggcgg | gccggtggtg | cgccctgggc | gcgcgaggtg | 540 |
| gtgaggcccc | aggagcccgg | cgcgccggga | cgcgcgggcc | ggcttggcga | tgcacaccct | 600 |
| cactggcttc | tccctggtca | gcctgctcag | cttcggctac | ctgtcctggg | actgggccaa | 660 |
| gccgagcttc | gtggccgacg | ggcccgggga | ggctggcgag | cagcccctcgg | ccgctccgcc | 720 |

| | |
|---|---|
| ccagcctccc cacatcatct tcatcctcac ggacgaccaa ggctaccacg acgtgggcta | 780 |
| ccatggttca gatatcgaga ccectacgct ggacaggctg gcggccaagg gggtcaagtt | 840 |
| ggagaattat tacatccagc ccatctgcac gccttcgcgg agccagctcc tcactggcag | 900 |
| gtaccagatc cacacaggac tccagcattc catcatccgc ccacagcagc caactgcct | 960 |
| gccctggac caggtgacac tgccacagaa gctgcaggag gcaggttatt ccacccatat | 1020 |
| ggtgggcaag tggcacctgg gcttctaccg gaaggagtgt ctgcccaccc gtcgggctt | 1080 |
| cgacaccttc ctgggctcgc tcacgggcaa tgtggactat tacacctatg caactgtga | 1140 |
| tggcccaggc gtgtgcggct tcgacctgca cgagggtgag aatgtggcct gggggctcag | 1200 |
| cggccagtac tccactatgc tttatgccca gcgcgccagc catatcctgg ccagccacag | 1260 |
| ccctcagcgt cccctcttcc tctatgtggc cttccaggca gtacacacac ccctgcagtc | 1320 |
| ccctcgtgag tacctgtacc gctaccgcac catgggcaat gtggcccggc ggaagtacgc | 1380 |
| ggccatggtg acctgcatgg atgaggctgt gcgcaacatc acctgggccc tcaagcgcta | 1440 |
| cggtttctac aacaacagtg tcatcatctt ctccagtgac aatggtggcc agactttctc | 1500 |
| gggggcagc aactggccgc tccgaggacg caagggcact tattgggaag gtggcgtgcg | 1560 |
| gggcctaggc tttgtccaca gtcccctgct caagcgaaag caacggacaa gccgggcact | 1620 |
| gatgcacatc actgactggt acccgaccct ggtgggtctg gcaggtggta ccacctcagc | 1680 |
| agccgatggg ctagatggct acgacgtgtg gccggccatc agcgagggcc gggcctcacc | 1740 |
| acgcacggag atcctgcaca acattgaccc actctacaac catgcccagc atggctccct | 1800 |
| ggagggcggc tttggcatct ggaacaccgc cgtgcaggct gccatccgcg tgggtgagtg | 1860 |
| gaagctgctg acaggagacc ccggctatgg cgattggatc ccaccgcaga cactggccac | 1920 |
| cttcccgggt agctggtgga acctggaacg aatggccagt gtccgccagg ccgtgtggct | 1980 |
| cttcaacatc agtgctgacc ttatgaacgg ggaggacctg gctggccagc ggcctgatgt | 2040 |
| ggtccgcacc ctgctggctc gcctggccga atataaccgc acagccatcc cggtacgcta | 2100 |
| cccagctgag aaccccccggg ctcatcctga cttaatggg ggtgcttggg ggccctgggc | 2160 |
| cagtgatgag gaagaggagg aagaggaagg gagggctcga agcttctccc ggggtcgtcg | 2220 |
| caagaaaaaa tgcaagattt gcaagcttcg atccttttc cgtaaactca acaccaggct | 2280 |
| aatgtcccaa cggatctgat ggtggggagg gagaaaactg tcctttagag gatcttcccc | 2340 |
| actccggctt ggccctgctg tttctcaggg agaagcctgt cacatctcca tctacaggga | 2400 |
| gttgagggt gtagagtccc ttggttgaac agggtaggga gcctggatag gagtgggtgg | 2460 |
| gaataaacca gactgggatg cctgtgtctc agtcctgcct cctcacggac ttgctctgtg | 2520 |
| acctcaggtg acccacatga gcttttagcc tcagtttcct catctgtaaa atgagctcta | 2580 |
| atgactttgt gactctttgg tgtggccctg gagcctgggg ccacggtgga gttcctggcc | 2640 |
| ggccttgcca cttgacaact cctttaaggc ttccccctta acacgggatc cctgtggtgg | 2700 |
| tgtttgggag ttgcctggag gcaactccaa gcctggcccc cagctgaagc atggcaatct | 2760 |
| ggctgctctc tacagggacc cccaagcgct gtgggtggag gcaggggtc gggggggttg | 2820 |
| accttcttgg gtcttcacat ggcctaggcc agtcctccgg tcagactggt gtcaggcacc | 2880 |
| gtggtgcaaa attcctcttc tggccctcc agtacccaga gaaactggct gggccattaa | 2940 |
| ctgctgcagc accaagggtg gtagaaagag ctgtgaagag cccccaaacc agtaccagga | 3000 |
| cacctggggtt ctcctgtgac ctggggcaca gttcttgccc tctaggcctt gatttcccca | 3060 |
| cctgcaagtg gggatgccag ccctggctct gcctccttca tgaggctctg gaagactggc | 3120 |

| | |
|---|---|
| caaggttgtg gaggagcttg tgaacttgat taaagtgtcg taacatgaaa aaaaaaaaaa | 3180 |
| aaaaaaaaaa aaaaaaaaaa aaaaaaaaaa aaaaaaaaaa aaaaa | 3225 |

<210> SEQ ID NO 33
<211> LENGTH: 2614
<212> TYPE: DNA
<213> ORGANISM: Homo sapiens
<300> PUBLICATION INFORMATION:
<308> DATABASE ACCESSION NUMBER: NM_020351
<309> DATABASE ENTRY DATE: 2008-03-16
<313> RELEVANT RESIDUES IN SEQ ID NO: (1)..(2614)

<400> SEQUENCE: 33

| | |
|---|---|
| ccgatcctct ccgtgggagc cagcgagcct ctctccctga tcttacgtgc tcaagaagct | 60 |
| gttgtgaagg cagagcagca tctgctgaag agacagaaac cagccccaga ggtgtcacag | 120 |
| gaaggcacca gcaaggacat tggtctttga tttgattcag cagtcctgtc aagtataaat | 180 |
| gtgatggctg tgctgcctgg ccctctgcag ctgctgggag tgctgcttac catttccctg | 240 |
| agttccatca ggctcattca ggctggtgcc tactatggga tcaagccgct gccacctcaa | 300 |
| attcctcctc agatgccacc acaaattcca cataccagc ccctgggtca gcaagtacct | 360 |
| cacatgcctt tggccaaaga tggccttgcc atgggcaagg agatgcccca cttgcagtat | 420 |
| ggcaaagagt atccacacct accccaatat atgaaggaaa ttcaaccggc gccaagaatg | 480 |
| ggcaaggaag ccgtacccaa gaaaggcaaa gaaataccat tagccagttt acgaggggaa | 540 |
| caaggtcccc gtgagagcc tggcccaaga ggaccacctg gcccccctgg tttgccaggt | 600 |
| catgggatac ctggaattaa aggaaaacca gggccacagg gatatccagg agttggaaag | 660 |
| ccaggtatgc ctggaatgcc agggaagcca ggagccatgg gcatgcctgg ggcaaaagga | 720 |
| gaaattggac agaaagggga aattgggcct atggggatcc caggaccaca aggacctcca | 780 |
| gggcctcatg gacttcctgg cattgggaag ccagtgggc agggttacc agggcaacca | 840 |
| ggaccaaagg gtgatcgagg acccaaagga ctaccaggac ctcaaggcct tcgggtcct | 900 |
| aaaggagaca agggcttcgg gatgccaggt gcgccaggtg taaaggggcc tccagggatg | 960 |
| cacggccctc ccgccctgt tggactgcca ggagtgggca accaggagt gacaggcttc | 1020 |
| cctgggcccc agggccccct gggaaaagcca ggggctccag gagaacctgg gccacaaggc | 1080 |
| cctattgggg taccggggt tcaaggacct cctgggatac ccggaattgg aaagccaggc | 1140 |
| caggatggga tcccaggcca gccaggattt ccaggtggca aggggagca aggactgcca | 1200 |
| gggctaccag gaccccagg ccttccaggg attggaaaac aggcttccc aggacccaaa | 1260 |
| ggtgaccggg gcatgggagg tgttcctggg gctcttggac aagagggga aaaggacca | 1320 |
| ataggtgccc caggaatagg gggtcctcca ggagagccag gctgcctgg aatcccaggt | 1380 |
| cctatgggcc ctccaggtgc tattggtttt cctggaccca aggagaagg tgggattgta | 1440 |
| gggccacagg ggcaccagg tcccaagggt gagccaggc ttcaaggctt ccaggaaag | 1500 |
| ccaggtttcc ttggtgaagt agggccctcct ggcatgaggg gtttgccagg tcccataggg | 1560 |
| cccaaggggg aagctgggca aaaggtgta ccaggactcc ctggtgttcc agggcttctc | 1620 |
| ggacctaagg gagagccagg aatcccaggg gatcagggtt tacagggccc cccaggtatc | 1680 |
| ccagggattg ggggccctag tggccccatt ggaccacctg ggattccagg ccccaaaggg | 1740 |
| gagccgggcc tcccagggc ccctgggttc cctggtatag ggaaacccgg agtggcagga | 1800 |
| cttcatggcc cccagggaa gcctggtgcc cttggtcctc aaggccagcc tggccttcca | 1860 |
| ggaccccag gccctccagg acctccagga ccccagctg tgatgccccc tacaccacca | 1920 |

| | |
|---|---|
| ccccagggag agtatctgcc agatatgggg ctgggaattg atggcgtgaa acccccccat | 1980 |
| gcctacgggg ctaagaaagg caagaatgga gggccagcct atgagatgcc tgcatttacc | 2040 |
| gccgagctaa ccgcaccttt cccaccggtg ggggccccag tgaagtttaa caaactgctg | 2100 |
| tataacggca gacagaacta caacccgcag acaggcatct tcacctgtga ggtccctggt | 2160 |
| gtctactact ttgcatacca cgttcactgc aaggggggca acgtgtgggt tgctctattc | 2220 |
| aagaacaacg agcccgtgat gtacacgtac gacgagtaca aaaagggctt cctggaccag | 2280 |
| gcatctggga gtgcagtgct gctgctcagg cccggagacc gggtgttcct ccagatgccc | 2340 |
| tcagaacagg ctgcaggact gtatgccggg cagtatgtcc actcctcctt ttcaggatat | 2400 |
| ttattgtatc ccatgtaaaa acaaaaaaac aaaaaacaaa gaaagaaag agattttata | 2460 |
| gaagaaaatg acacaccaaa aaatccaaat gaaaaacata attgcttcaa aacacttaca | 2520 |
| cagttggaaa gttatatgta agtgaaaatt tggaccattg tgtacaaata aaaactaaga | 2580 |
| tgcatgttta atactcaaaa aaaaaaaaaa aaaa | 2614 |

<210> SEQ ID NO 34
<211> LENGTH: 5826
<212> TYPE: DNA
<213> ORGANISM: Homo sapiens
<300> PUBLICATION INFORMATION:
<308> DATABASE ACCESSION NUMBER: NM_003247
<309> DATABASE ENTRY DATE: 2009-09-28
<313> RELEVANT RESIDUES IN SEQ ID NO: (1)..(5826)

<400> SEQUENCE: 34

| | |
|---|---|
| gaggaggaga cggcatccag tacagagggg ctggacttgg acccctgcag cagccctgca | 60 |
| caggagaagc ggcatataaa gccgcgctgc ccgggagccg ctcggccacg tccaccggag | 120 |
| catcctgcac tgcagggccg gtctctcgct ccagcagagc ctgcgccttt ctgactcggt | 180 |
| ccggaacact gaaaccagtc atcactgcat ctttttggca aaccaggagc tcagctgcag | 240 |
| gaggcaggat ggtctggagg ctggtcctgc tggctctgtg ggtgtggccc agcacgcaag | 300 |
| ctggtcacca ggacaaagac acgaccttcg acctttttcag tatcagcaac atcaaccgca | 360 |
| agaccattgg cgccaagcag ttccgcgggc ccgaccccgg cgtgccggct taccgcttcg | 420 |
| tgcgctttga ctacatccca ccggtgaacg cagatgacct cagcaagatc accaagatca | 480 |
| tgcggcagaa ggagggcttc ttcctcacgg cccagctcaa gcaggacggc aagtccaggg | 540 |
| gcacgctgtt ggctctggag ggccccggtc tctcccagag gcagttcgag atcgtctcca | 600 |
| acggccccgc ggacacgctg gatctcacct actggattga cggcacccgg catgtggtct | 660 |
| ccctggagga cgtcggcctg ctgactcgc agtggaagaa cgtcaccgtg caggtggctg | 720 |
| gcgagaccta cagcttgcac gtgggctgcg acctcataga cagcttcgct ctggacgagc | 780 |
| ccttctacga gcacctgcag gcggaaaaga gccggatgta cgtggccaaa ggctctgcca | 840 |
| gagagagtca cttcagggt ttgcttcaga acgtccacct agtgtttgaa aactctgtgg | 900 |
| aagatattct aagcaagaag ggttgccagc aaggccaggg agctgagatc aacgccatca | 960 |
| gtgagaacac agagacgctg cgcctgggtc gcatgtcac caccgagtac gtgggcccca | 1020 |
| gctcggagag gaggcccgag gtgtgcgaac gctcgtgcga ggagctggga aacatggtcc | 1080 |
| aggagctctc gggctccac gtcctcgtga accagctcag cgagaacctc aagagagtgt | 1140 |
| cgaatgataa ccagtttctc tgggagctca ttggtggccc tcctaagaca aggaacatgt | 1200 |
| cagcttgctg gcaggatggc cggttctttg cggaaaatga acgtgggtg gtggacagct | 1260 |
| gcaccacgtg tacctgcaag aaatttaaaa ccatttgcca ccaaatcacc tgcccgcctg | 1320 |

```
caacctgcgc cagtccatcc tttgtggaag gcgaatgctg cccttcctgc ctccactcgg   1380
tggacggtga ggagggctgg tctccgtggg cagagtggac ccagtgctcc gtgacgtgtg   1440
gctctgggac ccagcagaga ggccggtcct gtgacgtcac cagcaacacc tgcttggggc   1500
cctccatcca gacacgggct tgcagtctga gcaagtgtga cacccgcatc cggcaggacg   1560
gcggctggag ccactggtca ccttggtctt catgctctgt gacctgtgga gttggcaata   1620
tcacacgcat ccgtctctgc aactcccag tgcccagat gggggcaag aattgcaaag    1680
ggagtggccg ggagaccaaa gcctgccagg gcgccccatg cccaatcgat ggccgctgga   1740
gcccctggtc cccgtggtcg gcctgcactg tcacctgtgc cggtgggatc cgggagcgca   1800
cccgggtctg caacagccct gagcctcagt acggagggaa ggcctgcgtg ggggatgtgc   1860
aggagcgtca gatgtgcaac aagaggagct gccccgtgga tggctgttta tccaacccct   1920
gcttcccggg agcccagtgc agcagcttcc ccgatgggtc ctggtcatgc ggctcctgcc   1980
ctgtgggctt cttgggcaat ggcacccact gtgaggacct ggacgagtgt gccctggtcc   2040
ccgacatctg cttctccacc agcaaggtgc ctcgctgtgt caacactcag cctggcttcc   2100
actgcctgcc ctgcccgccc cgatacagag ggaaccagcc cgtcgggtc ggcctggaag    2160
cagccaagac ggaaaagcaa gtgtgtgagc ccgaaaaccc atgcaaggac aagacacaca   2220
actgccacaa gcacgcggag tgcatctacc tgggccactt cagcgacccc atgtacaagt   2280
gcgagtgcca gacaggctac gcgggcgacg ggctcatctg cggggaggac tcggacctgg   2340
acggctggcc caacctcaat ctggtctgcg ccaccaacgc cacctaccac tgcatcaagg   2400
ataactgccc ccatctgcca aattctgggc aggaagactt tgacaaggac gggattggcg   2460
atgcctgtga tgatgacgat gacaatgacg gtgtgaccga tgagaaggac aactgccagc   2520
tcctcttcaa tccccgccag gctgactatg acaaggatga ggttgggac cgctgtgaca    2580
actgcccta cgtgcacaac cctgcccaga tcgacacaga caacaatgga gagggtgacg   2640
cctgctccgt ggacattgat ggggacgatg tcttcaatga acgagacaat tgtccctacg   2700
tctacaacac tgaccagagg gacacgatg gtgacggtgt gggggatcac tgtgacaact   2760
gcccctgg gcacaaccct gaccagaccg acgtggacaa tgaccttgtt ggggaccagt   2820
gtgacaacaa cgaggacata atgacgacg gccaccagaa caaccaggac aactgcccct    2880
acatctccaa cgccaaccag gctgaccatg acagagacgg ccaggcgac gcctgtgacc    2940
ctgatgatga caacgatggc gtccccgatg acagggacaa ctgccggctt gtgttcaacc   3000
cagaccagga ggacttggac ggtgatggac ggggtgatat ttgtaaagat gattttgaca   3060
atgacaacat cccagatatt gatgatgtgt gtcctgaaaa caatgccatc agtgagacag   3120
acttcaggaa cttccagatg gtcccttgg atcccaaagg gaccacccaa attgatccca    3180
actgggtcat cgccatcaa ggcaaggagc tggttcagac agccaactcg gaccccggca    3240
tcgctgtagg ttttgacgag tttggtctg tggacttcag tggcacattc tacgtaaaca   3300
ctgaccggga cgacgactat gccggcttcg tctttggtta ccagtcaagc agccgcttct   3360
atgtggtgat gtggaagcag gtgacgcaga cctactggga ggaccagccc acgcgggcct   3420
atggctactc cggcgtgtcc ctcaaggtgg tgaactccac cacgggacg ggcgagcacc    3480
tgaggaacgc gctgtggcac acggggaaca cgcggggca ggtgcgaacc ttatggcacg    3540
accccaggaa cattggctgg aaggactaca cggcctatag gtggcacctg actcacaggc   3600
ccaagactgg ctacatcaga gtcttagtgc atgaaggaaa acaggtcatg gcagactcag   3660
gacctatcta tgaccaaacc tacgctggcg ggcggctggg tctatttgtc ttctctcaag   3720
```

| | |
|---|---|
| aaatggtcta tttctcagac ctcaagtacg aatgcagaga tatttaaaca agatttgctg | 3780 |
| catttccggc aatgccctgt gcatgccatg gtccctagac acctcagttc attgtggtcc | 3840 |
| ttgtggcttc tctctctagc agcacctcct gtcccttgac cttaactctg atggttcttc | 3900 |
| acctcctgcc agcaacccca aacccaagtg ccttcagagg ataaatatca atggaactca | 3960 |
| gagatgaaca tctaacccac tagaggaaac cagtttggtg atatatgaga ctttatgtgg | 4020 |
| agtgaaaatt gggcatgcca ttacattgct ttttcttgtt tgtttaaaaa gaatgacgtt | 4080 |
| tacatataaa atgtaattac ttattgtatt tatgtgtata tggagttgaa gggaatactg | 4140 |
| tgcataagcc attatgataa attaagcatg aaaaatattg ctgaactact tttggtgctt | 4200 |
| aaagttgtca ctattcttga attagagttg ctctacaatg acacacaaat cccattaaat | 4260 |
| aaattataaa caagggtcaa ttcaaatttg aagtaatgtt ttagtaagga gagattagaa | 4320 |
| gacaacaggc atagcaaatg acataagcta ccgattaact aatcggaaca tgtaaaacag | 4380 |
| ttacaaaaat aaacgaactc tcctcttgtc ctacaatgaa agccctcatg tgcagtagag | 4440 |
| atgcagtttc atcaaagaac aaacatcctt gcaaatgggt gtgacgcggt tccagatgtg | 4500 |
| gatttggcaa aacctcattt aagtaaaagg ttagcagagc aaagtgcggt gctttagctg | 4560 |
| ctgcttgtgc cgctgtggcg tcggggaggc tcctgcctga gcttccttcc ccagctttgc | 4620 |
| tgcctgagag gaaccagagc agacgcacag gccggaaaag gcgcatctaa cgcgtatcta | 4680 |
| ggctttggta actgcggaca agttgctttt acctgatttg atgatacatt tcattaaggt | 4740 |
| tccagtatta aatattttgt taatatttat taagtgacta tagaatgcaa ctccatttac | 4800 |
| cagtaactta tttaaatat gcctagtaac acatatgtag tataatttct agaaacaaac | 4860 |
| atctaataag tatataatcc tgtgaaaata tgaggcttga taatattagg ttgtcacgat | 4920 |
| gaagcatgct agaagctgta acagaataca tagagaataa tgaggagttt atgatggaac | 4980 |
| cttaaatata taatgttgcc agcgatttta gttcaatatt tgttactgtt atctatctgc | 5040 |
| tgtatatgga attcttttaa ttcaaacgct gaaaagaatc agcatttagt cttgccaggc | 5100 |
| acacccaata atcagtcatg tgtaatatgc acaagtttgt ttttgttttt gttttttttg | 5160 |
| ttggttggtt tgtttttttg ctttaagttg catgatcttt ctgcaggaaa tagtcactca | 5220 |
| tcccactcca cataagggt ttagtaagag aagtctgtct gtctgatgat ggataggggg | 5280 |
| caaatctttt tccccttct gttaatagtc atcacatttc tatgccaaac aggaacaatc | 5340 |
| cataacttta gtcttaatgt acacattgca ttttgataaa attaattttg ttgtttcctt | 5400 |
| tgaggttgat cgttgtgttg ttgttttgct gcactttta cttttttgcg tgtggagctg | 5460 |
| tattcccgag accaacgaag cgttgggata cttcattaaa tgtagcgact gtcaacagcg | 5520 |
| tgcaggtttt ctgtttctgt gttgtggggt caaccgtaca atggtgtggg agtgacgatg | 5580 |
| atgtgaatat ttagaatgta ccatattttt tgtaaattat ttatgttttt ctaaacaaat | 5640 |
| ttatcgtata ggttgatgaa acgtcatgtg ttttgccaaa gactgtaaat atttatttat | 5700 |
| gtgttcacat ggtcaaaatt tcaccactga aaccctgcac ttagctagaa cctcattttt | 5760 |
| aaagattaac aacaggaaat aaattgtaaa aaaggttttc tatacatgaa aaaaaaaaa | 5820 |
| aaaaaa | 5826 |

<210> SEQ ID NO 35
<211> LENGTH: 5710
<212> TYPE: DNA
<213> ORGANISM: Homo sapiens
<300> PUBLICATION INFORMATION:
<308> DATABASE ACCESSION NUMBER: NM_015170
<309> DATABASE ENTRY DATE: 2009-10-11

<313> RELEVANT RESIDUES IN SEQ ID NO: (1)..(5710)

<400> SEQUENCE: 35

```
aggttacttg actgggagtt ctcagacctc cagtttcagc cctgccctca gcctccaatc      60
cgtaagagac acccagcccc agcaattgga ttgggcagcc cgtcttgaca caccactgtg     120
ctgagtgctt gaggacgtgt ttcaacagat ggttggggtt agtgtgtgtc atcacattcg     180
agtgggatt aagagaagga aggctgcctt gctggagctg tgtggtcttc tccaagtgag      240
agtcgcaggc aatagaacta ctttgctttt ggaggaaaag gaggaattca ttttcagcag     300
acacaagaaa agcagttttt ttttcaggga ttcttcactt ctcttgaaca aggaactcac     360
tcagagacta acacaaagga agtaatttct tacctggtca ttatttagtc tacaataagt     420
tcatccttct tcagtgtgac cagtaaattc ttcccatact cttgaagaga gcataattgg     480
aatggagagg tgctgacggc cacccaccat catctaaaga agataaactt ggcaaatgac     540
atgcaggttc ttcaaggcag aataattgca gaaaatcttc aaaggaccct atctgcagat     600
gttctgaata cctctgagaa tagagattga ttattcaacc aggataccta attcaagaac     660
tccagaaatc aggagacgga gacattttgt cagttttgca acattggacc aaatacaatg     720
aagtattctt gctgtgctct ggttttggct gtcctgggca cagaattgct gggaagcctc     780
tgttcgactg tcagatcccc gaggttcaga ggacggatac agcaggaacg aaaaaacatc     840
cgacccaaca ttattcttgt gcttaccgat gatcaagatg tggagctggg gtccctgcaa     900
gtcatgaaca aaacgagaaa gattatgaa catggggggg ccaccttcat caatgccttt     960
gtgactacac ccatgtgctg cccgtcacgg tcctccatgc tcaccgggaa gtatgtgcac    1020
aatcacaatg tctacaccaa caacgagaac tgctcttccc cctcgtggca ggccatgcat    1080
gagcctcgga cttttgctgt atatcttaac aacactggct acagaacagc cttttttgga    1140
aaatacctca tgaatataa tggcagctac atccccctg ggtggcgaga atggcttgga     1200
ttaatcaaga attctcgctt ctataattac actgtttgtc gcaatggcat caaagaaaag    1260
catggatttg attatgcaaa ggactacttc acagacttaa tcactaacga gagcattaat    1320
tacttcaaaa tgtctaagag aatgtatccc cataggcccg ttatgatggt gatcagccac    1380
gctgcgcccc acggccccga ggactcagcc ccacagtttt ctaaactgta ccccaatgct    1440
tcccaacaca taactcctag ttataactat gcaccaaata tggataaaca ctggattatg    1500
cagtacacag gaccaatgct gcccatccac atggaattta caaacattct acagcgcaaa    1560
aggctccaga ctttgatgtc agtggatgat tctgtggaga ggctgtataa catgctcgtg    1620
gagacggggg agctggagaa tacttacatc atttacaccg ccgaccatgg ttaccatatt    1680
gggcagtttg gactggtcaa ggggaaatcc atgccatatg actttgatat tcgtgtgcct    1740
tttttttattc gtggtccaag tgtagaacca ggatcaatag tcccacagat cgttctcaac    1800
attgacttgg cccccacgat cctggatatt gctgggctcg acacacctcc tgatgtggac    1860
ggcaagtctg tcctcaaact tctggaccca gaaaagccag gtaacaggtt tcgaacaaac    1920
aagaaggcca aaatttggcg tgatacattc ctagtggaaa gaggcaaatt tctacgtaag    1980
aaggaagaat ccagcaagaa tatccaacag tcaaatcact tgcccaaata tgaacgggtc    2040
aaagaactat gccagcaggc caggtaccag acagcctgtg aacaaccggg gcagaagtgg    2100
caatgcattg aggatacatc tggcaagctt cgaattcaca agtgtaaagg acccagtgac    2160
ctgctcacag tccggcagag cacgcggaac ctctacgctc gcggcttcca tgacaaagac    2220
aaagagtgca gttgtaggga gtctggttac cgtgccagca gaagccaaag aaagagtcaa    2280
```

```
cggcaattct tgagaaacca ggggactcca aagtacaagc ccagatttgt ccatactcgg    2340
cagacacgtt ccttgtccgt cgaatttgaa ggtgaaatat atgacataaa tctggaagaa    2400
gaagaagaat tgcaagtgtt gcaaccaaga aacattgcta agcgtcatga tgaaggccac    2460
aaggggccaa gagatctcca ggcttccagt ggtggcaaca gggcaggat gctggcagat     2520 agcagcaacg ccgtgggccc acctaccact gtccgagtga cacacaagtg ttttattctt    2580
cccaatgact ctatccattg tgagagaaa ctgtaccaat cggccagagc gtggaaggac      2640
cataaggcat acattgacaa agagattgaa gctctgcaag ataaaattaa gaatttaaga    2700
gaagtgagag acatctgaa gagaaggaag cctgaggaat gtagctgcag taaacaaagc     2760
tattacaata aagagaaagg tgtaaaaaag caagagaaat taaagagcca tcttcaccca    2820
ttcaaggagg ctgctcagga agtagatagc aaactgcaac ttttcaagga gaacaaccgt    2880
aggaggaaga aggagaggaa ggagaagaga cggcagagga aggggaaga gtgcagcctg     2940 cctggcctca cttgcttcac gcatgacaac aaccactggc agacagcccc gttctggaac    3000
ctgggatctt tctgtgcttg cacgagttct aacaataaca cctactggtg tttgcgtaca    3060
gttaatgaga cgcataattt tcttttctgt gagtttgcta ctggcttttt ggagtatttt    3120
gatatgaata cagatcctta tcagctcaca aatacagtgc acacggtaga acgaggcatt    3180
ttgaatcagc tacacgtaca actaatggag ctcagaagct gtcaaggata taagcagtgc    3240
aacccaagac ctaagaatct tgatgttgga aataaagatg gaggaagcta tgacctacac    3300
agaggacagt tatgggatgg atgggaaggt taatcagccc cgtctcactg cagacatcaa    3360
ctggcaaggc ctagaggagc tacacagtgt gaatgaaaac atctatgagt acagacaaaa    3420
ctacagactt agtctggtgg actggactaa ttacttgaag gatttagata gagtatttgc    3480
actgctgaag agtcactatg agcaaaataa acaaataag actcaaactg ctcaaagtga    3540
cgggttcttg gttgtctctg ctgagcacgc tgtgtcaatg gagatggcct ctgctgactc    3600
agatgaagac ccaaggcata aggttgggaa aacacctcat ttgaccttgc cagctgacct    3660
tcaaaccctg catttgaacc gaccaacatt aagtccagag agtaaacttg aatggaataa    3720
cgacattcca gaagttaatc atttgaattc tgaacactgg agaaaaaccg aaaaatggac    3780
ggggcatgaa gagactaatc atctggaaac cgatttcagt ggcgatggca tgacagagct    3840
agagctcggg cccagcccca ggctgcagcc cattcgcagg cacccgaaag aacttcccca    3900
gtatggtggt cctggaaagg acattttga agatcaacta tatcttcctg tgcattccga    3960
tggaatttca gttcatcaga tgttcaccat ggccaccgca gaacaccgaa gtaattccag    4020
catagcgggg aagatgttga ccaaggtgga gaagaatcac gaaaaggaga agtcacagca    4080
cctagaaggc agcgcctcct cttcactctc ctctgattag atgaaactgt taccttaccc    4140
taaacacagt atttctttt aactttttta tttgtaaact aataaaggta atcacagcca    4200
ccaacattcc aagctaccct gggtaccttt gtgcagtaga agctagtgag catgtgagca    4260
agcggtgtgc acacggagac tcatcgttat aatttactat ctgccaagag tagaaagaaa    4320
ggctggggat atttggggttg gcttggtttt gatttttgc ttgtttgttt gttttgtact    4380
aaaacagtat tatcttttga atatcgtagg gacataagta tatacatgtt atccaatcaa    4440
gatggctaga atggtgcctt tctgagtgtc taaaacttga caccctggt aaatcttca      4500 acacacttcc actgcctgcg taatgaagtt ttgattcatt tttaaccact ggaattttc     4560 aatgccgtca ttttcagtta gatgattttg cactttgaga ttaaaatgcc atgtctattt    4620
gattagtctt attttttat ttttacaggc ttatcagtct cactgttggc tgtcattgtg     4680
```

| | |
|---|---|
| acaaagtcaa ataaacccc aaggacgaca cacagtatgg atcacatatt gtttgacatt | 4740 |
| aagcttttgc cagaaaatgt tgcatgtgtt ttacctcgac ttgctaaaat cgattagcag | 4800 |
| aaaggcatgg ctaataatgt tggtggtgaa aataaataaa taagtaaaca aaatgaagat | 4860 |
| tgcctgctct ctctgtgcct agcctcaaag cgttcatcat acatcatacc tttaagattg | 4920 |
| ctatattttg ggttattttc ttgacaggag aaaagatct aaagatcttt tattttcatc | 4980 |
| ttttttggtt ttcttggcat gactaagaag cttaaatgtt gataaaatat gactagtttt | 5040 |
| gaatttacac caagaacttc tcaataaaag aaaatcatga atgctccaca atttcaacat | 5100 |
| accacaagag aagttaattt cttaacattg tgttctatga ttatttgtaa gaccttcacc | 5160 |
| aagttctgat atccttttaaa gacatagttc aaaattgctt ttgaaaatct gtattcttga | 5220 |
| aaatatcctt gttgtgtatt aggtttttaa ataccagcta aaggattacc tcactgagtc | 5280 |
| atcagtaccc tcctattcag ctccccaaga tgatgtgttt ttgcttaccc taagagaggt | 5340 |
| tttcttctta ttttttagata attcaagtgc ttagataaat tatgtttct ttaagtgttt | 5400 |
| atggtaaact cttttaaaga aaatttaata tgttatagct gaatctttt ggtaacttta | 5460 |
| aatcttatc atagactctg tacatatgtt caaattagct gcttgcctga tgtgtgtatc | 5520 |
| atcggtggga tgacagaaca aacatattta tgatcatgaa taatgtgctt tgtaaaaaga | 5580 |
| tttcaagtta ttaggaagca tactctgttt tttaatcatg tataatattc catgatactt | 5640 |
| ttatagaaca attctggctt caggaaagtc tagaagcaat atttcttcaa ataaaaggtg | 5700 |
| tttaaacttt | 5710 |

<210> SEQ ID NO 36
<211> LENGTH: 1511
<212> TYPE: DNA
<213> ORGANISM: Homo sapiens
<300> PUBLICATION INFORMATION:
<308> DATABASE ACCESSION NUMBER: NM_032572.3
<309> DATABASE ENTRY DATE: 2009-11-01
<313> RELEVANT RESIDUES IN SEQ ID NO: (1)..(1511)

<400> SEQUENCE: 36

| | |
|---|---|
| gtatttggga catgtaagtg gagaggcatg aacctgattc atttcctgat ccagtgatgc | 60 |
| tcccagccca cccccaaaca gacacagcgt agcccgggcc agctcttaag gagttcagga | 120 |
| gtgagaagag gccctcagag atctgacagc ctaggagtgc gtggacacca cctcagccca | 180 |
| ctgagcagga gtcacagcac gaagaccaag cgcaaagcga cccctgccct ccatcctgac | 240 |
| tgctcctcct aagagagatg gcaccggcca gagcaggatt ctgcccctt ctgctgcttc | 300 |
| tgctgctggg gctgtgggtg gcagagatcc cagtcagtgc caagcccaag ggcatgacct | 360 |
| catcacagtg gttaaaatt cagcacatgc agcccagccc tcaagcatgc aactcagcca | 420 |
| tgaaaaacat taacaagcac acaaaacggt gcaaagacct caacaccttc ctgcacgagc | 480 |
| ctttctccag tgtggccgcc acctgccaga ccccaaaat agcctgcaag aatggcgata | 540 |
| aaaactgcca ccagagccac ggggccgtgt ccctgaccat gtgtaagctc acctcaggga | 600 |
| agtatccgaa ctgcaggtac aaagagaagc gacagaacaa gtcttacgta gtggcctgta | 660 |
| agcctcccca gaaaaggac tctcagcaat tccacctggt tcctgtacac ttggacagag | 720 |
| tcctttaggt ttccagactg gcttgctctt tggctgacct tcaattccct ctccaggact | 780 |
| ccgcaccact cccctacacc cagagcattc tcttcccctc atctcttggg gctgttcctg | 840 |
| gttcagcctc tgctgggagg ctgaagctga cactctggtg agctgagctc tagagggatg | 900 |
| gcttttcatc ttttttgttgc tgttttccca gatgcttatc cccaagaaac agcaagctca | 960 |

```
ggtctgtggg ttccctggtc tatgccattg cacatgtctc ccctgccccc tggcattagg   1020
gcagcatgac aaggagagga aataaatgga aaggggggcat atgggatttg tggacacagc   1080
tgtttctgtt cctgaactag aagtcttccc cagctctgac gtggcagtga ggtgacctga   1140
aggaaagaaa aatataaata aataccactt catatttgta tagaatcctc taatcccttg   1200
tgacatagac ttgacaggga ttgtatgcct tctttatgga tgaggaaatt aaggttttag   1260
aaagcttaat gaattaaaga gcttgtctaa ttagttagta gcagaacctg gacttgaacc   1320
taggtctcct tgctctaaat acagtgtacc ttctactcta ccagttgcgc aagaaagaag   1380
tcactgttac agaggcaagc ggtgaactag gtaagagttc actcatgaag aaacgagtgc   1440
tctgaagagc cagttaccct gtgttggctg caataaaggt cattacctct ctagccaaaa   1500
aaaaaaaaaa a                                                        1511
```

METHOD FOR ANALYZING CERVICAL LYMPH NODE METASTASIS, AND TUMOR MARKER FOR HEAD AND NECK CANCER

RELATED APPLICATIONS

The present application is a U.S. National Phase Application of International Application No. PCT/JP2010/073129, filed Dec. 22, 2010, which claims priority to Japanese Application No. 2009-292611, filed Dec. 24, 2009, the disclosures of which are incorporated herein by reference in their entireties.

SEQUENCE LISTING SUBMISSION VIA EFS-WEB

A computer readable text file, entitled "IKEU-5001_SequenceListing.txt," created on or about Jun. 21, 2012, with a file size of about 118 kb contains the sequence listing for this application and is hereby incorporated by reference in its entirety.

TECHNICAL FIELD

The present invention relates to a method for analyzing cervical lymph node metastasis, and a tumor marker for head and neck cancer.

BACKGROUND ART

One of the major objects in treatment of head and neck cancer is a suppression of lymph node metastasis. As such cervical lymph node metastasis and the number of metastasized lymph nodes impose a great influence on prognosis of a patient, ascertainment of the aspect of metastasis of the cervical lymph node is necessary and indispensable for treatment. However, there is a limitation in detection of potential lymph node metastasis (smaller than about 5 mm) by the methods such as palpation and imaging diagnoses (CT, MRI, Echo, PET-CT). For a further accurate diagnosis of lymph node metastasis, a sentinel lymph node biopsy has been conducted (Non-patent documents 1-3). The sentinel lymph node biopsy has been applied clinically to various carcinomas after Morton et al. reported a usefulness of the sentinel lymph node against malignant melanoma in 1992 (Non-patent document 4), and the usefulness to the head and neck cancer also has already been reported (Non-patent documents 2 and 3).

Historical studies regarding diagnosis of lymph node micrometastasis have clarified that presence of a metastatic focus having a maximal diameter of 200 μm or more can be found with HE stain, that even a fewer tumor cells can be discovered by a concurrent use of cytokeratin immunostaining, and that one or several tumor cells can be detected in a genetic diagnosis by a realtime quantitative RT-PCR method where Squamous Cell Carcinoma Antigen (SCCA) gene is effective as the target gene for detection (Non-patent documents 5-8). Further, it has been disclosed that the lymph node metastasis of head and neck squamous cell carcinoma can be diagnosed by use of QRT-PCR method on the basis of the expression level of PVA (pemphigus vulgaris antigen) gene (Non-patent document 9).

Furthermore, for tumor markers for head and neck cancer, several genes have been disclosed (Patent documents 1 and 2).

PRIOR ART DOCUMENTS

Patent Documents

Patent document 1: JP 2007-52 A
Patent document 2: JP 2009-34071 A

Non-Patent Documents

Non-patent document 1: Satoh K, Hirayama H, et al: Sentinel lymph node biopsy using technetium 99m labeled tin colloids in breast cancer: Journal of Clinical and Experimental Medicine 192:147-150, 2000.
Non-patent document 2: Matsuzuka T, Kano M, et al: A suggested method for lymphatic mapping in squamous cell carcinoma of the head and neck: Head and Neck Cancer 27: 192-197, 2001.
Non-patent document 3: Kihara K, Kono N, et al: Study of sentinel lymph node biopsy in NO oral cancer: Head and Neck Cancer 28:108-113, 2002.
Non-patent document 4: Morton D, Wen D R, et al: Technical details of intraoperative lymphatic mapping for early stage melanoma: Arch Surg 127:392-399, 1992.
Non-patent document 5: Hamakawa H, Fukuzumi M, et al: Genetic detection of micrometastases based on SCC antigen mRNA in cervical lymph nodes of head and neck cancer: Clin Exp Metastasis 17:593-599, 1999.
Non-patent document 6: Hamakawa H, Takemura K, et al: Histological study on pN upgrading of oral cancer: Virchows Arch 437:116-121, 2000.
Non-patent document 7: Ohnishi A: Genetic diagnosis of micrometastasis of oral cancer to cervical lymph node by use of realtime quantitative PCR method: Ehime Medical Journal 21: 183-191, 2002.
Non-patent document 8: Nakashiro K, Shintani S, Ohnishi A, Terakado N, Hamakawa H: Intraoperative rapid detection of micrometastasis in sentinel lymph nodes of oral malignant tumors: Head and Neck Cancer 29:64-69, 2003.
Non-patent document 9: Ferris L. Robert et al., Cancer Res., vol. 65 (6) 2147-2156, 2005.

DISCLOSURE OF INVENTION

Problem to be Solved by the Invention

However, further analyzing methods useful for accurately grasping metastasis in a cervical lymph node and a tumor marker for head and neck cancer to be applied to the method are desired. Therefore, the present invention provides a method for analyzing metastasis of head and neck cancer to a cervical lymph node and a tumor marker for head and neck cancer used for the method.

Means for Solving Problem

The present invention relates to a method for analyzing metastasis of head and neck cancer to a cervical lymph node, and the method involves measuring an expression level of at least one gene selected from the group consisting of genes represented by SEQ ID NOS: 1 to 36 in the sequence listing in a cervical lymph node sample; and comparing the expression level with a reference value.

An aspect of the present invention relates to a tumor marker for head and neck cancer used in the method for analyzing cervical lymph node metastasis of the present invention, the tumor marker includes at least one gene selected from the group consisting of genes represented by SEQ ID NOS: 1 to 36 in the sequence listing, and/or an expression product of the aforementioned gene and/or an expression level thereof.

Effects of the Invention

The present invention provides an effect of enabling analysis of a possibility of metastasis of head and neck cancer to a cervical lymph node.

DESCRIPTION OF THE INVENTION

Figure 1:
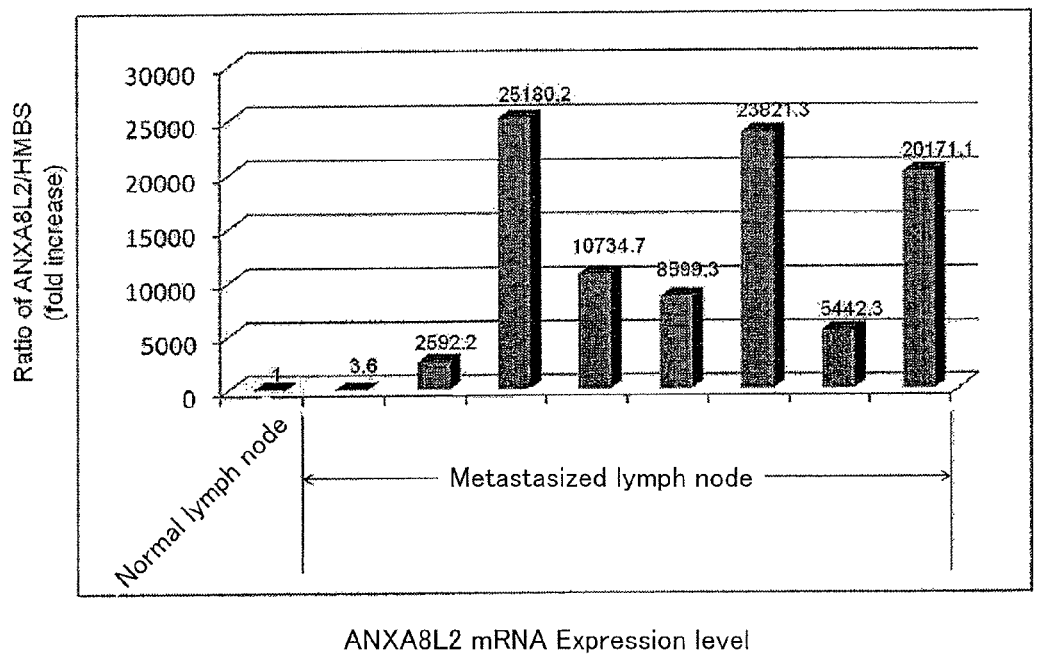
FIG. 1 is a graph showing an example of measurement of an expression level of a gene (ANXA8L2 mRNA expression level) represented by SEQ ID NO: 6 in the sequence listing at a head and neck cancer metastasized lymph node and at a normal lymph node.
Figure 2:
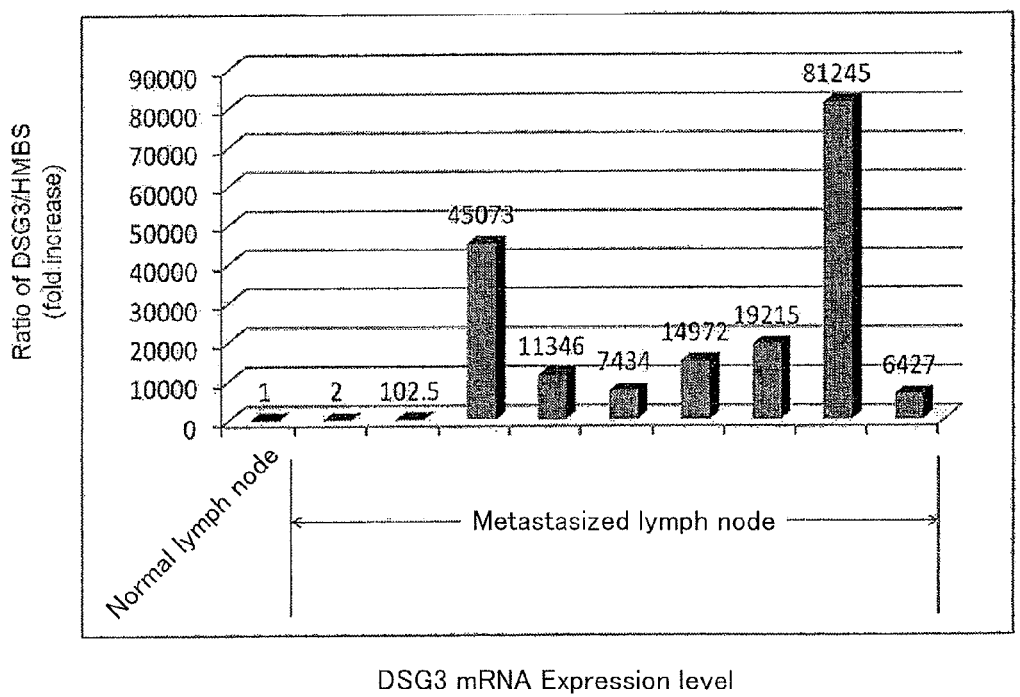
FIG. 2 is a graph showing an example of measurement of an expression level of a gene (DSG3 mRNA expression level) represented by SEQ ID NO: 9 in the sequence listing at a head and neck cancer metastasized lymph node and at a normal lymph node.
Figure 3:
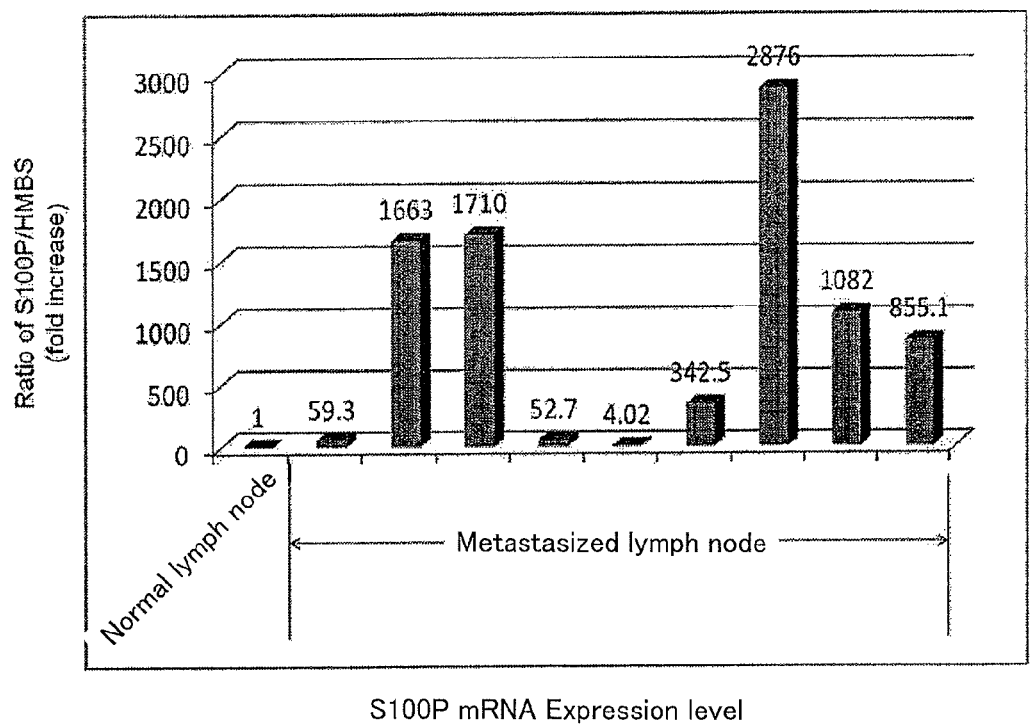
FIG. 3 is a graph showing an example of measurement of an expression level of a gene (S100P mRNA expression level) represented by SEQ ID NO: 13 in the sequence listing at a head and neck cancer metastasized lymph node and at a normal lymph node.
Figure 4:
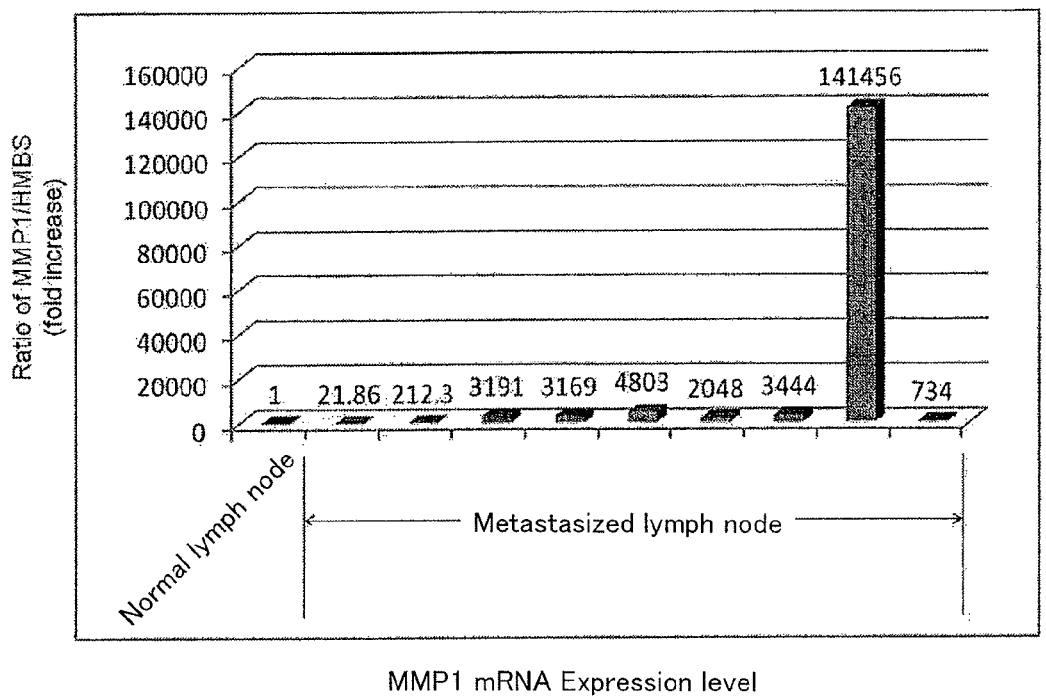
FIG. 4 is a graph showing an example of measurement of an expression level of a gene (MMP1 mRNA expression level) represented by SEQ ID NO: 23 in the sequence listing at a head and neck cancer metastasized lymph node and at a normal lymph node.

The present invention is based on a finding that 36 kinds of genes illustrated in Table 1 below can be used as tumor markers for suggesting a possibility of metastasis of head and neck cancer to a cervical lymph node. The genes have been identified, in a comparison of total genetic expression levels between the head and neck squamous cell carcinoma metastasized cervical lymph node and a cervical lymph node derived from a patient bearing no cancer (both of which are human cervical lymph nodes), as genes whose increased expressions were recognized commonly at only the metastasized lymph nodes and the expression was not detected at the salivary glands.

In the present specification, "lymph node derived from a patient bearing no cancer" denotes a cervical lymph node supplied by a patient of benign disease (non-cancerous) who underwent a cervical surgery. The lymph node derived from a patient bearing no cancer can present a state of gene expression at a cervical lymph node to which cancer has not metastasized (namely, a normal cervical lymph node). Therefore, a gene that exhibits an expression level higher at a cervical lymph node to which head and neck cancer has metastasized than at a cervical lymph node derived from a patient bearing no cancer can be used as a tumor marker to suggest a possibility of metastasis of head and neck cancer to the cervical lymph node. The 36 kinds of genes illustrated in Table 1 below satisfy this condition.

The cells of "salivary gland" are often present in a cervical lymph node. Therefore, a gene whose expression is detected in the salivary gland may cause false positive of genes that commonly exhibit increased expression at only a cancer-metastasized cervical lymph node. For the 36 kinds of genes illustrated in Table 1 below, expression is not detected in the salivary gland, and thus these genes can be used as tumor markers with a reduced risk of the aforementioned false positive. Among them, from the viewpoint of detectability of metastasis and reduction in false positive, ANXA8L2, DSG3, KRT1, KRT6A, ARSI, MMP1 and S100P are preferred for the genes to be used as the tumor markers. ANXA8L2, KRT1, KRT6A, ARSI, MMP1 and S100P are further preferred; and ANXA8L2 is particularly preferred. The aforementioned DSG3 gene is called also PVA gene (hereinafter, the same).

TABLE 1

| No. | Gene Symbol | Gene Name | RefSeq NM | UniGene | *1 | *2 | Fold Change |
|---|---|---|---|---|---|---|---|
| 1 | KRT6C | keratin 6C | NM_173086 | Hs.446417 | 12 | 1 | 3,283 |
| 2 | KRT6A | keratin 6A | NM_005554 | Hs.367762 | 12 | 2 | 2,805 |
| 3 | SPRR1B | small proline-rich protein 1B (cornifin) | NM_003125 | Hs.1076 | 1 | 3 | 2,493 |
| 4 | KRT1 | keratin 1 (epidermolytic hyperkeratosis) | NM_006121 | Hs.80828 | 12 | 4 | 2,288 |
| 5 | SPRR2E | small proline-rich protein 2E | NM_001024209.2 | null | 1 | 5 | 1,410 |
| 6 | ANXA8L2 | annexin A8-like 2 | NM_001630 | Hs.546760 | 10 | 6 | 754.7 |
| 7 | LGALS7 | lectin, galactoside-binding, soluble, 7 (galectin 7) | NM_002307 | Hs.99923 | 19 | 7 | 610.7 |
| 8 | null | Null | null | null | 1 | 8 | 571 |
| 9 | DSG3 (PVA) | desmoglein 3 (pemphigus vulgaris antigen) | NM_001944 | Hs.1925 | 18 | 9 | 444.6 |
| 10 | SPRR2F | small proline-rich protein 2F | NM_001014450.1 | null | 1 | 10 | 365.2 |
| 11 | FGFBP1 | fibroblast growth factor binding protein 1 | NM_005130 | Hs.1690 | 4 | 11 | 271.4 |
| 12 | null | Null | null | null | 10 | 12 | 246.2 |

TABLE 1-continued

| No. | Gene Symbol | Gene Name | RefSeq NM | UniGene | *1 | *2 | Fold Change |
|---|---|---|---|---|---|---|---|
| 13 | S100P | S100 calcium binding protein P | NM_005980 | Hs.2962 | 4 | 13 | 225.6 |
| 14 | A2ML1 | alpha-2-macroglobulin-like 1 | NM_144670 | Hs.334306 | 12 | 14 | 166.5 |
| 15 | BNC1 | basonuclin 1 | NM_001717 | Hs.459153 | 15 | 15 | 106.6 |
| 16 | ANXA8L2 | annexin A8-like 2 | NM_001630 | Hs.546760 | 10 | 16 | 91.76 |
| 17 | KLK8 | kallikrein-related peptidase 8 | NM_007196 | null | 19 | 17 | 88.9 |
| 18 | SCEL | Sciellin | NM_144777 | Hs.115166 | 13 | 18 | 79.3 |
| 19 | NCK1 | NCK adaptor protein 1 | NM_006153 | Hs.477693 | 3 | 19 | 70.35 |
| 20 | IL20RB | interleukin 20 receptor beta | NM_144717 | Hs.61232 | 3 | 20 | 70.35 |
| 21 | ECM1 | extracellular matrix protein 1 | NM_022664 | Hs.81071 | 1 | 21 | 44.99 |
| 22 | CAPNS2 | calpain, small subunit 2 | NM_032330 | Hs.534503 | 16 | 22 | 43.84 |
| 23 | MMP1 | matrix metalloproteinase 1 (interstitial collagenase) | NM_002421 | Hs.83169 | 11 | 23 | 43.25 |
| 24 | XG | Xg blood group (pseudoautosomal boundary-divided on the X chromosome) | NM_175569 | Hs.179675 | X | 24 | 30.96 |
| 25 | VSNL1 | visinin-like 1 | NM_003385 | Hs.444212 | 2 | 25 | 29.07 |
| 26 | LRRC15 | leucine rich repeat containing 15 | NM_130830 | null | 3 | 26 | 26.89 |
| 27 | WDR66 | WD repeat domain 66 | NM_144668 | Hs.507125 | 12 | 27 | 25.15 |
| 28 | TGM1 | transglutaminase 1 (K polypeptide epidermal type I, protein-glutamine-gamma-glutamyltransferase) | NM_000359 | Hs.508950 | 14 | 28 | 23.45 |
| 29 | LY6K | lymphocyte antigen 6 complex, locus K | NM_017527 | Hs.69517 | 8 | 29 | 21.01 |
| 30 | LOX | lysyl oxidase | NM_002317 | Hs.102267 | 5 | 30 | 20.55 |
| 31 | CDA | cytidine deaminase | NM_001785 | Hs.466910 | 1 | 31 | 16.85 |
| 32 | ARSI | arylsulfatase I | NM_001012301.2 | Hs.444709 | 5 | 32 | 12.17 |
| 33 | COL8A1 | collagen, type VIII, alpha 1 | NM_020351 | null | 3 | 33 | 8.95 |
| 34 | THBS2 | thrombospondin 2 | NM_003247 | Hs.371147 | 6 | 34 | 6.497 |
| 35 | SULF1 | sulfatase 1 | NM_015170 | Hs.409602 | 8 | 35 | 5.871 |
| 36 | RNASE7 | ribonuclease, RNase A family, 7 | NM_032572.3 | Hs.525206 | 14 | 36 | 4.014 |

Note:
*1 and *2 indicate respectively Chromosome Number and SEQ ID NO.

[Method for Analyzing Cervical Lymph Node Metastasis]

Namely, an aspect of the present invention relates to a method for analyzing metastasis of head and neck cancer to a cervical lymph node (hereinafter, referred also to as "analyzing method of the present invention"), and the method for analyzing cervical lymph node metastasis involves: measuring an expression level of at least one gene selected from the group consisting of genes represented by SEQ ID NOS: 1 to 36 in the sequence listing in a cervical lymph node sample; and comparing the aforementioned expression level with a reference value.

An embodiment of the analyzing method of the present invention includes a method for analyzing cervical lymph node metastasis, which involves measuring an expression level of at least one gene selected from the group consisting of genes represented by SEQ ID NOS: 1 to 8 and 10 to 36 in the sequence listing and comparing the expression level with a reference value.

In the present specification, "head and neck cancer" denotes a cancer that occurs in the neck and the head except for the brain and the eyes. In general, it includes oral cancer, paranasal sinus and nasal cancer, labial cancer, pharyngeal cancer, laryngeal cancer, head tumor, and cancer of ears. In the present specification, "tumor marker" is a generic term for substances that function as markers of cancer cell and thus serve as a standard for diagnosis and treatment of cancer.

In the present specification, "measuring an expression level of gene" denotes measurement of the amount of expression product of gene. In the present specification, "expression product" includes RNA ingredients contained in total RNA extracted from cells, and it may include transcription products of genes (mRNA). There is no particular limitation on the methods for measuring an expression level of gene, and the quantitative PCR method or the DNA microarray method can be conducted for example. The expression level of gene may be relative to an internal standard, or may be relative to a control sample (for example, a normal cell sample). The gene to be measured is a gene included in the above Table 1 (any of the genes represented by SEQ ID NOS: 1 to 36 in the sequential listing if there is no particular reference).

In the present specification, "cervical lymph node sample" denotes a lymph node to be analyzed for checking metastasis of head and neck cancer, and it may include for example a sentinel lymph node, and, any ambient cervical lymph nodes where head and neck cancer is/was present and a lymph node to be extracted by neck dissection. In a case of measuring expression level of gene, from the viewpoint of improvement in the accuracy in analysis, it is preferable that total RNA is recovered from the entire lymph nodes recovered from the object so as to prepare cDNA or cRNA, which is then used to conduct either the quantitative PCR method or the DNA microarray method.

In the present specification, "comparing the expression level with a reference value" denotes comparing an expression level in an analytical sample with a reference value that can be preset. In an embodiment, the reference value can be an expression level in a normal cervical lymph node. In this embodiment, in a case where the expression level of the sample is higher by preferably at least 3 times, more preferably at least 10 times, further preferably at least 30 times and further preferably at least 100 times than the reference value, it is regarded as indicating a high possibility of metastasis of head and neck cancer to the cervical lymph node of the sample. In another embodiment, the reference value can be set to be higher by preferably at least 3 times, more preferably at least 10 times, further preferably at least 30 times and further preferably at least 100 times than the expression level at a normal cervical lymph node. In this embodiment, in a case where the expression level of the sample is higher than the reference value, it is regarded as indicating a high possibility of metastasis of the head and neck cancer to the cervical lymph node of the sample.

In the present specification, though "normal cervical lymph node" can involve a cervical lymph node of a normal human individual, extraction of a lymph node of a sound and healthy human being is difficult from an ethical viewpoint. Therefore, in the present specification, "normal cervical lymph node" can involve a "cervical lymph node derived from a patient bearing no cancer", that is, a cervical lymph node supplied by a patient of a benign disease (non-cancerous) who underwent a cervical surgery.

In the analyzing method of the present invention, the number of genes used in measuring and comparing the expression level may be one kind, but from the viewpoint of accuracy in analysis, the number is preferably at least two, more preferably at least five, further preferably at least ten, and further preferably at least twenty.

In a current method of treating head and neck cancer, neck dissection, namely, removal of all of the lymph nodes present in the neck (about 30) is conducted in general. By applying the analyzing method of the present invention to these removed cervical lymph nodes, it is possible to clarify how many lymph node metastases were present at the neck and to refer to the number for reviewing and assessing the subsequent treatment policy.

The analyzing method of the present invention can be applied also to a method (sentinel lymph node biopsy) where one or two sentinel lymph node(s) is/are removed to check the presence of metastasis. In this method, a neck dissection is not conducted if there is no metastasis, while the neck dissection is conducted if there is any metastasis. It should be noted that, in an embodiment, the analyzing method of the present invention does not include either diagnosis of metastasis of head and neck cancer to a human lymph node for medical purposes, or determination of prescription and/or a plan for treatment and surgery depending on occurrence of the metastasis of the head and neck cancer to the human lymph node for medical purpose. Alternatively, in another embodiment, the analyzing method of the present invention may involve diagnosis of metastasis of head and neck cancer to a human lymph node for medical purpose and also determination of prescription and/or a plan for treatment and surgery depending on occurrence of the metastasis of head and neck cancer to a human lymph node for medical purpose.

[Tumor Marker for Head and Neck Cancer]

Another aspect of the present invention relates to a tumor marker for head and neck cancer (hereinafter, this will be referred to also as "tumor marker for head and neck cancer of the present invention") including at least one gene selected from the group consisting of genes represented by SEQ ID NOS: 1 to 36 in the sequence listing, and/or an expression product of the gene and/or an expression level thereof. The expression product may include an RNA chain to be transcribed from a template of gene DNA, namely an RNA chain synthesized by the RNA polymerase, and also an RNA chain modified within a cell after the transcription. There is no particular limitation on the RNA chain included in the expression product, and the examples include messenger-RNA (m-RNA), ribosomal RNA (rRNA), transfer RNA (tRNA), small nuclear RNA (snRNA), small nucleolar RNA (snoRNA) and any other RNAs that do not command protein. These RNA chains include also what has been processed within a cell after transcription. Further in the present specification, "gene" denotes an arbitrary fragment of DNA directed to a biofunction. In a case where polynucleotide in the sequence listing represents RNA, t (thymine) base will be read as u (uracil) base.

The tumor marker of the present invention can be set as an indicator of metastasis of head and neck cancer in a cervical lymph node. Namely, in a case where expression of the tumor marker of head and neck cancer of the present invention is increased in the cervical lymph node, there is a high possibility that metastasis occurs in the lymph node. Therefore, in an embodiment, the tumor marker of head and neck cancer of the present invention is made of a transcription product of a gene selected from the group consisting of genes represented by SEQ ID NOS: 1 to 36 in the sequence listing in the head and neck cancer, and it is a tumor marker for head and neck cancer to be used in the analyzing method of the present invention. Further, in an embodiment, the tumor marker for head and neck cancer of the present invention is made of a transcription product of at least one gene selected from the group consisting of genes represented by SEQ ID NOS: 1 to 8 and 10 to 36 in the sequence listing in the head and neck cancer, and it is a tumor marker for head and neck cancer to be used in the analyzing method of the present invention.

A further aspect of the present invention relates to a use of a tumor marker of the present invention. Specifically, the present invention relates to a use of a tumor marker of the present invention in analysis, or assessment/determination of metastasis of head and neck cancer in a sample of cervical lymph node or a head and neck lymph node. One of the embodiments thereof is a use of the tumor marker of the present invention in an analyzing method of the present invention.

Hereinafter, the present invention will be described further with reference to Examples.

EXAMPLES

Example 1

[Samples]

Samples in this Example were metastasized lymph nodes (7 samples) derived from patients of head and neck squamous cell carcinoma. For control samples, a lymph node (1 sample) and salivary glands (5 samples) derived from patients bearing no cancer were used. It should be noted that for use of the specimens in the present study, each patient and his/her family were fully informed, and thus a written consent was obtained.

[Assay]

After homogenizing mechanically the respective samples, total RNA was extracted and purified by using Isogen (Nippon Gene, Toyama, Japan). 1 µg of the total RNA was amplified by using Cheluminescent RT-IVT Labeling Kit (Applied Biosystems, FosterCity, Calif.), thereby synthesizing digoxigenin (Roche Diagnostics, Basel, Switzerland) labeled cRNA. After hybrizing the synthesized cRNA with human genome survey microarray (Applied Biosystems), it was washed by using Chemiluminescent Detection Kit (Applied Biosystems) and, after color development, expression quantification of 29,098 genes was conducted by using Applied Biosystems 1700 microarray analyzer (Applied Biosystems). Comparison in the gene expression levels of respective cases was assayed by using Gene Spring GX7.3 (Agilent Technologies, SantaClara, Calif.).

[Identification of Tumor Marker]

Comparison in the expression levels of all of the genes was conducted for 7 specimens of head and neck squamous cell carcinoma metastasized lymph nodes and 1 specimen of lymph node derived from a patient bearing no cancer. 36 kinds of genes (the genes represented by SEQ ID NOS: 1 to 36 in the sequence listing of the above Table 1) were identified as tumor markers. The genes respectively exhibited increased expression higher by at least 3 times only at metastasized lymph nodes in comparison with unmetastasized lymph nodes, and no expression was detected in the salivary glands. The degree of increased expression at each gene is indicated as "change fold" in Table 1. Two kinds of new genes that have not been registered in the identified RefSeq or UniGene are recognized (the genes represented by SEQ ID NOS: 8 and 12 in the sequence listing), and 12 kinds of genes whose relationship with cancer has been reported were included in the Table.

[Use of Tumor Marker]

mRNA expression levels of the genes of SEQ ID NOS: 6, 9, 13 and 23 in the sequence listing (respectively ANXA8L, DSG3(PVA), S100P and MMP1 genes) were measured for the head and neck squamous cell carcinoma metastasized lymph nodes of new 9 samples, and the expression levels were compared with the expression level at a normal lymph node (lymph node derived from a patient bearing no cancer). The measurement of expression level was conducted by the realtime quantitative RT-PCR method. Namely, by using 100 ng of TOTAL RNA derived from each lymph node tissue as a template, each mRNA was reverse-transcribed and amplified at Light Cycler (Roche Diagnostics) by using specific primer. At the same time, an amplification product was detected by use of TaqMan (registered trademark) probe (Applied Biosystems) or SYBR (registered trademark) Green I (Takara, Otsu, Japan), thereby quantifying the expression levels of the respective genes.

The results are shown in FIGS. 1 to 4. As illustrated in these figures, for all of the head and neck squamous cell carcinoma metastasized lymph node samples, the four genes exhibited expression levels higher than the expression level at the normal lymph node sample. Further, for all excepting one of the head and neck squamous cell carcinoma metastasized lymph node samples, the four genes exhibited expression levels higher by at least three times than the expression level at the normal lymph node sample.

Example 2

[Samples]

Samples in this Example were 8 specimens of lymph nodes. Regarding the specimens, the metastasis had been determined as negative in a conventional metastasis genetic test for detecting Cytokeratin19 (CK19) mRNA, but metastasis of head and neck cancer had been clarified by a microscopic examination on pathological tissues. It should be noted that for use of the specimens in the present study, each patient and his/her family were fully informed, and thus a written consent was obtained.

[Use of Tumor Marker]

mRNA expression levels of the genes of SEQ ID NOS: 6 and 9 in the sequence listing (respectively ANXA8L2 and DSG3(PVA) genes) were measured for the samples, and the expression levels were compared with the expression level at a normal lymph node (lymph node derived from a patient bearing no cancer). The measurement of expression level was conducted by the realtime quantitative RT-PCR method similarly to Example 1.

Figure 5:
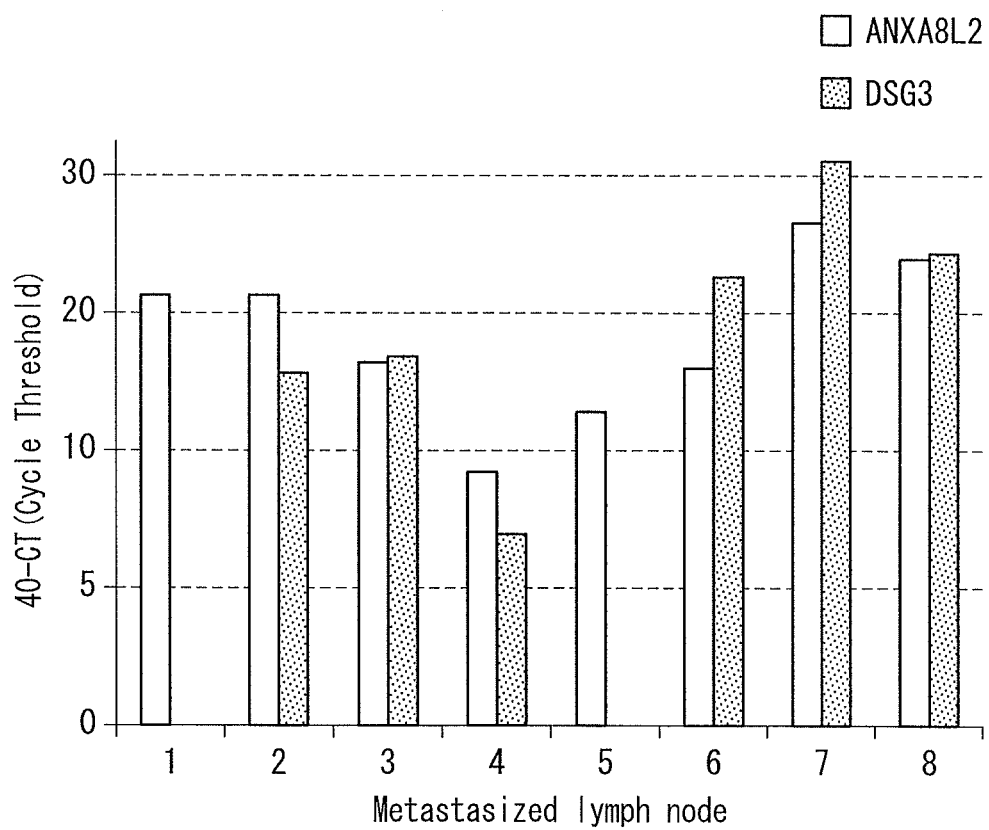
FIG. 5 is a graph showing an example of a result of detecting mRNA of ANXA8L and DSG3 genes by the RT-PCR method with regard to 8 specimens of CK19 mRNA negative head and neck cancer metastasized cervical lymph nodes.

The results are shown in FIG. 5. As illustrated in FIG. 5, for the ANXA8L2 gene, the expression was detected in all of the specimens. For the DSG3(PVA) gene, the expression was detected in all of the specimens excepting two thereof (25%).

Example 3

[Samples]

The samples in this Example were newly-prepared metastasized lymph nodes (12 samples) derived from head and neck squamous cell carcinoma patients different from those for Examples 1 and 2, and control samples were newly-prepared lymph nodes (7 samples) derived from patients bearing no cancer. It should be noted that for use of the specimens in the present study, each patient and his/her family were fully informed, and thus a written consent was obtained.

[Use Of Tumor Marker]

mRNA expression levels of the genes of SEQ ID NOS: 6, 9, 4, 2, 23, 13 and 32 in the sequence listing (respectively ANXA8L, DSG3(PVA), KRT-1, KRT-6A, MMP1, S100P and ARSI genes) were measured for the samples, and the expression levels were compared with the expression level at control samples. The measurement of expression level was conducted by the realtime quantitative RT-PCR method similarly to Example 1.

Figure 6:
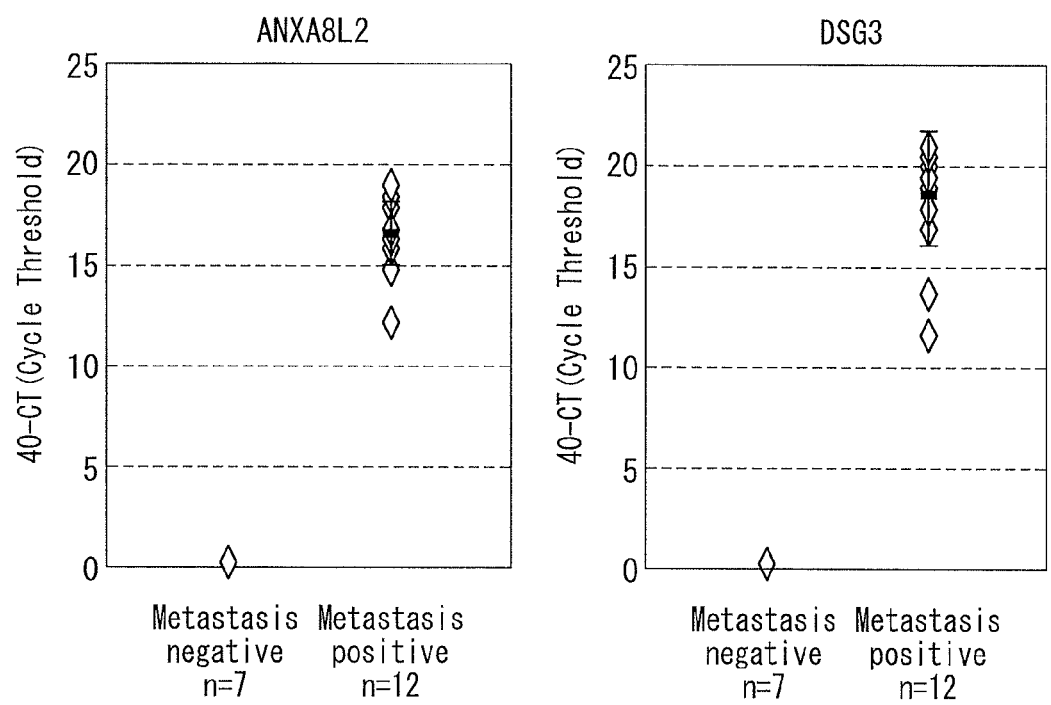
FIG. 6 is a graph showing an example of a result of detecting mRNA of ANXA8L and DSG3 genes by the RT-PCR method with regard to 7 specimens of metastasis negative and 12 specimens of metastasis positive.
Figure 7:
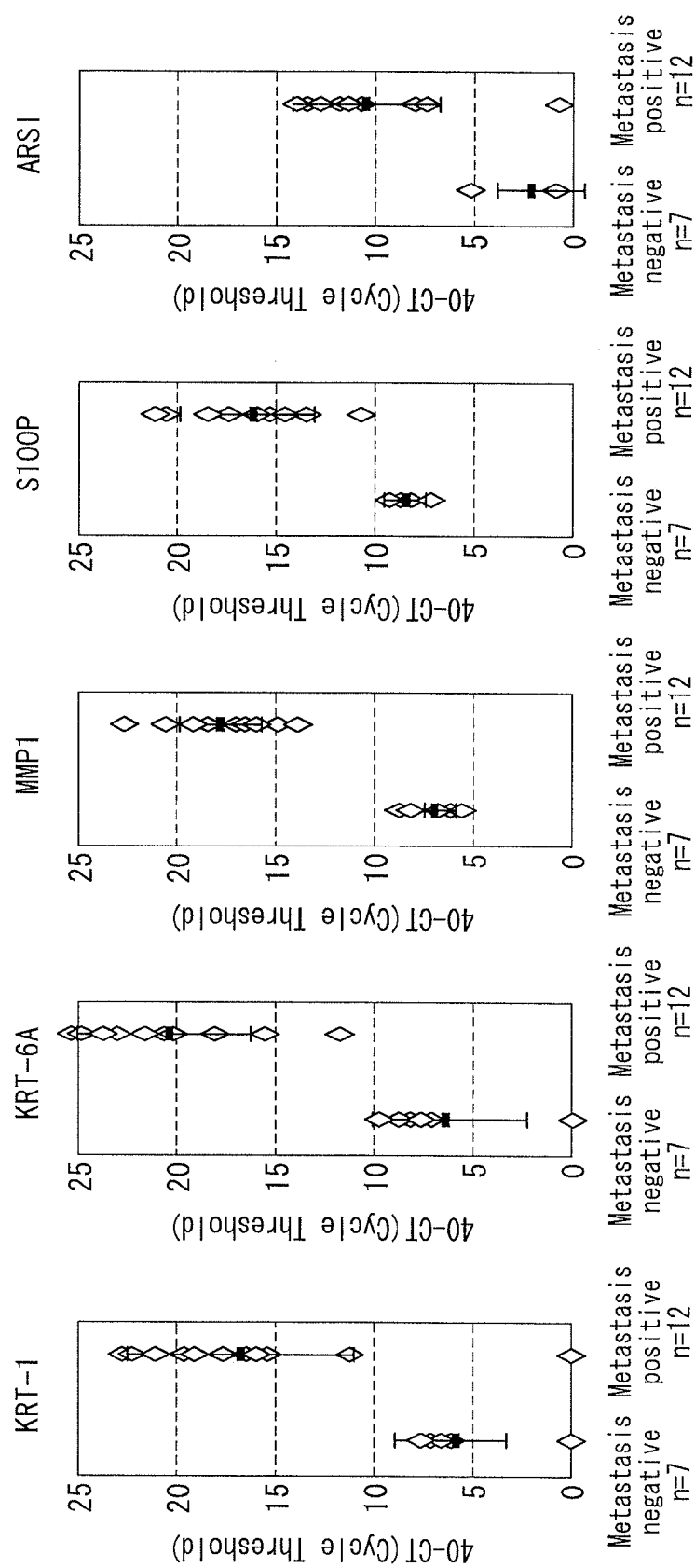
FIG. 7 is a graph showing an example of a result of detecting mRNA of KRT-1, KRT-6A, MMP1, S100P and ARSI genes by the RT-PCR method with regard to 7 specimens of metastasis negative and 12 specimens of metastasis positive.

The results are shown in FIGS. 6 and 7. As illustrated in FIG. 6, for the ANXA8L2 and DSG3(PVA) genes, no expression was recognized at the normal lymph nodes. Further, as shown in FIG. 7, for KRT-1, KRT-6A, MMP1, S100P, and ARSI genes, the expression level rose at the metastasized lymph nodes significantly in comparison with the normal lymph nodes.

INDUSTRIAL APPLICABILITY

The present invention is used favorably in the field of treatment of head and neck cancer for example.

The invention claimed is:

1. A method of analyzing metastasis of head and neck cancer to a cervical lymph node in a subject, the method comprising:
   measuring gene expression levels of SEQ ID NO: 6 and 9 in a cervical lymph node sample; and
   comparing the gene expression levels with reference values,
   wherein the gene expression levels from the cervical lymph node sample that are higher than the reference values indicate metastasis of head and neck cancer to the cervical lymph node.

2. The method of analyzing cervical lymph node metastasis according to claim 1, wherein the reference values are gene expression levels of SEQ ID NO: 6 and 9 from a normal cervical lymph node and indicate a high probability of metastasis of head and neck cancer to the cervical lymph node in a subject where the gene expression levels of SEQ ID NO: 6 and 9 from the cervical lymph node sample of the subject is higher by at least three times than the reference values.

3. The method of analyzing cervical lymph node metastasis according to claim 1, wherein the reference values are higher by at least three times than from a normal cervical lymph node and indicate a high probability of metastasis of head and neck cancer to the cervical lymph node in a subject where the gene expression levels of SEQ ID NO: 6 and 9 from the cervical lymph node sample of the subject are higher than the reference values.

4. The method of analyzing cervical lymph node metastasis according to claim 1, wherein the measurement of the gene expression levels is conducted by
   obtaining an RNA sample from the cervical lymph node,
   reverse-transcribing the RNA sample to obtain a first cDNA having a sequence of SEQ ID NO: 6 and a second cDNA having a sequence of SEQ ID NO: 9,
   measuring the levels of the cDNAs.

5. The method of analyzing cervical lymph node metastasis according to claim 4, further comprising amplifying the cDNA having a sequence of SEQ ID NO: 6.

6. The method of analyzing cervical lymph node metastasis according to claim 4, wherein the measurement of the levels of the cDNAs is conducted by real time quantitative RT-PCR.

7. The method of analyzing cervical lymph node metastasis according to claim 4, wherein the levels of the cDNAs from the cervical lymph node of the subject that are higher than the reference values are indicative of metastasis of head and neck cancer to the cervical lymph node.

* * * * *